United States Patent
Omura et al.

(10) Patent No.: US 8,604,233 B2
(45) Date of Patent: Dec. 10, 2013

(54) LUBRICANT COMPOSITION, MAGNETIC RECORDING MEDIUM, AND NOVEL POLYETHER COMPOUND

(75) Inventors: Kazufumi Omura, Odawara (JP); Yasushi Komori, Odawara (JP)

(73) Assignee: FUJIFILM Corporation, Tokyo (JP)

( * ) Notice: Subject to any disclaimer, the term of this patent is extended or adjusted under 35 U.S.C. 154(b) by 639 days.

(21) Appl. No.: 12/749,155

(22) Filed: Mar. 29, 2010

(65) Prior Publication Data

US 2010/0247971 A1 Sep. 30, 2010

(30) Foreign Application Priority Data

Mar. 30, 2009 (JP) ................. 2009-082273

(51) Int. Cl.
*C07C 69/96* (2006.01)
(52) U.S. Cl.
USPC ....................................... 558/266

(58) Field of Classification Search
USPC ........................................... 558/266
See application file for complete search history.

(56) References Cited

U.S. PATENT DOCUMENTS

| 7,088,572 B2 * | 8/2006 | Yoshida et al. ............... 361/504 |
| 2008/0020243 A1 | 1/2008 | Mori et al. |
| 2008/0241599 A1 | 10/2008 | Imakuni et al. |

FOREIGN PATENT DOCUMENTS

| JP | 07-138586 A | 5/1995 |
| JP | EP0997519 A1 * | 3/2000 |
| JP | 2008-007469 A | 1/2008 |
| JP | 2008-239575 A | 10/2008 |

* cited by examiner

*Primary Examiner* — Johann R Richter
*Assistant Examiner* — Kofi Adzamli
(74) *Attorney, Agent, or Firm* — Sughrue Mion, PLLC

(57) ABSTRACT

An aspect of the present invention relates to a lubricant composition comprising a polyether compound comprising an alkylene oxide residue and a carbonic acid ester residue.

13 Claims, No Drawings

LUBRICANT COMPOSITION, MAGNETIC RECORDING MEDIUM, AND NOVEL POLYETHER COMPOUND

CROSS-REFERENCE TO RELATED APPLICATIONS

This application claims the benefit of priority under 35 USC 119 to Japanese Patent Application No. 2009-82273, filed on Mar. 30, 2009, which is expressly incorporated herein by reference in its entirety.

BACKGROUND OF THE INVENTION

1. Field of the Invention

The present invention relates to a lubricant composition, and more particularly, to a lubricant composition comprising a polyether compound having a good lubricating effect that can increase resistance to abrasion and reduce friction during frictional sliding.

The present invention further relates to a magnetic recording medium comprising a layer containing the above polyether compound, and a novel polyether compound.

2. Discussion of the Background

In recent years, the need for high-density recording has been increasing, and there is demand for a magnetic recording medium having good electromagnetic characteristics. However, when the smoothness of the magnetic layer surface is increased for high density recording, the increase in the coefficient of friction may compromise running properties and durability. Accordingly, various attempts to lower the coefficient of friction have been made by adding a lubricant to the magnetic layer and nonmagnetic layer in particulate magnetic recording media (for example, see Japanese Unexamined Patent Publication (KOKAI) No. 2008-239575 or English language family member US 2008/0241599 A1 and Japanese Unexamined Patent Publication (KOKAI) No. 2008-7469 or English language family member US 2008/0020243 A1), and by coating a lubricant on the magnetic layer in a thin-film magnetic recording medium to form a lubricant film (for example, see Japanese Unexamined Patent Publication (KOKAI) Heisei No. 7-138586). The contents of the above publications are expressly incorporated herein by reference in their entirety.

In the above publications, carbonic acid ester compounds are proposed as lubricants. For reasons such as the fact that carbonic acid ester compounds have low melting points and the carbonic acid ester moiety contributes to resistance to hydrolysis, they are known to exhibit good lubricating properties in magnetic recording media.

However, as the result of examination conducted by the present inventors, the followings were found with carbonic acid ester-based lubricants that are widely employed in conventional magnetic recording media:

(1) The carbonic acid ester group is of low polarity, tending not to conform to metals. Thus, the film strength is weak when applied as a lubricant film to the surface of a metal.

(2) In particulate magnetic recording media, compounds of high polarity, such as polyurethane and vinyl chloride resins are generally employed. Additionally, in the above carbonic acid ester lubricants, hydrophobic compounds such as long-chain alkyls are employed, resulting in poor compatibility with binder. When the quantity of a lubricant with poor compatibility is increased, there is a concern that crystallization will end up occurring on the surface of the magnetic layer, and when running is temporarily stopped while in a state of contact with the head member, there is concern that the lubricant will gradually bleed out onto the surface of the medium while running is stopped, resulting in the head member adhering to the medium surface when running is resumed and thus generating considerable startup friction (running durability decreases).

SUMMARY OF THE INVENTION

An aspect of the present invention provides for a lubricant composition that can provide an excellent lubricating effect in various applications such as magnetic recording media.

The present inventors conducted extensive research into achieving the above lubricant composition, resulting in the discovery that a polyether compound comprising an alkylene oxide residue and a carbonic acid ester residue conformed well to metals, thereby permitting the formation of a lubricant film of high strength on metal surfaces. Research conducted by the present inventors further revealed that among such polyether compounds, some compounds had good compatibility with the binders employed in magnetic recording media.

The present inventors devised the present invention based on results derived from the above discoveries.

An aspect of the present invention relates to a lubricant composition comprising a polyether compound comprising an alkylene oxide residue and a carbonic acid ester residue.

The alkylene oxide residue may comprise at least one selected from the group consisting of an ethylene oxide residue, propylene oxide residue, polyethylene oxide residue, and polypropylene oxide residue.

The polyether compound may comprise a polyether compound denoted by general formula (I) and/or a polyether compound denoted by general formula (II):

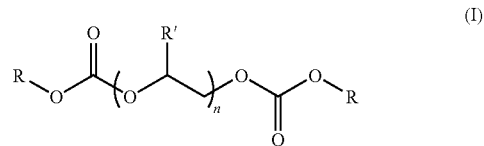

(I)

wherein, in general formula (I), R denotes a linear or branched alkyl group, R' denotes a hydrogen atom or a methyl group, and n denotes an integer of equal to or greater than 1 but equal to or lower than 100;

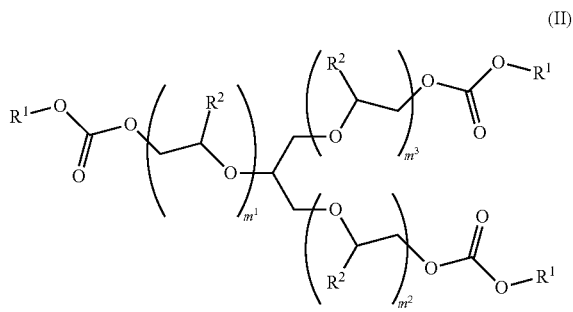

(II)

wherein, in general formula (II), $R^1$ denotes a linear or branched alkyl group, $R^2$ denotes a hydrogen atom or a methyl group, and each of $m^1$, $m^2$, and $m^3$ independently denotes an integer of equal to or greater than 1 but equal to or lower than 100.

The polyether compound denoted by general formula (I) may be a polyether compound denoted by general formula (1);

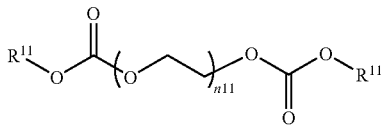

wherein, in general formula (1), $R^{11}$ denotes a linear or branched alkyl group with 1 to 12 carbon atoms, and n11 denotes an integer of equal to or greater than 2 but equal to or lower than 100.

The polyether compound denoted by general formula (I) may be a polyether compound denoted by general formula (2);

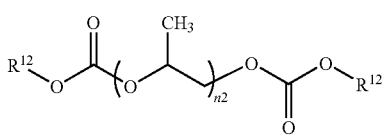

wherein, in general formula (2), $R^{12}$ denotes a linear or branched alkyl group with 1 to 8 carbon atoms, and n2 denotes an integer of equal to or greater than 2 but equal to or lower than 100.

The polyether compound denoted by general formula (II) may be a polyether compound denoted by general formula (3);

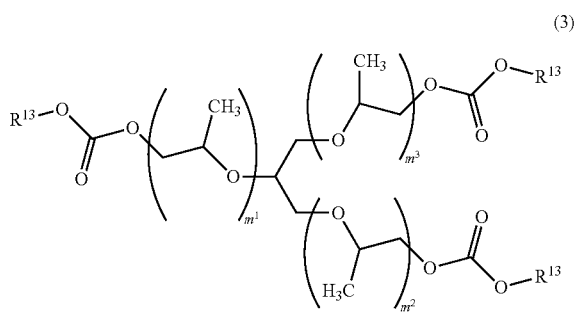

wherein, in general formula (3), $R^{13}$ denotes a linear or branched alkyl group with 1 to 8 carbon atoms, and each of $m^1$, $m^2$, and $m^3$ independently denotes an integer of equal to or greater than 1 but equal to or lower than 100.

The lubricant composition of the present invention can be employed for the preparation of a lubricant film for metal surface.

The lubricant composition of the present invention can also be employed as a friction reducing agent.

A further aspect of the present invention relates to a magnetic recording medium comprising a layer comprising the lubricant composition of the present invention.

The above magnetic recording medium may comprise a magnetic layer comprising a ferromagnetic powder and a binder on a nonmagnetic support, in which the layer comprising the lubricant composition is the magnetic layer, and the lubricant composition comprises at least one polyether compound selected from the group consisting of polyether compounds denoted by the above general formulas (1) to (3).

The above magnetic recording medium may comprise a nonmagnetic layer comprising a nonmagnetic powder and a binder and a magnetic layer comprising a ferromagnetic powder and a binder in this order on a nonmagnetic support, in which the layer comprising the lubricant composition is the nonmagnetic layer, and the lubricant composition comprises at least one polyether compound selected from the group consisting of polyether compounds denoted by the above general formulas (1) to (3). In this Example, the magnetic layer may be comprise at least one polyether compound selected from the group consisting of polyether compounds denoted by the above general formulas (1) to (3).

The layer comprising the above lubricant composition, such as the magnetic layer or the nonmagnetic layer, may further comprise a fatty acid and/or a fatty acid amide.

A still further aspect of the present invention relates to a polyether compound denoted by the above general formula (I), that may be a polyether compound denoted by the above general formula (1) or (2).

A still further aspect of the present invention relates to a polyether compound denoted by the above general formula (II), that may be a polyether compound denoted by the above general formula (3).

The present invention can provide a lubricant composition that is useful for reducing friction on metal surfaces, enhancing abrasion resistance, reducing the friction on magnetic recording media, and the like, as well as a novel polyether compound. The present invention can further provide a magnetic recording medium having excellent running durability.

Other exemplary embodiments and advantages of the present invention may be ascertained by reviewing the present disclosure.

DETAILED DESCRIPTION OF THE EMBODIMENTS

Unless otherwise stated, a reference to a compound or component includes the compound or component by itself, as well as in combination with other compounds or components, such as mixtures of compounds.

As used herein, the singular forms "a," "an," and "the" include the plural reference unless the context clearly dictates otherwise.

Except where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not to be considered as an attempt to limit the application of the doctrine of equivalents to the scope of the claims, each numerical parameter should be construed in light of the number of significant digits and ordinary rounding conventions.

Additionally, the recitation of numerical ranges within this specification is considered to be a disclosure of all numerical values and ranges within that range. For example, if a range is from about 1 to about 50, it is deemed to include, for example, 1, 7, 34, 46.1, 23.7, or any other value or range within the range.

The following preferred specific embodiments are, therefore, to be construed as merely illustrative, and non-limiting to the remainder of the disclosure in any way whatsoever. In this regard, no attempt is made to show structural details of the present invention in more detail than is necessary for fundamental understanding of the present invention; the description taken with the drawings making apparent to those skilled in the art how several forms of the present invention may be embodied in practice.

Lubricant Composition

The lubricant composition of the present invention comprises a polyether compound having an alkylene oxide residue and a carbonic acid ester residue. In addition to a carbonic acid ester residue, the polyether compound comprises an alkylene oxide residue. Thus, it comprises many more ether sites than the carbonic acid ester-based lubricants that have been conventionally employed. Thus, there is good affinity with metals and a strong lubricant film can be formed on metal surfaces. Thus, not only does this contribute to a reduction in friction during sliding between metal members, but an abrasion-reducing effect is also achieved.

Still further, among the above polyether compounds, the polyether compounds denoted by general formulas (1) to (3) further below are highly compatible with the binders generally employed in magnetic recording media. This is attributed to the following: since alkylene oxide residues contribute to compatibility, and the chain length of terminal alkyl groups is relatively short, the major contribution to compatibility made by alkylene oxide residues is not greatly compromised by the terminal alkyl groups. As set forth above, lubricants having poor compatibility with binder present the concern that bleeding occurring when running is stopped will produce a high startup friction when running is resumed. However, with a lubricant having good compatibility with binder, the above increase in startup friction can be inhibited, yielding a magnetic recording medium having good running durability. Further, a lubricant having good compatibility with binder can be added in larger quantities than the conventionally employed carbonic acid ester-based lubricants. Thus, a larger quantity can be added to enhance lubricating properties in magnetic recording media with layers that have been thinned for high-density recording. Similarly, polyethylene glycol and polypropylene glycol are compounds that have alkylene oxide residues. For example, Japanese Patent No. 2,608,604 describes the addition of polyethylene glycol as an emulsifying agent to an aqueous emulsion/suspension of a tire-curing bladder-use lubricant composition. However, polyethylene glycol and polypropylene glycol have terminal hydroxyl groups, and thus react with the polyisocyanate employed as a curing agent in particulate magnetic recording media, potentially compromising the curing property. Accordingly, polyethylene glycol and polypropylene glycol are unsuitable as components of particulate magnetic recording media. By contrast, the polyether compound of the present invention has a terminal carbonic acid ester group that reacts poorly with polyisocyanate, and thus can produce the desired effect without affecting the curing property in particulate magnetic recording media.

As set forth above, the above-described lubricant composition comprising a polyether compound can reduce friction on metal surfaces, increase resistance to abrasion, and enhance the running durability of particulate magnetic recording media.

The lubricant composition of the present invention will be described in greater detail below.

The alkylene oxide residue in the present invention is one that comprises a unit structure denoted by [—Y—O—] (where Y denotes an alkylene group) with a number of repetitions of equal to or more than 1. The number of repetitions is equal to or more than 1. Considering the ease of obtaining starting materials, the repetition number is preferably equal to or less than 100. The alkylene group denoted by Y may be linear or may have a branched chain. The alkylene group has, for example, 1 to 5, desirably 1 to 3, and preferably, 2 or 3 carbon atoms. From the perspectives of the lubricating effect, compatibility with binder, and the ease of obtaining starting materials, the alkylene oxide residue is desirably an ethylene oxide residue, propylene oxide residue, polyethylene oxide residue, or polypropylene oxide residue.

The polyether compound comprises at least one alkylene oxide residue and at least one carbonic acid ester residue. These two residues may be bonded through a linking group, but from the perspective of the lubricating effect, a carbonic acid ester group is desirably present on the end of the alkylene oxide chain. Examples of desirable embodiments of such polyether compounds are the polyether compounds denoted by general formula (I) and the polyether compound denoted by general formula (II) below.

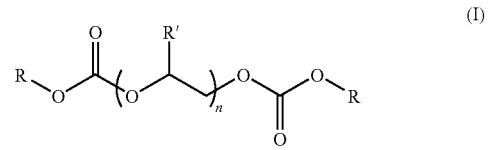
(I)

In general formula (I), R denotes a linear or branched alkyl group, R' denotes a hydrogen atom or a methyl group, and n denotes an integer of equal to or greater than 1 but equal to or lower than 100.

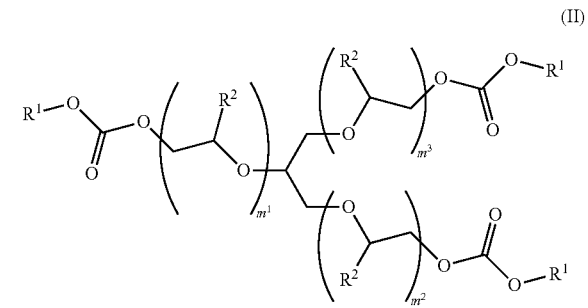
(II)

In general formula (II), $R^1$ denotes a linear or branched alkyl group, $R^2$ denotes a hydrogen atom or a methyl group, and each of $m^1$, $m^2$, and $m^3$ independently denotes an integer of equal to or greater than 1 but equal to or lower than 100.

The compounds denoted by general formulas (I) and (II) will be described below.

In general formula (I), R denotes a linear or branched alkyl group. From the perspective of lubrication, a linear alkyl group with 1 to 50 carbon atoms is desirable and one with 1 to 25 carbon atoms is preferred. As set forth further below, from the perspective of compatibility with binder, a linear alkyl group with 1 to 12 carbon atoms is desirable, and one with 3 to 12 carbon atoms is preferred. Specific examples of linear alkyl groups are butyl groups, hexyl groups, octyl groups, decyl groups, dodecyl groups, tetradecyl groups, and hexadecyl groups.

To achieve good resistance to hydrolysis, the alkyl group denoted by R is desirably a branched alkyl group. From the perspective of lubrication, a branched alkyl group with 1 to 50 carbon atoms is desirable, one with 1 to 25 carbon atoms is preferred, and one with 3 to 8 carbon atoms is of greater preference. From the perspective of compatibility with binder, a branched alkyl group with 1 to 12 carbon atoms is desirable and one with 3 to 12 carbon atoms is preferred. Specific examples of branched alkyl groups are tert-butyl groups, tert-amyl groups, isopropyl groups, isobutyl groups, isopropyl groups, 1,1-dimethylbutyl groups, 1-methylbutyl groups, 1,3-dimethylbutyl groups, 1-methylpropyl groups, 1,1,2-trimethylpropylbutyl groups, 1-ethyl-1-methylpropyl groups, 2-methylpropyl groups, 2-methylbutyl groups, and 2-ethylhexyl groups.

The branched structure in the branched alkyl group may be located at either the α-position or β-position. However, from the perspective of achieving good running durability, the branched structure is desirably located at the β-position.

The alkyl group denoted by R may comprise a substituent on a side chain. Examples of the substituent are halogen atoms (such as a fluorine atom or chlorine atom). In the present invention, the number of carbon atoms of a given group is the number of carbon atoms of the portion excluding substituents when substituents are present on the group.

In general formula (I), R' denotes a hydrogen atom or a methyl group. When employing a starting material in the form of polyethylene glycol, R becomes a hydrogen atom. In the case of polypropylene glycol, R' becomes a methyl group.

In general formula (I), n denotes an integer of equal to or greater than 1 but equal to or lower than 100. Polyether compounds in which n in general formula (I) is an integer falling within the range of 1 to 100 have good affinity for metals and permit the formation of lubricating films of good hardness on metal surfaces. The hydrophilic property increases in polyethers containing carbonate bonds that are obtained with an n exceeding 100, chlorine ions generated during the reaction tend to be picked up, and it becomes difficult to manufacture a product of high purity. Thus, n in general formula (I) is an integer that does not exceed 100. The effect achieved by increasing the ether moieties becomes impossible when n is 0, so n is an integer of equal to or greater than 1. From the perspectives of compatibility with binder, n is desirably an integer falling within a range of 2 to 100, preferably an integer falling within a range of 2 to 70, and more preferably, an integer falling within a range of 2 to 50. In general formula (I), when n denotes an integer equal to or greater than 2, the multiple instances of R' that are present may be identical or different. From the perspective of facilitating synthesis, they are desirably identical. Similarly, the two instances of R that are present in general formula (I) may be identical or different, but are desirably identical from the perspective of facilitating synthesis.

From the perspective of lubrication, the average molecular weight of the polyether compound denoted by general formula (I) desirably falls within a range of 100 to 5,000. From the perspective of volatility, it desirably falls within a range of 200 to 5,000. In the present invention, the average molecular weight refers to the weight average molecular weight.

Among the polyether compounds denoted by general formula (I), the polyether compounds denoted by general formula (1) below and the polyether compounds denoted by general formula (2) below are examples of compounds with good compatibility with binder that are suitable as lubricants for particulate magnetic recording media.

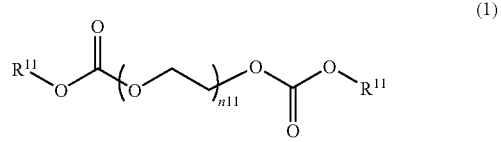

In general formula (1), $R^{11}$ denotes a linear or branched alkyl group with 1 to 12 carbon atoms, desirably a linear or branched alkyl group with 3 to 12 carbon atoms.

In general formula (1), n11 denotes an integer of equal to or greater than 2 but equal to or lower than 100, desirably an integer of equal to or greater than 2 but equal to or lower than 70, and preferably an integer of equal to or greater than 2 but equal to or lower than 50.

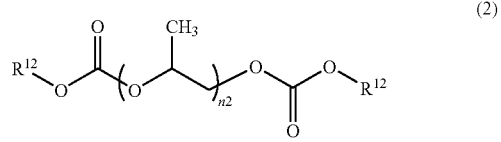

In general formula (2), $R^{12}$ denotes a linear or branched alkyl group with 1 to 8 carbon atoms, desirably a linear or branched alkyl group with 3 to 8 carbon atoms.

In general formula (2), n2 denotes an integer of equal to or greater than 2 but equal to or lower than 100, desirably an integer of equal to or greater than 2 but equal to or lower than 70, and preferably an integer of equal to or greater than 2 but equal to or lower than 50.

Specific examples of polyether compounds denoted by general formula (I) are given below. However, the present invention is not limited to the specific examples set forth below. Among the Example Compounds given below, (I-1), (I-3), (I-5), and (I-7) are Example Compounds corresponding to general formula (1), and (I-2), (I-4), and (I-6) are Example Compounds corresponding to general formula (2).

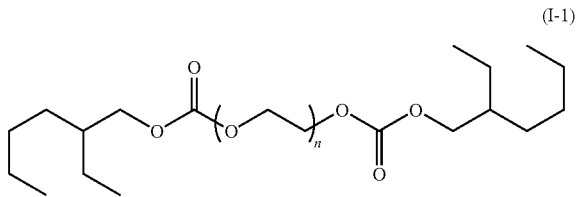

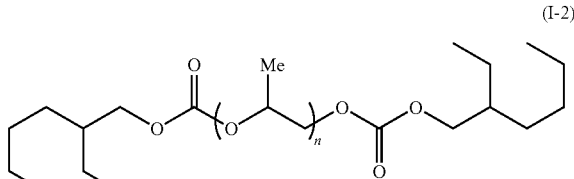

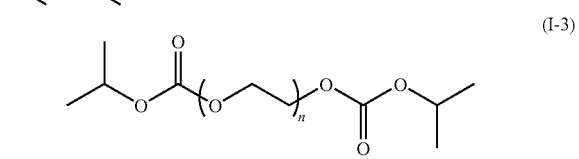

-continued

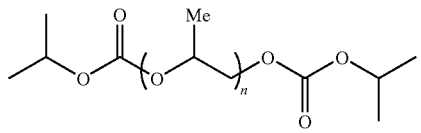
(I-4)

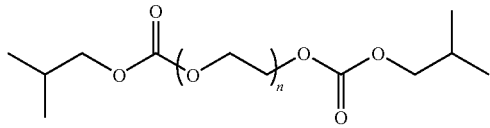
(I-5)

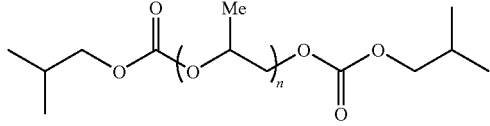
(I-6)

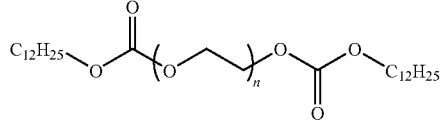
(I-7)

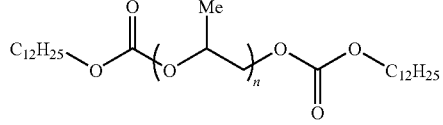
(I-8)

In general formula (II), $R^1$ denotes a linear or branched alkyl group. The details are identical to those for R in general formula (I).

In general formula (II), $R^2$ denotes a hydrogen atom or a methyl group. When employing polyethylene glycol as starting material, $R^2$ becomes a hydrogen atom, and when employing polypropylene glycol, $R^2$ becomes a methyl group. In general formula (II), the multiple instances of $R^2$ that are present may be identical or different. From the perspective of facilitating synthesis, they are desirably identical. Similarly, the three instances of $R^1$ that are present in general formula (II) may be identical or different. From the perspective of facilitating synthesis, they are desirably identical.

In general formula (II), each of $m^1$, $m^2$, and $m^3$ independently denotes an integer of equal to or greater than 1 but equal to or lower than 100. In polyether compounds in which $m^1$, $m^2$, and $m^3$ in general formula (II) denote integers ranging from 1 to 100, good performance is achieved in terms of affinity for metals and compatibility with binder. When $m^1$, $m^2$, and $m^3$ exceed 100, the hydrophilic property of the carbonate bond-containing polyether that is obtained increases, chlorine ions generated during the reaction tend to be picked up, and it becomes difficult to manufacture a product of high purity. Thus, $m^1$, $m^2$, and $m^3$ in general formula (I) are integers that do not exceed 100. When $m^1$, $m^2$, and $m^3$ are 0, it becomes impossible to achieve an adequate effect by increasing the ether moieties. Thus, $m^1$, $m^2$, and $m^3$ denote integers of equal to or greater than 1. From the perspective of compatibility with binder, $m^1$, $m^2$, and $m^3$ desirably denote integers ranging from 2 to 100, preferably integers ranging from 2 to 30, and more preferably, integers ranging from 2 to 25.

From the perspective of lubrication, the (weight) average molecular weight of the polyether compound denoted by general formula (II) desirably ranges from 100 to 5,000, and from the perspective of volatility, preferably ranges from 200 to 5,000.

Among the polyether compounds denoted by general formula (II), the polyether compounds denoted by general formula (3) below are examples of compounds that are highly compatible with binder and are suitable as lubricants for particulate magnetic recording media.

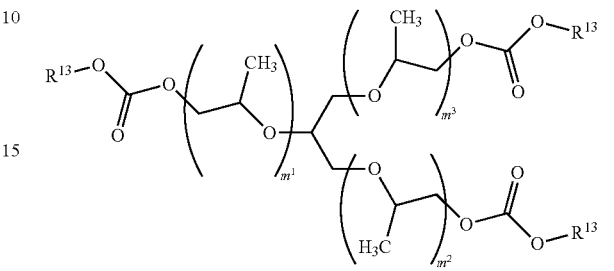
(3)

In general formula (3), $R^{13}$ denotes a linear or branched alkyl group with 1 to 8 carbon atoms, desirably a linear or branched alkyl group with 3 to 8 carbon atoms.

In general formula (3), each of $m^1$, $m^2$, and $m^3$ independently denotes an integer of equal to or greater than 1 but equal to or lower than 100, desirably an integer of equal to or greater than 1 but equal to or lower than 30, an integer of equal to or greater than 1 but equal to or lower than 25.

Specific examples of polyether compounds denoted by general formula (II) are given below. However, the present invention is not limited to the specific examples given below. Among the Example Compounds given below, (II-2), (II-4), and (II-6) are Example Compounds corresponding to general formula (3).

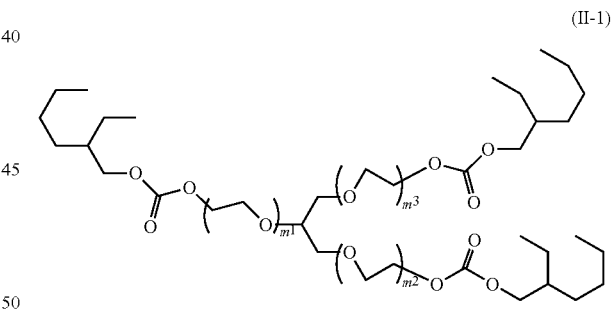
(II-1)

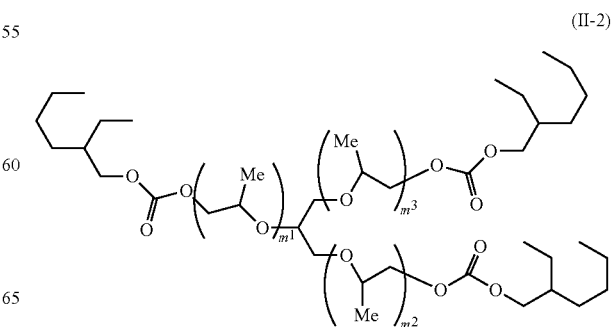
(II-2)

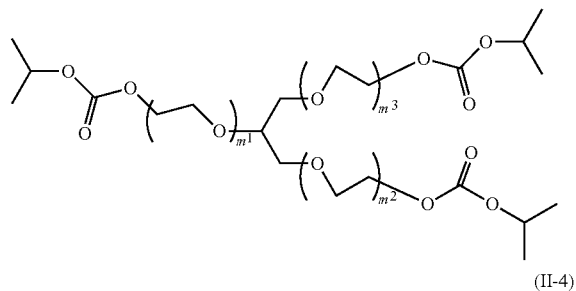
(II-3)
(II-4)

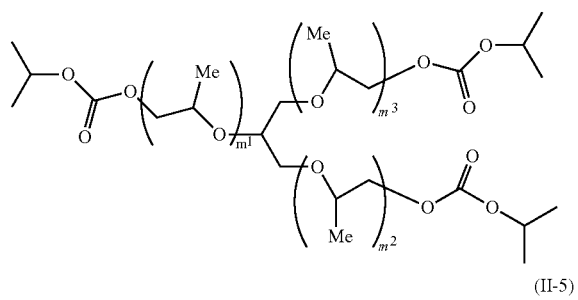
(II-5)
(II-6)

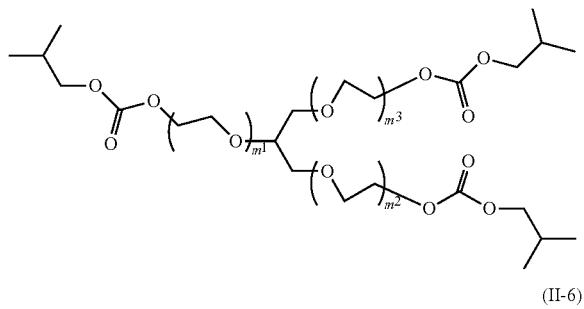
(II-7)

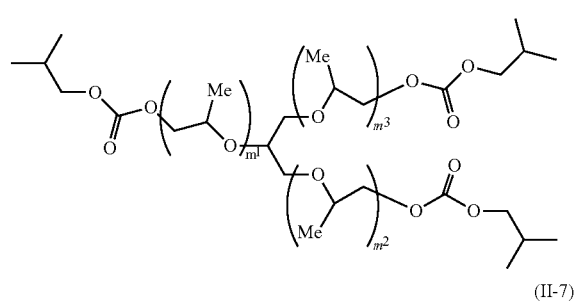
(II-8)

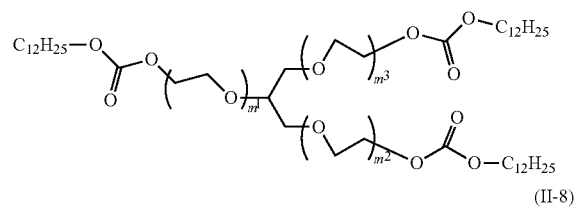

The polyether compound comprising an alkylene oxide residue and a carbonic acid ester residue that is contained in the lubricant composition of the present invention can be readily synthesized by known methods, and is available as a commercial product.

The polyether compounds denoted by general formulas (I) and (II) (and the polyether compounds denoted by general formulas (1), (2), and (3)) can be readily obtained by introducing a carbonate group to the terminal of polyethylene glycol (PEG) or polypropylene glycol (PPG). n in general formula (I) and $m^1$, $m^2$, and $m^3$ in general formula (II) are generally determined based on the degree of polymerization of the starting material PEG or PPG. For the polyether compounds denoted by general formulas (I) and (II), the starting materials PEG and PPG are inexpensive and are readily available as products of differing degrees of polymerization. Thus, compounds with desired values of n in general formula (I) and $m^1$, $m^2$, and $m^3$ in general formula (II) can be readily synthesized. This is extremely advantageous in practical terms. The method of reacting polyethylene glycol or polypropylene glycol with chloroformic acid ester is suitable as a method for synthesizing the polyether compounds denoted by general formulas (I) and (II). Reference can be made in Examples set forth further below for details of the synthesis conditions. Synthesis starting materials such as PEG, PPG, and chloroformic acid ester can be synthesized by known methods, and are readily available as commercial products. The fact that the target compound has been obtained can be confirmed by a known identification method such as NMR.

The lubricant composition of the present invention can contain one or more polyether compounds comprising an alkylene oxide residue and a carbonic acid ester residue. It can be comprised of the polyether compound alone, or, as needed, may be mixed with known additives such as surfactants, extreme pressure agents, viscosity-raising agents, and viscosity-lowering agents to obtain a lubricating film for metal surfaces or a friction-reducing agent for metal surfaces.

That is, the present invention can also provide a lubricating film for metal surfaces comprised of the lubricant composition of the present invention, and to a friction-reducing agent for metal surfaces comprised of the lubricant composition of the present invention. In this context, the term "metal surfaces" refers to surfaces containing metal components, and includes, for example, surfaces comprised of metal oxides.

The content of the polyether compound comprising an alkylene oxide residue and a carbonic acid ester residue in the lubricant composition, lubricant film for metal surfaces and friction-reducing agent for metal surfaces of the present invention is, for example, 1 to 100 weight percent, preferably 60 to 100 weight percent.

The lubricant composition of the present invention can produce excellent effects as a lubricant in various applications. In particular, it is suitable as a lubricant for magnetic recording media. This is because it has good affinity with metal, allowing it to function as a lubricant film when coated on the surface of the magnetic layer of a thin-film magnetic recording medium. Among such lubricants, the lubricant composition of the present invention comprising a polyether compound denoted by any of general formulas (1) to (3) is highly compatible with binder, and is thus suitable as a lubricant in particulate magnetic recording media. For example, for application to thin-film magnetic recording media, the polyether compound comprising an alkylene oxide residue and a carbonic acid ester residue can be dissolved in a suitable solvent as needed, and then used to impregnate the magnetic layer or coated or misted onto the surface of the magnetic layer. For application to a particulate magnetic recording medium, it suffices to mix it into the magnetic layer coating liquid or nonmagnetic layer coating liquid. The details are as set forth further below.

In addition to the above-described lubricant for particulate and thin-film magnetic recording media, the lubricant composition of the present invention can be employed as a synthetic lubricant such as a lubricant for precision machinery, a lubricant for various polymers, and a lubricant for cosmetics and the like.

In the embodiment of the lubricant composition of the present invention that is applied as a lubricating film for metal surfaces, the thickness of the lubricating film is not specifically limited. The thickness can be optimally set based on the application. Since the lubricating film for metal surfaces comprises a polyether compound comprising an alkylene oxide residue and a carbonic acid ester residue, it has good affinity with metals, yields strong films, and can thus function as a protective film. The quantity of the friction-reducing agent for metal surfaces that is employed can also be optimally set based on the application so as to yield desired friction characteristics. Further, the lubricating film for metal surfaces and the friction-reducing agent for metal surfaces of the present invention can be applied to various metal surfaces, such as SUJ2, SUS, aluminum oxide, titanium oxide, and iron oxide.

Magnetic Recording Medium

The present invention further relates to a magnetic recording medium comprising a layer comprising the lubricant composition of the present invention, and can be thin-film magnetic recording media and particulate magnetic recording media. The magnetic recording medium of the present invention in the form of a particulate magnetic recording medium can include two embodiments as described below. That is, the first embodiment is a magnetic recording medium comprising a magnetic layer comprising a ferromagnetic powder and a binder on a nonmagnetic support, in which the layer comprising the lubricant composition is the magnetic layer, and the lubricant composition comprises at least one polyether compound selected from the group consisting of polyether compounds denoted by general formulas (1) to (3). The second embodiment is a magnetic recording medium comprising a nonmagnetic layer comprising a nonmagnetic powder and a binder and a magnetic layer comprising a ferromagnetic powder and a binder in this order on a nonmagnetic support, in which the layer comprising the lubricant composition is the nonmagnetic layer, and the lubricant composition comprises at least one polyether compound selected from the group consisting of polyether compounds denoted by general formulas (1) to (3). The second embodiment of the magnetic recording medium can also contain at least one polyether compound denoted by any one of general formulas (1) to (3) in the magnetic layer.

The first and second embodiments of the magnetic recording medium are collectively referred to as the magnetic recording medium of the present invention below.

The content of the polyether compound in the magnetic layer of the magnetic recording medium of the present invention is, for example, 0.1 to 10 weight parts, desirably 0.3 to 6 weight parts, and preferably, 0.5 to 3 weight parts per 100 weight parts of ferromagnetic powder.

Incorporating the polyether compound into the nonmagnetic layer can control the quantity of polyether compound in the nonmagnetic layer that gradually migrates to the magnetic layer side and bleeds out onto the surface during running and storage. This is advantageous in terms of achieving good running durability and maintaining storage properties. In this case, for example, polyether compounds of differing boiling points and polarities can be employed in the nonmagnetic layer and magnetic layer to control bleeding out onto the surface, the quantity of surfactant can be adjusted to enhance coating stability, a large quantity of the polyether compound can be added to the nonmagnetic layer, and the like to control the quantity of the polyether compound that is present on the surface of the magnetic layer during running and storage. The content of the polyether compound in the nonmagnetic layer is, for example, 0.01 to 10 weight parts, desirably 0.05 to 6 weight parts, and preferably, 0.1 to 3 weight parts per 100 weight parts of nonmagnetic powder.

A single polyether compound can be employed in both the magnetic layer and nonmagnetic layer, or two or more polyether compounds can be mixed for use. Use in combination with other lubricants is also possible. Since the polyether compound is highly compatible with the binders that are commonly employed in magnetic recording media, it can be used to enhance the lubricating effect when used in combination with lubricant components that generate precipitates on the surface due to inadequate compatibility when the quantity that is added of these other lubricants is increased. As stated above, when running is temporarily stopped in a state of contact with the head member and then resumed, an increase in startup friction will be observed for lubricants with poor compatibility with binder. However, in the magnetic recording medium of the present invention, which comprises a polyether compound that is highly compatible with binder, good running durability can be maintained without the occurrence of increased startup friction when running is resumed.

Magnetic Layer

The magnetic layer in the magnetic recording medium of the present invention will be described below.

Ferromagnetic metal powder and hexagonal ferrite powder can be employed as the ferromagnetic powder in the magnetic layer. These will be described in detail below. However, the ferromagnetic powder employed in the present invention is not limited to ferromagnetic metal powders and hexagonal ferrite powders. For example, iron nitride powder or the like can also be employed.

(i) Ferromagnetic Metal Powder

The ferromagnetic metal powder employed in the magnetic layer is not specifically limited. A ferromagnetic metal powder comprised chiefly of $\alpha$-Fe is desirably employed. The ferromagnetic powder may, in addition to prescribed atoms, further comprise atoms such as Al, Si, S, Sc, Ca, Ti, V, Cr, Cu, Y, Mo, Rh, Pd, Ag, Sn, Sb, Te, Ba, Ta, W, Re, Au, Hg, Pb, Bi, La, Ce, Pr, Nd, P, Co, Mn, Zn, Ni, Sr, and B. In particular, it is desirable to incorporate at least one from among Al, Si, Ca, Y, Ba, La, Nd, Co, Ni, and B in addition to $\alpha$-Fe, and, preferably, to incorporate at least one from among Co, Y, and Al. The content of Co is desirably equal to or greater than 0 atom percent and equal to or lower than 40 atom percent, preferably equal to or greater than 15 atom percent and equal to or lower than 35 atom percent, and more preferably, equal to or greater than 20 atom percent and equal to or lower than 35 atom percent, relative to Fe. The content of Y is desirably equal to or greater than 1.5 atom percent and equal to or lower than 12 atom percent, preferably equal to or greater than 3 atom percent and equal to or lower than 10 atom percent, and more preferably, equal to or greater than 4 atom percent and equal to or lower than 9 atom percent. The content of Al is desirably equal to or greater than 1.5 atom percent and equal to or lower than 12 atom percent, preferably equal to or greater than 3 atom percent and equal to or lower than 10 atom percent, and more preferably, equal to or greater than 4 atom percent and equal to or lower than 9 atom percent.

These ferromagnetic metal powders may be pretreated prior to dispersion with dispersing agents, lubricants, surfactants, antistatic agents, and the like, described further below. Specific examples are described in Japanese Examined Patent Publication (KOKOKU) Showa Nos. 44-14090, 45-18372, 47-22062, 47-22513, 46-28466, 46-38755, 47-4286, 47-12422, 47-17284, 47-18509, 47-18573, 39-10307, and 46-39639; and U.S. Pat. Nos. 3,026,215, 3,031,341, 3,100, 194, 3,242,005, and 3,389,014, which are expressly incorporated herein by reference in their entirety.

The ferromagnetic metal powder may contain a small quantity of hydroxide or oxide. Ferromagnetic metal powders obtained by known manufacturing methods may be employed. The following are examples of methods of manufacturing ferromagnetic metal powders: methods of reduction with compound organic acid salts (chiefly oxalates) and reducing gases such as hydrogen; methods of reducing iron oxide with a reducing gas such as hydrogen to obtain Fe or Fe—Co particles or the like; methods of thermal decomposition of metal carbonyl compounds; methods of reduction by addition of a reducing agent such as sodium boron hydride, hypophosphite, or hydrazine to an aqueous solution of ferromagnetic metal; and methods of obtaining powder by vaporizing a metal in a low-pressure inert gas. Any one from among the known method of slow oxidation, that is, immersing the ferromagnetic metal powder thus obtained in an organic solvent and drying it; the method of immersing the ferromagnetic metal powder in an organic solvent, feeding in an oxygen-containing gas to form a surface oxide film, and then conducting drying; and the method of adjusting the partial pressures of oxygen gas and an inert gas without employing an organic solvent to form a surface oxide film, may be employed.

The specific surface area by BET method of the ferromagnetic metal powder employed in the magnetic layer is preferably 45 to 100 $m^2/g$, more preferably 50 to 80 $m^2/g$. At 45 $m^2/g$ and above, low noise is achieved. At 100 $m^2/g$ and below, good surface properties are achieved. The crystallite size of the ferromagnetic metal powder is preferably 80 to 180 Angstroms, more preferably 100 to 180 Angstroms, and still more preferably, 110 to 175 Angstroms. The major axis length of the ferromagnetic metal powder is preferably equal to or greater than 0.01 μm and equal to or less than 0.15 μm, more preferably equal to or greater than 0.02 μm and equal to or less than 0.15 μm, and still more preferably, equal to or greater than 0.03 μm and equal to or less than 0.12 μm. The acicular ratio of the ferromagnetic metal powder is preferably equal to or greater than 3 and equal to or less than 15, more preferably equal to or greater than 5 and equal to or less than 12. The us of the ferromagnetic metal powder is preferably 100 to 180 A·$m^2$/kg, more preferably 110 to 170 A·$m^2$/kg, and still more preferably, 125 to 160 A·$m^2$/kg. The coercivity of the ferromagnetic metal powder is preferably 2,000 to 3,500 Oe (160 to 280 kA/m), more preferably 2,200 to 3,000 Oe (176 to 240 kA/m).

The moisture content of the ferromagnetic metal powder is desirably 0.01 to 2 weight percent. The moisture content of the ferromagnetic metal powder is desirably optimized based on the type of binder. The pH of the ferromagnetic metal powder is desirably optimized depending on what is combined with the binder. A range of 4 to 12 can be established, with 6 to 10 being preferred. As needed, the ferromagnetic metal powder can be surface treated with Al, Si, P, or an oxide thereof. The quantity can be set to 0.1 to 10 weight percent of the ferromagnetic metal powder. When applying a surface treatment, the quantity of a lubricant such as a fatty acid that is adsorbed is desirably not greater than 100 mg/$m^2$. The ferromagnetic metal powder will sometimes contain inorganic ions such as soluble Na, Ca, Fe, Ni, or Sr. These are desirably substantially not present, but seldom affect characteristics at equal to or less than 200 ppm. The ferromagnetic metal powder employed in the present invention desirably has few voids; the level is preferably equal to or less than 20 volume percent, more preferably equal to or less than 5 volume percent. As stated above, so long as the particle size characteristics are satisfied, the ferromagnetic metal powder may be acicular, rice grain-shaped, or spindle-shaped. The SFD of the ferromagnetic metal powder itself is desirably low, with equal to or less than 0.8 being preferred. The Hc distribution of the ferromagnetic metal powder is desirably kept low. When the SFD is equal to or lower than 0.8, good electromagnetic characteristics are achieved, output is high, and magnetic inversion is sharp, with little peak shifting, in a manner suited to high-density digital magnetic recording. To keep the Hc low, the methods of improving the particle size distribution of goethite in the ferromagnetic metal powder and preventing sintering may be employed.

(ii) Hexagonal Ferrite Powder

Examples of hexagonal ferrite powders are barium ferrite, strontium ferrite, lead ferrite, calcium ferrite, and various substitution products thereof such as Co substitution products. Specific examples are magnetoplumbite-type barium ferrite and strontium ferrite; magnetoplumbite-type ferrite in which the particle surfaces are covered with spinels; and magnetoplumbite-type barium ferrite, strontium ferrite, and the like partly comprising a spinel phase. The following may be incorporated into the hexagonal ferrite powder in addition to the prescribed atoms: Al, Si, S, Sc, Ti, V, Cr, Cu, Y, Mo, Rh, Pd, Ag, Sn, Sb, Te, Ba, Ta, W, Re, Au, Hg, Pb, Bi, La, Ce, Pr, Nd, P, Co, Mn, Zn, Ni, Sr, B, Ge, Nb and the like. Compounds to which elements such as Co—Zn, Co—Ti, Co—Ti—Zr, Co—Ti—Zn, Ni—Ti—Zn, Nb—Zn—Co, Sb—Zn—Co, and Nb—Zn have been added may generally also be employed. They may comprise specific impurities depending on the starting materials and manufacturing methods employed.

When the length of the signal recording region approaches the size of the magnetic material contained in the magnetic layer, it becomes impossible to create a distinct magnetization transition state, essentially precluding recording. Thus, the shorter the recording wavelength becomes, the smaller the magnetic material should be. In the present invention, to achieve good recording in the short-wavelength region, the use of hexagonal ferrite powder having an average plate diameter falling within a range of 10 to 40 nm is preferable, a range of 15 to 30 nm is more preferable, and a range of 20 to 25 nm is of still greater preference.

An average plate ratio [arithmetic average of (plate diameter/plate thickness)] of the hexagonal ferrite preferably ranges from 1 to 15, more preferably 1 to 7. When the average plate diameter ranges from 1 to 15, adequate orientation can be achieved while maintaining high filling property in the magnetic layer, as well as increased noise due to stacking between particles can be suppressed. The specific surface area by BET method ($S_{BET}$) within the above particle size range is preferably equal to or higher than 40 $m^2/g$, more preferably 40 to 200 $m^2/g$, and particularly preferably, 60 to 100 $m^2/g$.

Narrow distributions of particle plate diameter and plate thickness of the hexagonal ferrite powder are normally good. About 500 particles can be randomly measured in, a transmission electron microscope (TEM) photograph of particles to measure the particle plate diameter and plate thickness. The distributions of particle plate diameter and plate thickness are often not a normal distribution. However, when expressed as the standard deviation to the average size, σ/average size can be 0.1 to 1.0. In general, the particle producing reaction system is rendered as uniform as possible and the particles produced are subjected to a distribution-enhancing treatment to achieve a narrow particle size distribution. For example, methods such as selectively dissolving ultrafine particles in an acid solution by dissolution are known.

A coercivity (Hc) of the hexagonal ferrite powder of about 143.3 to 318.5 kA/m (1800 to 4,000 Oe) can normally be achieved. The coercivity (He) of the hexagonal ferrite powder preferably ranges from 159.2 to 238.9 kA/m (2,000 to 3,000 Oe), more preferably 191.0 to 214.9 kA/m (2,200 to 2,800 Oe).

The coercivity (Hc) can be controlled by particle size (plate diameter and plate thickness), the types and quantities of elements contained, substitution sites of the element, the particle producing reaction conditions, and the like.

The saturation magnetization ($\sigma_s$) of the hexagonal ferrite powder preferably ranges from 30 to 80 A·m$^2$/kg (30 to 80 emu/g). The higher saturation magnetization ($\sigma_s$) is preferred, however, it tends to decrease with decreasing particle size. Known methods of improving saturation magnetization ($\sigma_s$) are combining spinel ferrite with magnetoplumbite ferrite, selection of the type and quantity of elements incorporated, and the like. It is also possible to employ W-type hexagonal ferrite. When dispersing the magnetic material, the particle surface of the magnetic material can be processed with a substance suited to a dispersion medium and a polymer. Both organic and inorganic compounds can be employed as surface treatment agents. Examples of the principal compounds are oxides and hydroxides of Si, Al, P, and the like; various silane coupling agents; and various titanium coupling agents. The quantity of surface treatment agent added range from, for example, 0.1 to 10 mass percent relative to the mass of the magnetic material. The pH of the magnetic material is also important to dispersion. A pH of about 4 to 12 is usually optimum for the dispersion medium and polymer. From the perspective of the chemical stability and storage properties of the medium, a pH of about 6 to 11 can be selected. Moisture contained in the magnetic material also affects dispersion. There is an optimum level for the dispersion medium and polymer, usually selected from the range of 0.01 to 2.0 percent.

Methods of manufacturing the hexagonal ferrite powder include: (1) a vitrified crystallization method consisting of mixing into a desired ferrite composition barium oxide, iron oxide, and a metal oxide substituting for iron with a glass forming substance such as boron oxide; melting the mixture; rapidly cooling the mixture to obtain an amorphous material; reheating the amorphous material; and refining and comminuting the product to obtain a barium ferrite crystal powder; (2) a hydrothermal reaction method consisting of neutralizing a barium ferrite composition metal salt solution with an alkali; removing the by-product; heating the liquid phase to equal to or greater than 100° C.; and washing, drying, and comminuting the product to obtain barium ferrite crystal powder; and (3) a coprecipitation method consisting of neutralizing a barium ferrite composition metal salt solution with an alkali; removing the by-product; drying the product and processing it at equal to or less than 1,100° C.; and comminuting the product to obtain barium ferrite crystal powder. Any manufacturing method can be selected in the present invention. As needed, the hexagonal ferrite powder can be surface treated with Al, Si, P, or an oxide thereof. The quantity is set to, for example, 0.1 to 10 mass percent of the ferromagnetic powder. When applying a surface treatment, the quantity of a lubricant such as a fatty acid that is adsorbed is desirably not greater than 100 mg/m$^2$. The ferromagnetic powder will sometimes contain inorganic ions such as soluble Na, Ca, Fe, Ni, or Sr. These are desirably substantially not present, but seldom affect characteristics at equal to or less than 200 ppm.

Known techniques regarding binders, lubricants, dispersion agents, additives, solvents, dispersion methods and the like for magnetic layer, nonmagnetic layer and backcoat layer can be suitably applied. In particular, known techniques regarding the quantity and types of binders, and quantity added and types of additives and dispersion agents can be applied.

Conventionally known thermoplastic resins, thermosetting resins, reactive resins, and mixtures of the same can be employed as the binder. A thermoplastic resin having a glass transition temperature of −100 to 150° C., a number average molecular weight of 1,000 to 200,000, desirably 10,000 to 100,000, and a degree of polymerization of about 50 to 1,000 can be employed.

Examples thereof are polymers and copolymers comprising structural units in the form of vinyl chloride, vinyl acetate, vinyl alcohol, maleic acid, acrylic acid, acrylic acid esters, vinylidene chloride, acrylonitrile, methacrylic acid, methacrylic acid esters, styrene, butadiene, ethylene, vinyl butyral, vinyl acetal, and vinyl ether; polyurethane resins; and various rubber resins. Further, examples of thermosetting resins and reactive resins are phenol resins, epoxy resins, polyurethane cured resins, urea resins, melamine resins, alkyd resins, acrylic reactive resins, formaldehyde resins, silicone resins, epoxy polyamide resins, mixtures of polyester resins and isocyanate prepolymers, mixtures of polyester polyols and polyisocyanates, and mixtures of polyurethane and polyisocyanates. These resins are described in detail in *Handbook of Plastics* published by Asakura Shoten, which is expressly incorporated herein by reference in its entirety. It is also possible to employ known electron beam-cured resins in each layer. Examples and manufacturing methods of such resins are described in Japanese Unexamined Patent Publication (KOKAI) Showa No. 62-256219. The contents of the above publications are expressly incorporated herein by reference in their entirety. The above-listed resins may be used singly or in combination. Preferred resins are combinations of polyurethane resin and at least one member selected from the group consisting of vinyl chloride resin, vinyl chloride-vinyl acetate copolymers, vinyl chloride-vinyl acetate-vinyl alcohol copolymers, and vinyl chloride-vinyl acetate-maleic anhydride copolymers, as well as combinations of the same with polyisocyanate. Among these, vinyl chloride binder and polyurethane binder are preferred.

As the polyurethane, polyester-urethane, polyether-urethane, polycarbonate-urethane, polyetherester-urethane, acrylic polyurethane can be employed. The above binders can have high compatibility with the above-described polyether compound to control the surface lubricant quantity to an optimal range. The polar groups that may be incorporated in the binder are preferably sulfonate, sulfamate, sulfobetain, phosphate, phosphonate and the like. The content of the polar group that may be incorporated in the binder preferably ranges from $1\times10^5$ eq/g to $2\times10^{-4}$ eq/g. The above-described binders can be synthesized by known methods, or can be obtained by incorporating a suitable amount of polar groups into a commercial product.

Polyurethane can be employed as a binder with vinyl chloride resin. However, when a small amount of dechlorination causes head corrosion, it is also possible to employ polyurethane alone, or employ polyurethane and isocyanate alone. When polyurethane is employed, a glass transition temperature of −50 to 150° C., preferably 0 to 100° C., an elongation at break of 100 to 2,000 percent, a stress at break of 0.05 to 10 kg/mm$^2$ (approximately 0.49 to 98 MPa), and a yield point of 0.05 to 10 kg/mm$^2$ (approximately 0.49 to 98 MPa) are desirable.

Examples of polyisocyanates are tolylene diisocyanate, 4,4'-diphenylmethane diisocyanate, hexamethylene diisocyanate, xylylene diisocyanate, napthylene-1,5-diisocyanate, o-toluidine diisocyanate, isophorone diisocyanate, triphenylmethane triisocyanate, and other isocyanates; products of these isocyanates and polyalcohols; polyisocyanates produced by condensation of isocyanates; and the like. These isocyanates are commercially available under the following trade names, for example: Coronate L, Coronate HL, Coronate 2030, Coronate 2031, Millionate MR and Millionate MTL manufactured by Nippon Polyurethane Industry Co. Ltd.; Takenate D-102, Takenate D-110N, Takenate D-200 and Takenate D-202 manufactured by Takeda Chemical Industries Co., Ltd.; and Desmodule L, Desmodule IL, Desmodule N and Desmodule HL manufactured by Sumitomo Bayer Co., Ltd. They can be used in each layer singly or in combinations of two or more by exploiting differences in curing reactivity.

The quantity of binder in the magnetic layer is preferably 10 to 25 weight parts per 100 weight parts of ferromagnetic powder, including curing agent. When the magnetic recording medium of the present invention comprises a nonmagnetic layer between the magnetic layer and the nonmagnetic support, the quantity of binder in the nonmagnetic layer is preferably greater than that in the magnetic layer. Specifically, the quantity of binder in the nonmagnetic layer is preferably 25 to 40 weight parts per 100 weight parts of nonmagnetic powder.

Additives may be added as needed to the magnetic layer and nonmagnetic layer. Examples of these additives are abrasives, lubricants, dispersing agents, dispersion adjuvants, mildew-preventing agents, antistatic agents, oxidation inhibitors, solvents, and carbon black. The lubricant components indicated below, for example, may be employed in addition to the above-described polyether compounds as lubricants in the magnetic layer and nonmagnetic layer. Fatty acids such as stearic acid and fatty acid amides such as stearic acid amides are suitable as additional lubricant components to lower the coefficient of friction and prevent sticking. The quantity of additional lubricant components employed is desirably 0.5 to 3.5 weight parts, preferably 0.5 to 1.5 weight parts, per 100 weight parts of ferromagnetic powder or nonmagnetic powder. When the above polyether compound is employed in combination with a fatty acid to achieve good lubrication performance by employing an additional lubricant, the quantity of fatty acid employed is desirably 0.3 to 1.5 weight parts per 100 weight parts of ferromagnetic powder or nonmagnetic powder employed. Fatty acid amides have relatively high melting points and tend to bleed out onto the surface of the magnetic layer. The bleeding out of a large quantity of fatty acid amide may compromise storage properties, cause material to adhere to the head, and the like. By contrast, fatty acids generally have the property of readily adsorbing to the surface of powder and function to inhibit the bleeding out of fatty acid amides. Accordingly, when employing a fatty acid amide in combination with the above-described polyether compound, it is desirable to additionally employ a fatty acid. When these three components, polyether compound, fatty acid, and fatty acid amide, are employed in combination, the synergistic effect of the three components can yield good lubricating performance while inhibiting the bleeding out of a large amount of fatty acid amide. When employing these three components in combination, the quantity of fatty acid amide employed is desirably 5 to 20 weight percent, preferably 14.2 to 20 weight percent, of the total quantity of the three components combined.

Examples of additives are: molybdenum disulfide, tungsten disulfide, graphite, boron nitride, graphite fluoride, silicone oil, polar group-comprising silicone, fatty acid-modified silicone, fluorosilicone, fluoroalcohols, fluoroesters, polyolefin, polyglycol, polyphenyl ether, phenyl phosphonic acid, benzyl phosphonic acid, phenethyl phosphonic acid, α-methylbenzylphosphonic acid, 1-methyl-1-phenethylphosphonic acid, diphenylmethylphosphonic acid, biphenylphosphonic acid, benzylphenylphosphonic acid, α-cumylphosphonic acid, toluoylphosphonic acid, xylylphosphonic acid, ethylphenylphosphonic acid, cumenylphosphonic acid, propylphenylphosphonic acid, butylphenylphosphonic acid, heptylphenylphosphonic acid, octylphenylphosphonic acid, nonylphenylphosphonic acid, other aromatic ring-comprising organic phosphonic acids, alkali metal salts thereof, octylphosphonic acid, 2-ethylhexylphosphonic acid, isooctylphosphonic acid, isononylphosphonic acid, isodecylphosphonic acid, isoundecylphosphonic acid, isododecylphosphonic acid, isohexadecylphosphonic acid, isooctadecylphosphonic acid, isoeicosylphosphonic acid, other alkyl phosphonoic acid, alkali metal salts thereof, phenyl phosphoric acid, benzyl phosphoric acid, phenethyl phosphoric acid, α-methylbenzylphosphoric acid, 1-methyl-1-phenethylphosphoric acid, diphenylmethylphosphoric acid, diphenyl phosphoric acid, benzylphenyl phosphoric acid, α-cumyl phosphoric acid, toluoyl phosphoric acid, xylyl phosphoric acid, ethylphenyl phosphoric acid, cumenyl phosphoric acid, propylphenyl phosphoric acid, butylphenyl phosphoric acid, heptylphenyl phosphoric acid, octylphenyl phosphoric acid, nonylphenyl phosphoric acid, other aromatic phosphoric esters, alkali metal salts thereof, octyl phosphoric acid, 2-ethylhexylphosphoric acid, isooctyl phosphoric acid, isononyl phosphoric acid, isodecyl phosphoric acid, isoundecyl phosphoric acid, isododecyl phosphoric acid, isohexadecyl phosphoric acid, isooctyldecyl phosphoric acid, isoeicosyl phosphoric acid, other alkyl ester phosphoric acids, alkali metal salts thereof, alkylsulfonic acid ester, alkali metal salts thereof, fluorine-containing alkyl sulfuric acid esters, alkali metal salts thereof, lauric acid, myristic acid, palmitic acid, stearic acid, behenic acid, butyl stearate, oleic acid, linolic acid, linoleic acid, elaidic acid, erucic acid, other monobasic fatty acids comprising 10 to 24 carbon atoms (which may contain an unsaturated bond or be branched), metal salts thereof, butyl stearate, octyl stearate, amyl stearate, isooctyl stearate, octyl myristate, butyl laurate, butoxyethyl stearate, anhydrosorbitan monostearate, anhydrosorbitan tristearate, other monofatty esters, difatty esters, or polyfatty esters comprising a monobasic fatty acid having 10 to 24 carbon atoms (which may contain an unsaturated bond or be branched) and any one from among a monohydric, dihydric, trihydric, tetrahydric, pentahydric or hexahydric alcohol having 2 to 22 carbon atoms (which may contain an unsaturated bond or be branched), alkoxyalcohol having 12 to 22 carbon atoms (which may contain an unsaturated bond or be branched) or a monoalkyl ether of an alkylene oxide polymer, fatty acid amides with 2 to 22 carbon atoms, and aliphatic amines with 8 to 22 carbon atoms. Compounds having aralkyl groups, aryl groups, or alkyl groups substituted with groups other than hydrocarbon groups, such as nitro groups, F, Cl, Br, $CF_3$, $CCl_3$, $CBr_3$, and other halogen-containing hydrocarbons in addition to the above hydrocarbon groups, may also be employed.

Examples of additives are: molybdenum disulfide, tungsten disulfide, graphite, boron nitride, graphite fluoride, silicone oils, silicone with polar groups, fatty acid-modified silicone, fluorine-comprising silicone, fluorine-comprising alcohol, fluorine-comprising esters, polyolefins, polyglycols, polyphenyl ethers, phenyl phosphonate, benzyl phosphonate, phenethyl phosphonate, α-methylbenzyl phosphonate, 1-methyl-1-phenethyl phosphonate, diphenylmethyl phosphonate, biphenyl phosphonate, benzylphenyl phosphonate, α-cumyl phosphonate, toluoyl phosphonate, xylyl phosphonate, ethylphenyl phosphonate, cumenyl phosphonate, propylphenyl phosphonate, butylphenyl phosphonate, heptylphenyl phosphonate, octylphenyl phosphonate, nonylphenyl phosphonate, and other aromatic ring-containing organic phosphonic acids and their alkali metal salts; octyl phosphonate, 2-ethylhexyl phosphonate, isooctyl phosphonate, isononyl phosphonate, isodecyl phosphonate, isoundecyl phosphonate, isododecyl phosphonate, isohexadecyl phosphonate, isooctadecyl phosphonate, isoeicosyl phosphonate, and other alkyl phosphonates and their alkali metal salts; phenyl phosphate, benzyl phosphate, phenethyl phosphate, α-methylbenzyl phosphate, 1-methyl-1-phenethyl phosphate, diphenylmethyl phosphate, biphenyl phosphate, benzylphenyl phosphate, α-cumyl phosphate, toluoyl phosphate, xylyl phosphate, ethylphenyl phosphate, cumenyl phosphate, propylphenyl phosphate, butylphenyl phosphate, heptylphenyl phosphate, octylphenyl phosphate, nonylphenyl phosphate, and other aromatic phosphoric acid esters and their alkali metal salts; octyl phosphate, 2-ethylhexyl phosphate, isooctyl phosphate, isononyl phosphate, isodecyl phosphate, isoundecyl phosphate, isododecyl phosphate, isohexadecyl phosphate, isooctadecyl phosphate, isoeicosyl phosphate, and other alkyl phosphoric acid esters and their alkali metal salts; alkyl sulfonic acid esters and their alkali metal salts; fluorine-containing alkyl sulfuric acid esters and their alkali metal salts; lauric acid, myristic acid, palmitic acid, stearic acid, behenic acid, butyl stearate, oleic acid, linolic acid, linoleic acid, elaidic acid, erucic acid, and other optionally branched monobasic fatty acids having 10 to 24 carbon atoms and optionally comprising unsaturated bonds, and metal salts thereof; monofatty acid esters comprised of one butyl stearate, octyl stearate, amyl stearate, isooctyl stearate, octyl myristate, butyl laurate, butoxyethyl stearate, anhydrosorbitan monostearate, anhydrosorbitan tristearate, or some other optionally branched monobasic fatty acid having 10 to 24 carbon atoms and optionally comprising an unsaturated bond, one monohydric to hexahydric optionally branched alcohol having 2 to 22 carbon atoms and optionally comprising an unsaturated bond, and one alkoxy alcohol or alkylene oxide polymer monoalkyl ether having 12 to 22 carbon atoms and optionally comprising an unsaturated bond; difatty acid esters or polyhydric fatty acid esters; lauric acid amide; myristic acid amide; palmitic acid amide; stearic acid amide; isostearic acid amide; oleic acid amide; linolic acid amide; linoleic acid amide; eicosic acid amide; elaidic acid amide; behenic acid amide; N-methylmyristic acid amide; N-ethylmyristic acid amide; N,N-dimethylstearic acid amide; and N,N-diethylstearic acid amide. Of these, fatty acid amides having 2 to 22 carbon atoms, such as myristic acid amide, palmitic acid amide, and stearic acid amide; fatty acid amines having 8 to 22 carbon atoms; and the like can be employed. Compounds having aralkyl groups, aryl groups, or alkyl groups substituted with groups other than hydrocarbon groups, such as nitro groups, F, Cl, Br, $CF_3$, $CCl_3$, $CBr_3$, and other halogen-containing hydrocarbons in addition to the above hydrocarbon groups, may also be employed.

It is also possible to employ nonionic surfactants such as alkylene oxide-based surfactants, glycerin-based surfactants, glycidol-based surfactants and alkylphenolethylene oxide adducts; cationic surfactants such as cyclic amines, ester amides, quaternary ammonium salts, hydantoin derivatives, heterocycles, phosphoniums, and sulfoniums; anionic surfactants comprising acid groups, such as carboxylic acid, sulfonic acid, phosphoric acid, sulfuric ester groups, and phosphoric ester groups; and ampholytic surfactants such as amino acids, amino sulfonic acids, sulfuric or phosphoric esters of amino alcohols, and alkyl betaines. Details of these surfactants are described in *A Guide to Surfactants* (published by Sangyo Tosho K.K.), which is expressly incorporated herein by reference in its entirety.

These lubricants, antistatic agents and the like need not be 100 percent pure and may contain impurities, such as isomers, unreacted material, by-products, decomposition products, and oxides in addition to the main components. These impurities are preferably comprised equal to or less than 30 weight percent, and more preferably equal to or less than 10 weight percent.

Carbon black may be added to the magnetic layer as needed. Examples of types of carbon black that are suitable for use in the magnetic layer are: furnace black for rubber, thermal for rubber, black for coloring, and acetylene black. These may be used singly or in combination of two or more. It is preferable that the specific surface area is 5 to 500 $m^2/g$, the DBP oil absorption capacity is 10 to 400 ml/100 g, the particle diameter is 5 to 300 nm, the pH is 2 to 10, the moisture content is 0.1 to 10 percent, and the tap density is 0.1 to 1 g/ml. When employing carbon black, the quantity preferably ranges from 0.1 to 30 weight percent with respect to the weight of the magnetic material. In the magnetic layer, carbon black can work to prevent static, reduce the coefficient of friction, impart light-blocking properties, enhance film strength, and the like; the properties vary with the type of carbon black employed. Accordingly, the type, quantity, and combination of carbon blacks employed in the present invention may be determined separately for the magnetic layer and the nonmagnetic layer based on the objective and the various characteristics stated above, such as particle size, oil absorption capacity, electrical conductivity, and pH, and be optimized for each layer. For example, the *Carbon Black Handbook* compiled by the Carbon Black Association, which is expressly incorporated herein by reference in its entirety, may be consulted for types of carbon black suitable for use in the magnetic layer.

Known materials chiefly having a Mohs' hardness of equal to or greater than 6 may be employed either singly or in combination as abrasives. These include: α-alumina with an α-conversion rate of equal to or greater than 90 percent, β-alumina, silicon carbide, chromium oxide, cerium oxide, α-iron oxide, corundum, synthetic diamond, silicon nitride, titanium carbide, titanium oxide, silicon dioxide, and boron nitride. Complexes of these abrasives (obtained by surface treating one abrasive with another) may also be employed. There are cases in which compounds or elements other than the primary compound are contained in these abrasives; the effect does not change so long as the content of the primary compound is equal to or greater than 90 percent. The particle size of the abrasive is preferably 0.01 to 2 micrometers. To enhance electromagnetic characteristics, a narrow particle size distribution is desirable. Abrasives of differing particle size may be incorporated as needed to improve durability; the same effect can be achieved with a single abrasive as with a wide particle size distribution. It is preferable that the tap density is 0.3 to 2 g/cc, the moisture content is 0.1 to 5 percent, the pH is 2 to 11, and the specific surface area is 1 to 30 m²/g. The shape of the abrasive employed may be acicular, spherical, cubic, plate-shaped or the like. However, a shape comprising an angular portion is desirable due to high abrasiveness. These abrasives may be added as needed to the nonmagnetic layer. Addition of abrasives to the nonmagnetic layer can be done to control surface shape, control how the abrasive protrudes, and the like. The particle size and quantity of the abrasives added to the magnetic layer and nonmagnetic layer should be set to optimal values.

Known organic solvents can be used in any ratio. Examples are ketones such as acetone, methyl ethyl ketone, methyl isobutyl ketone, diisobutyl ketone, cyclohexanone, isophorone, and tetrahydrofuran; alcohols such as methanol, ethanol, propanol, butanol, isobutyl alcohol, isopropyl alcohol, and methylcyclohexanol; esters such as methyl acetate, butyl acetate, isobutyl acetate, isopropyl acetate, ethyl lactate, and glycol acetate; glycol ethers such as glycol dimethyl ether, glycol monoethyl ether, and dioxane; aromatic hydrocarbons such as benzene, toluene, xylene, cresol, and chlorobenzene; chlorinated hydrocarbons such as methylene chloride, ethylene chloride, carbon tetrachloride, chloroform, ethylene chlorohydrin, and dichlorobenzene; N,N-dimethylformamide; and hexane.

Nonmagnetic Layer

Details of the nonmagnetic layer will be described below. The magnetic recording medium of the present invention, according to the second embodiment, comprises a nonmagnetic layer comprising a nonmagnetic powder and a binder between the nonmagnetic support and the magnetic layer. Both organic and inorganic substances may be employed as the nonmagnetic powder in the nonmagnetic layer. Carbon black may also be employed. Examples of inorganic substances are metals, metal oxides, metal carbonates, metal sulfates, metal nitrides, metal carbides, and metal sulfides.

Specifically, titanium oxides such as titanium dioxide, cerium oxide, tin oxide, tungsten oxide, ZnO, $ZrO_2$, $SiO_2$, $Cr_2O_3$, α-alumina with an α-conversion rate of 90 to 100 percent, β-alumina, γ-alumina, α-iron oxide, goethite, corundum, silicon nitride, titanium carbide, magnesium oxide, boron nitride, molybdenum disulfide, copper oxide, $MgCO_3$, $CaCO_3$, $BaCO_3$, $SrCO_3$, $BaSO_4$, silicon carbide, and titanium carbide may be employed singly or in combinations of two or more. α-iron oxide and titanium oxide are preferred.

The nonmagnetic powder may be acicular, spherical, polyhedral, or plate-shaped. The crystallite size of the nonmagnetic powder preferably ranges from 4 nm to 500 nm, more preferably from 40 to 100 nm. A crystallite size falling within a range of 4 nm to 500 nm is desirable in that it facilitates dispersion and imparts a suitable surface roughness. The average particle diameter of the nonmagnetic powder preferably ranges from 5 nm to 500 nm. As needed, nonmagnetic powders of differing average particle diameter may be combined; the same effect may be achieved by broadening the average particle distribution of a single nonmagnetic powder. The preferred average particle diameter of the nonmagnetic powder ranges from 10 to 200 nm. Within a range of 5 nm to 500 nm, dispersion is good and good surface roughness can be achieved.

The specific surface area of the nonmagnetic powder preferably ranges from 1 to 150 m²/g, more preferably from 20 to 120 m²/g, and further preferably from 50 to 100 m²/g. Within the specific surface area ranging from 1 to 150 m²/g, suitable surface roughness can be achieved and dispersion is possible with the desired quantity of binder. Oil absorption capacity using dibutyl phthalate (DBP) preferably ranges from 5 to 100 mL/100 g, more preferably from 10 to 80 mL/100 g, and further preferably from 20 to 60 mL/100 g. The specific gravity ranges from, for example, 1 to 12, preferably from 3 to 6. The tap density ranges from, for example, 0.05 to 2 g/mL, preferably from 0.2 to 1.5 g/mL. A tap density falling within a range of 0.05 to 2 g/mL can reduce the amount of scattering particles, thereby facilitating handling, and tends to prevent solidification to the device. The pH of the nonmagnetic powder preferably ranges from 2 to 11, more preferably from 6 to 9. When the pH falls within a range of 2 to 11, the coefficient of friction does not become high at high temperature or high humidity or due to the freeing of fatty acids. The moisture content of the nonmagnetic powder ranges from, for example, 0.1 to 5 weight percent, preferably from 0.2 to 3 weight percent, and more preferably from 0.3 to 1.5 weight percent. A moisture content falling within a range of 0.1 to 5 weight percent is desirable because it can produce good dispersion and yield a stable coating viscosity following dispersion. An ignition loss of equal to or less than 20 weight percent is desirable and nonmagnetic powders with low ignition losses are desirable.

When the nonmagnetic powder is an inorganic powder, the Mohs' hardness is preferably 4 to 10. Durability can be ensured if the Mohs' hardness ranges from 4 to 10. The stearic acid (SA) adsorption capacity of the nonmagnetic powder preferably ranges from 1 to 20 μmol/m², more preferably from 2 to 15 μmol/m². The heat of wetting in 25° C. water of the nonmagnetic powder is preferably within a range of 200 to 600 erg/cm² (approximately 200 to 600 mJ/m²). A solvent with a heat of wetting within this range may also be employed. The quantity of water molecules on the surface at 100 to 400° C. suitably ranges from 1 to 10 pieces per 100 Angstroms. The pH of the isoelectric point in water preferably ranges from 3 to 9. The surface of these nonmagnetic powders is preferably treated with $Al_2O_3$, $SiO_2$, $TiO_2$, $ZrO_2$, $SnO_2$, $Sb_2O_3$, and ZnO. The surface-treating agents of preference with regard to dispersibility are $Al_2O_3$, $SiO_2$, $TiO_2$, and $ZrO_2$, and $Al_2O_3$, $SiO_2$ and $ZrO_2$ are further preferable. They may be employed singly or in combination. Depending on the objective, a surface-treatment coating layer with a coprecipitated material may also be employed, the coating structure which comprises a first alumina coating and a second silica coating thereover or the reverse structure thereof may also be adopted. Depending on the objective, the surface-treatment coating layer may be a porous layer, with homogeneity and density being generally desirable.

Specific examples of nonmagnetic powders suitable for use in the nonmagnetic layer in the present invention are: Nanotite from Showa Denko K. K.; HIT-100 and ZA-G1 from Sumitomo Chemical Co., Ltd.; DPN-250, DPN-250BX, DPN-245, DPN-270BX, DPN-550BX and DPN-550RX from Toda Kogyo Corp.; titanium oxide TTO-51B, TTO-55A, TTO-55B, TTO-55C, TTO-55S, TTO-55D, SN-100, MJ-7, α-iron oxide E270, E271 and E300 from Ishihara Sangyo Co., Ltd.; STT-4D, STT-30D, STT-30 and STT-65C from Titan Kogyo K. K.; MT-100S, MT-100T, MT-150W, MT-500B, MT-600B, MT-100F and MT-500HD from Tayca Corporation; FINEX-25, BF-1, BF-10, BF-20 and ST-M from Sakai Chemical Industry Co., Ltd.; DEFIC-Y and DEFIC-R from Dowa Mining Co., Ltd.; AS2BM and TiO2P25 from Nippon Aerogil; 100A and 500A from Ube Industries, Ltd.; Y-LOP from Titan Kogyo K. K.; and sintered products of the same. Particular preferable nonmagnetic powders are titanium dioxide and α-iron oxide.

Carbon black may be combined with nonmagnetic powder in the nonmagnetic layer to reduce surface resistivity, reduce light transmittance, and achieve a desired micro-Vickers hardness. The micro-Vickers hardness of the nonmagnetic layer is normally 25 to 60 kg/mm² (approximately 245 to 588 MPa), desirably 30 to 50 kg/mm² (approximately 294 to 490 MPa) to adjust head contact. It can be measured with a thin film hardness meter (HMA-400 made by NEC Corporation) using a diamond triangular needle with a tip radius of 0.1 micrometer and an edge angle of 80 degrees as indenter tip. "Techniques for evaluating thin-film mechanical characteristics," Realize Corp., for details. The content of the above publication is expressly incorporated herein by reference in its entirety. The light transmittance is generally standardized to an infrared absorbance at a wavelength of about 900 nm equal to or less than 3 percent. For example, in VHS magnetic tapes, it has been standardized to equal to or less than 0.8 percent. To this end, furnace black for rubber, thermal black for rubber, black for coloring, acetylene black and the like may be employed.

The specific surface area of the carbon black employed in the nonmagnetic layer is, for example, 100 to 500 m²/g, preferably 150 to 400 m²/g. The DBP oil absorption capability is, for example, 20 to 400 mL/100 g, preferably 30 to 200 mL/100 g. The particle diameter of the carbon black is, for example, 5 to 80 nm, preferably 10 to 50 nm, and more preferably, 10 to 40 nm. It is preferable that the pH of the carbon black is 2 to 10, the moisture content is 0.1 to 10 percent, and the tap density is 0.1 to 1 g/mL. The carbon black employed may be surface-treated with a dispersant or grafted with resin, or have a partially graphite-treated surface. The carbon black may be dispersed in advance into the binder prior to addition to the nonmagnetic coating liquid. These carbon blacks may be used singly or in combination. When employing carbon black, the quantity of the carbon black is preferably within a range not exceeding 50 weight percent of the inorganic powder as well as not exceeding 40 weight percent of the total weight of the nonmagnetic layer. For example, the *Carbon Black Handbook* compiled by the Carbon Black Association, which is expressly incorporated herein by reference in its entirety, may be consulted for types of carbon black suitable for use in the nonmagnetic layer.

Based on the objective, an organic powder may be added to the nonmagnetic layer. Examples of such an organic powder are acrylic styrene resin powders, benzoguanamine resin powders, melamine resin powders, and phthalocyanine pigments. Polyolefin resin powders, polyester resin powders, polyamide resin powders, polyimide resin powders, and polyfluoroethylene resins may also be employed. The manufacturing methods described in Japanese Unexamined Patent Publication (KOKAI) Showa Nos. 62-18564 and 60-255827 may be employed. The contents of the above applications are expressly incorporated herein by reference in their entirety.

Binders, lubricants, dispersing agents, additives, solvents, dispersion methods, and the like suited to the magnetic layer may be adopted to the nonmagnetic layer. In particular, known techniques for the quantity and type of binder and the quantity and type of additives and dispersion agents employed in the magnetic layer may be adopted thereto.

All of the additives employed in the present invention are readily available as commercial products. All or some part of these additives can be added during any step in the preparation of the coating liquid for the magnetic layer or nonmagnetic layer. For example, there are cases where they are mixed with ferromagnetic powder prior to the kneading step; cases where they are added during the step of kneading ferromagnetic powder, binder, and solvent; cases where they are added in the dispersing step; cases where they are added following dispersion; and cases where they are added immediately prior to coating.

Nonmagnetic Support

A known film in the form of a polyester such as polyethylene terephthalate or polyethylene naphthalate, polyolefins, cellulose triacetate, polycarbonate, polyamide, polyimide, polyamidoimide, polysulfone, aromatic polyamide, or polybenzooxazole can be employed as the nonmagnetic support. The use of a high-strength support having a glass transition temperature equal to or higher than 100° C., such as polyethylene naphthalate or aramid, is desirable. As needed, laminated supports such as those disclosed in Japanese Unexamined Patent Publication (KOKAI) Heisei No. 3-224127 can be employed to vary the surface roughness of the magnetic surface and the nonmagnetic support surface. The content of the above publication is expressly incorporated herein by reference in its entirety. These supports can be corona discharge treated, plasma treated, treated to facilitate adhesion, heat treated, treated to remove dust, or the like in advance.

Layer Structure

In the magnetic recording medium of the present invention, the thickness of the nonmagnetic support preferably ranges from 3 to 80 μm, more preferably from 3 to 50 μm, further preferably from 3 to 10 μm.

The thickness of the magnetic layer can be optimized based on the saturation magnetization of the head employed, the length of the head gap, and the recording signal band, and is normally 10 to 150 nm, preferably 20 to 120 nm, more preferably 30 to 100 nm, and further preferably 30 to 80 nm. The thickness variation (aσ/δ) in the magnetic layer is preferably within ±50 percent, more preferably within ±30 percent. At least one magnetic layer is sufficient. The magnetic layer may be divided into two or more layers having different magnetic characteristics, and a known configuration relating to multilayered magnetic layer may be applied.

The thickness of the nonmagnetic layer ranges from, for example, 0.1 to 3.0 μm, preferably 0.3 to 2.0 μm, and more preferably 0.5 to 1.5 μm. The nonmagnetic layer of the present invention is effective so long as it is substantially nonmagnetic. For example, it exhibits the effect of the present invention even when it comprises impurities or trace amounts of magnetic material that have been intentionally incorporated, and can be viewed as substantially having the same configuration as the magnetic recording medium of the present invention. The term "substantially nonmagnetic" is used to mean having a residual magnetic flux density in the nonmagnetic layer of equal to or less than 10 mT, or a coercive force Hc of equal to or less than 7.96 kA/m (100 Oe), it being preferable not to have a residual magnetic flux density or coercive force at all.

Backcoat Layer

The magnetic recording medium of the present invention may comprise a backcoat layer on the opposite surface of the nonmagnetic support from the surface on which the magnetic layer is present. The backcoat layer desirably comprises carbon black and inorganic powder. The formula of the magnetic layer or nonmagnetic layer may be applied for binder and various additives. Application of the above-described formula of the nonmagnetic layer is suitable. The thickness of the backcoat layer is desirably equal to or less than 0.9 μm, preferably 0.1 to 0.7 μm. When a backcoat layer is present in the magnetic recording medium of the present invention, a polyether compound comprising an alkylene oxide residue and a carbonic acid ester residue can be contained in the backcoat layer.

Manufacturing Method

The process for manufacturing coating liquids for forming magnetic, nonmagnetic and backcoat layers comprises at least a kneading step, a dispersing step, and a mixing step to be carried out, if necessary, before and/or after the kneading and dispersing steps. Each of the individual steps may be divided into two or more stages. All of the starting materials employed in the present invention, including the ferromagnetic powder, nonmagnetic powder, the polyether compounds described above, binders, carbon black, abrasives, antistatic agents, lubricants, solvents, and the like, may be added at the beginning of, or during, any of the steps. Moreover, the individual starting materials may be divided up and added during two or more steps. For example, polyurethane may be divided up and added in the kneading step, the dispersion step, and the mixing step for viscosity adjustment after dispersion. To achieve the object of the present invention, conventionally known manufacturing techniques may be utilized for some of the steps. A kneader having a strong kneading force, such as an open kneader, continuous kneader, pressure kneader, or extruder is preferably employed in the kneading step. Details of the kneading process are described in Japanese Unexamined Patent Publication (KOKAI) Heisei Nos. 1-106338 and 1-79274. The contents of these applications are incorporated herein by reference in their entirety. Further, glass beads may be employed to disperse the coating liquids for magnetic, nonmagnetic and backcoat layers, with a dispersing medium with a high specific gravity such as zirconia beads, titania beads, and steel beads being suitable for use. The particle diameter and fill ratio of these dispersing media can be optimized for use. A known dispersing device may be employed. In manufacturing coating liquids, dispersion is preferably enhanced by controlling dispersion conditions (such as types and quantities of beads employed in dispersion, peripheral speed, and dispersion period).

When coating a magnetic recording medium of multilayer configuration, both a wet-on-wet method and a wet-on-dry method can be employed. In the wet-on-wet method, a coating liquid for forming a nonmagnetic layer is coated, and while this coating is still wet, a coating liquid for forming a magnetic layer is coated thereover and dried. In the wet-on-dry method, a coating liquid for forming a nonmagnetic layer is coated and dried to form a nonmagnetic layer, and then a coating liquid for forming a magnetic layer is coated on the nonmagnetic layer and dried.

When using the wet-on-wet method, the following methods are desirably employed;

(1) a method in which the nonmagnetic layer is first coated with a coating device commonly employed to coat magnetic coating materials such as a gravure coating, roll coating, blade coating, or extrusion coating device, and the magnetic layer is coated while the nonmagnetic layer is still wet by means of a support pressure extrusion coating device such as is disclosed in Japanese Examined Patent Publication (KOKOKU) Heisei No. 1-46186 and Japanese Unexamined Patent Publication (KOKAI) Showa No. 60-238179 and Japanese Unexamined Patent Publication (KOKAI) Heisei No. 2-265672, which are expressly incorporated herein by reference in their entirety;

(2) a method in which the upper and lower layers are coated nearly simultaneously by a single coating head having two built-in slits for passing coating liquid, such as is disclosed in Japanese Unexamined Patent Publication (KOKAI) Showa No. 63-88080, Japanese Unexamined Patent Publication (KOKAI) Heisei No. 2-17971, and Japanese Unexamined Patent Publication (KOKAI) Heisei No. 2-265672, which are expressly incorporated herein by reference in their entirety; and (3) a method in which the upper and lower layers are coated nearly simultaneously using an extrusion coating apparatus with a backup roller as disclosed in Japanese Unexamined Patent Publication (KOKAI) Heisei No. 2-174965, which is expressly incorporated herein by reference in its entirety. To avoid deteriorating the electromagnetic characteristics or the like of the magnetic recording medium by aggregation of magnetic particles, shear is desirably imparted to the coating liquid in the coating head by a method such as disclosed in Japanese Unexamined Patent Publication (KOKAI) Showa No. 62-95174 or Japanese Unexamined Patent Publication (KOKAI) Heisei No. 1-236968, which are expressly incorporated herein by reference in their entirety. In addition, the viscosity of the coating liquid preferably satisfies the numerical range specified in Japanese Unexamined Patent Publication (KOKAI) Heisei No. 3-8471, which are expressly incorporated herein by reference in its entirety.

Coating of coating liquid for each layer can be carried out with a coating device commonly employed to coat magnetic coating materials such as a gravure coating, roll coating, blade coating, or extrusion coating device.

When the magnetic recording medium of the present invention is a magnetic tape, the coating layer that is formed by applying the magnetic layer coating liquid can be magnetic field orientation processed using cobalt magnets or solenoids on the ferromagnetic powder contained in the coating layer. When it is a disk, an adequately isotropic orientation can be achieved in some products without orientation using an orientation device, but the use of a known random orientation device in which cobalt magnets are alternately arranged diagonally, or alternating fields are applied by solenoids, is desirable. In the case of ferromagnetic metal powder, the term "isotropic orientation" generally refers to a two-dimensional in-plane random orientation, which is desirable, but can refer to a three-dimensional random orientation achieved by imparting a perpendicular component. Further, a known method, such as opposing magnets of opposite poles, can be employed to effect perpendicular orientation, thereby imparting an isotropic magnetic characteristic in the peripheral direction. Perpendicular orientation is particularly desirable when conducting high-density recording. Spin coating can be used to effect peripheral orientation.

The drying position of the coating is desirably controlled by controlling the temperature and flow rate of drying air, and coating speed. A coating speed of 20 m/min to 1,000 m/min and a dry air temperature of equal to or higher than 60° C. are desirable. Suitable predrying can be conducted prior to entry into the magnet zone.

The coated stock material thus obtained can be temporarily wound on a take-up roll, and then unwound from the take-up roll and calendered. Rolls of a heat-resistant plastic such as epoxy, polyimide, polyamide, or polyamidoimide, can be employed as the calender rolls. Processing with metal rolls is also possible. As for the calendaring conditions, the calender roll temperature ranges from, for example, 60 to 100° C., preferably 70 to 100° C., and more preferably 80 to 100° C. The pressure ranges from, for example, 100 to 500 kg/cm (98 to 490 kN/m), preferably 200 to 450 kg/cm (196 to 441 kN/m), and more preferably 300 to 400 kg/cm (294 to 392 kN/m).

The magnetic recording medium obtained can be cut to desired size with a cutter or the like. The cutter is not specifically limited, but desirably comprises multiple sets of a rotating upper blade (male blade) and lower blade (female blade). The slitting speed, engaging depth, peripheral speed ratio of the upper blade (male blade) and lower blade (female blade) (upper blade peripheral speed/lower blade peripheral speed), period of continuous use of slitting blade, and the like are suitably selected.

Physical properties of the nonmagnetic layer and magnetic layer may be varied based on the objective in the magnetic recording medium of the present invention. For example, the modulus of elasticity of the magnetic layer may be increased to improve running durability while simultaneously employing a lower modulus of elasticity than that of the magnetic layer in the nonmagnetic layer to improve the head contact of the magnetic recording medium.

In the magnetic recording medium of the present invention, the surface roughness of the magnetic layer, denoted as the average surface roughness Ra as measured by an atomic force microscope, desirably falls within a range of 1.0 to 4.5 nm. A surface roughness Ra of equal to or lower than 4.5 nm is suitable for high-density recording, and equal to or higher than 1.0 nm can permit stable running. Surface roughness Ra is preferably 1.0 to 4.0 nm, and more preferably, falls within a range of 2.5 to 4.0 nm. Surface roughness Ra can be obtained as the measured value of Ra of a 40 µm square of the surface of the magnetic layer using a Nanoscope IV made by Veeco Japan. Based on research by the present inventors, when conventional carbonic acid ester lubricants are employed in magnetic recording media in which the smoothness of the magnetic layer surface has been increased for high-density recording, sticking may occur when running is resumed, compromising running durability. By contrast, with the polyether compound comprising an alkylene oxide residue and a carbonic acid ester residue, it is possible to control such sticking when running is resumed. The present inventors attribute this to the good compatibility with binder of the polyester compound comprising an alkylene oxide residue and a carbonic acid ester residue.

Polyether Compound

The present invention relates to the polyether compound denoted by general formula (I) and to the polyether compound denoted by general formula (II). The details of the polyether compounds of the present invention are as set forth above. As stated above, the polyether compounds of the present invention contain more ether moieties than conventionally employed carbonic acid ester lubricants. Thus, they have good affinity for metals and can form a strong lubricating film on metal surfaces. This not only contributes to a reduction in friction when metal members slide against each other, but also has the effect of reducing abrasion. Further, of the polyether compounds of the present invention, the polyether compounds denoted by general formulas (1) to (3) are highly compatible with the binders generally employed in magnetic recording media, making it possible to inhibit an increase in the startup friction with the resumption of running. Since the quantity added can be increased to a higher level than is possible with conventionally employed carbonic acid ester lubricants, more lubricant can be added to a magnetic recording medium with layers that have been thinned for high-density recording, permitting better lubrication.

EXAMPLES

The present invention will be described in detail below based on examples. However, the present invention is not limited to the examples. The term "parts" given in Examples are weight parts unless specifically stated otherwise. In Examples, the $^1$H NMR measurement was conducted with heavy DMSO solvent by 400 MHz NMR (AVANCE II-400 made by Bruker).

Further, the number of repeating units of the polyethylene oxide moiety or the polypropylene oxide moiety of polyethers 1 to 43 below was calculated by the following methods.

Polyethers 1 to 16: Calculation based on the proton ratios at 0.85 ppm and 3.51 ppm in the $^1$H NMR charts of Synthesis Examples 1 to 4 and 16.

Polyethers 17 to 19: Calculation based on the proton ratios at 1.25 to 1.30 ppm and 4.82 to 4.91 ppm in the $^1$H NMR chart of Synthesis Example 17.

Polyethers 20 to 22: Calculation based on the proton ratios at 1.08 to 1.18 ppm and 4.82 to 4.91 ppm in the $^1$H NMR chart of Synthesis Example 20.

Polyethers 23 to 25: Calculation based on the proton ratios at 1.12 to 1.15 ppm and 4.82 to 4.90 ppm in the $^1$H NMR chart of Synthesis Example 23.

Polyethers 26 to 28: Calculation based on the proton ratios at 1.11 to 1.44 ppm and 4.82 to 4.91 ppm in the $^1$H NMR chart of Synthesis Example 26 with the premise that the three repeating polypropylene oxide moieties were identical (m1=m2=m3 in general formula (II)).

Polyethers 29 to 31: Calculation based on the proton ratios at 1.09 to 1.14 ppm and 4.82 to 4.91 ppm in the $^1$H NMR chart of Synthesis Example 29 with the premise that the three repeating polypropylene oxide moieties were identical (m1=m2=m3 in general formula (II)).

Polyethers 32 to 34: Calculation based on the proton ratios at 1.23 to 1.30 ppm and 4.82 to 4.91 ppm in the $^1$H NMR chart of Synthesis Example 32 with the premise that the three repeating polypropylene oxide moieties were identical (m1=m2=m3 in general formula (II)).

Polyethers 35 to 40: Calculation based on the proton ratios at 1.10 to 1.20 ppm and 4.81 to 4.91 ppm in the $^1$H NMR chart of Synthesis Example 35 with the premise that the three repeating polypropylene oxide moieties were identical (m1=m2=m3 in general formula (II)).

Polyether 41: Calculation based on the proton ratios at 3.32 to 3.61 ppm and 4.11 ppm in the $^1$H NMR chart of Synthesis Example 41 with the premise that the three repeating propylene oxide moieties were identical (m1=m2=m3 in general formula (II)).

Polyether 42: Calculation based on the proton ratios at 3.33 to 3.70 ppm and 4.26 to 4.28 ppm in the $^1$H NMR chart of Synthesis Example 42 with the premise that the three repeating propylene oxide moieties were identical (m1=m2=m3 in general formula (II)).

Polyether 43: Calculation based on the proton ratios at 3.30 to 3.62 ppm and 4.06 to 4.17 ppm in the $^1$H NMR chart of Synthesis Example 43 with the premise that the three repeating propylene oxide moieties were identical (m1=m2=m3 in general formula (II)).

Synthesis Example 1

One weight part of polyethylene glycol (polyethylene glycol 200 made by Wako Pure Chemical Industries, Ltd.) and 0.9 weight part of pyridine (made by Tokyo Chemical Industry Co., Ltd.) were dissolved at room temperature in 10 weight parts of hexane. To the solution obtained were added dropwise 2.0 weight parts of 2-ethylhexyl chloroformate (made by Tokyo Chemical Industry Co., Ltd.) over a period of 30 minutes. The reaction solution was refluxed with heating for 3 hours in an 80° C. oil bath. To the reaction solution obtained were added 3 weight parts of 5 weight percent sodium bicarbonate aqueous solution and the mixture was stirred for 20 minutes. The reaction solution was separated and the upper (hexane) layer was collected. To the hexane layer were added 3 weight parts of pure water and the mixture was stirred for 20 minutes. The reaction solution was separated and the upper (hexane) layer was collected. The hexane layer obtained was concentrated using an evaporator, yielding polyether 1 in the form of a colorless, transparent oily substance.

The $^1$H NMR data of the starting material polyethylene glycol employed in Synthesis Example 1 and of polyether 1 are given below along with their identifications.

(Polyethylene glycol 200 made by Wako Pure Chemical Industries, Ltd.): $^1$H NMR (DMSO=3.32 ppm) δ (ppm)=3.58 (6H, m), 3.40 (6H, m), 2.50 (4H, m).

(Starting Material Polyethylene Glycol)

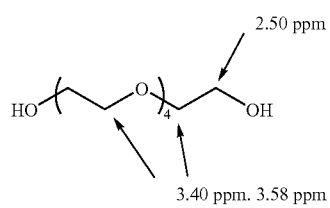

(Polyether 1): $^1$H NMR (DMSO=3.32 ppm) δ(ppm)=0.85 (12H, m), 1.23 (16H, m), 1.54 (2H, m), 3.51 (8H, m), 3.60 (4H, m), 4.00 (4H, dd), 4.17(4H,m).

dropwise 1.3 weight parts of 2-ethylhexyl chloroformate (made by Tokyo Chemical Industry Co., Ltd.) over a period of 30 minutes. The reaction solution was refluxed with heating for 3 hours in an 80° C. oil bath. To the reaction solution obtained were added 3 weight parts of 5 weight percent sodium bicarbonate aqueous solution and the mixture was stirred for 20 minutes. The reaction solution was separated and the upper (hexane) layer was collected. To the hexane layer were added 3 weight parts of pure water and the mixture was stirred for 20 minutes. The reaction solution was separated and the upper (hexane) layer was collected. The hexane layer obtained was concentrated using an evaporator, yielding polyether 2 in the form of a colorless, transparent oily substance.

The $^1$H NMR data of the polyether 2 are given below along with their identifications.

(Polyether 2): $^1$H NMR (DMSO=3.32 ppm) δ(ppm)=0.85 (12H, m), 1.23 (16H, m), 1.54 (2H, m), 3.51 (16H, m), 3.60 (4H, m), 4.00 (4H, dd), 4.17(4H,m).

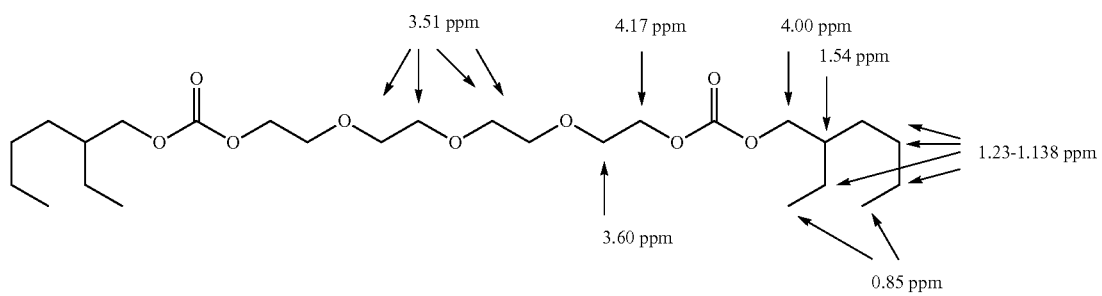

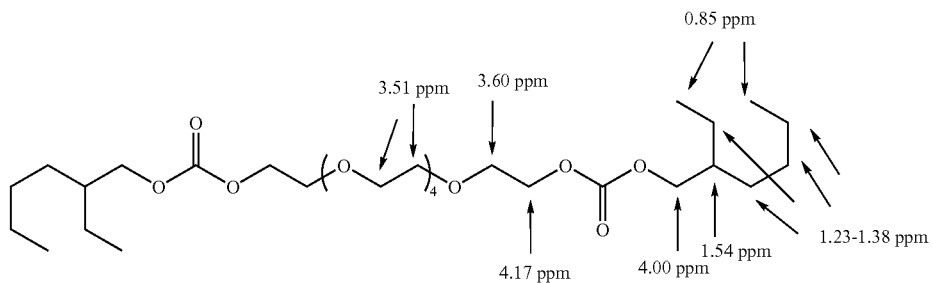

Synthesis Example 2

One weight part of polyethylene glycol (polyethylene glycol 300 made by Wako Pure Chemical Industries, Ltd.) and 0.6 weight part of pyridine (made by Tokyo Chemical Industry Co., Ltd.) were dissolved at room temperature in 10 weight parts of hexane. To the solution obtained were added Synthesis Example 3

One weight part of polyethylene glycol (polyethylene glycol 400 made by Wako Pure Chemical Industries, Ltd.) and 0.4 weight part of pyridine (made by Tokyo Chemical Industry Co., Ltd.) were dissolved at room temperature in 10 weight parts of hexane. To the solution obtained was added dropwise 1.0 weight part of 2-ethylhexyl chloroformate (made by Tokyo Chemical Industry Co., Ltd.) over a period of 30 minutes. The reaction solution was refluxed with heating for 3 hours in an 80° C. oil bath. To the reaction solution obtained were added 3 weight parts of 5 weight percent sodium bicarbonate aqueous solution and the mixture was stirred for 20 minutes. The reaction solution was separated and the upper (hexane) layer was collected. To the hexane layer were added 3 weight parts of pure water and the mixture was stirred for 20 minutes. The reaction solution was separated and the upper (hexane) layer was collected. The hexane layer obtained was concentrated using an evaporator, yielding polyether 3 in the form of a colorless, transparent oily substance.

The $^1$H NMR data of the polyether 3 are given below along with their identifications.

(Polyether 3): $^1$H NMR (DMSO=3.32 ppm) δ(ppm)=0.85 (12H, m), 1.23 (16H, m), 1.54 (2H, m), 3.51 (24H, m), 3.60 (4H, m), 4.00 (4H, dd), 4.17(4H,m).

and the upper (hexane) layer was collected. To the hexane layer were added 3 weight parts of pure water and the mixture was stirred for 20 minutes. The reaction solution was separated and the upper (hexane) layer was collected. The hexane layer obtained was concentrated using an evaporator, yielding polyether 4 in the form of a colorless, transparent oily substance.

The $^1$H NMR data of the polyether 4 are given below along with their identifications.

(Polyether 4): $^1$H NMR (DMSO=3.32 ppm) δ(ppm)=0.85 (12H, m), 1.23 (16H, m), 1.54 (2H, m), 3.51 (40H, m), 3.60 (4H, m), 4.00 (4H, dd), 4.17(4H,m).

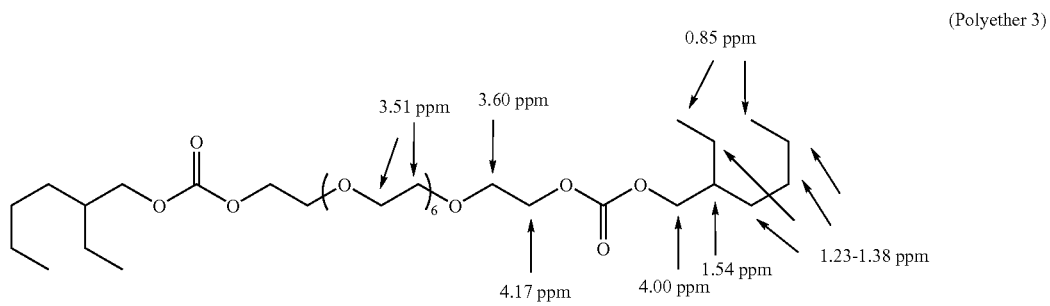

(Polyether 3)

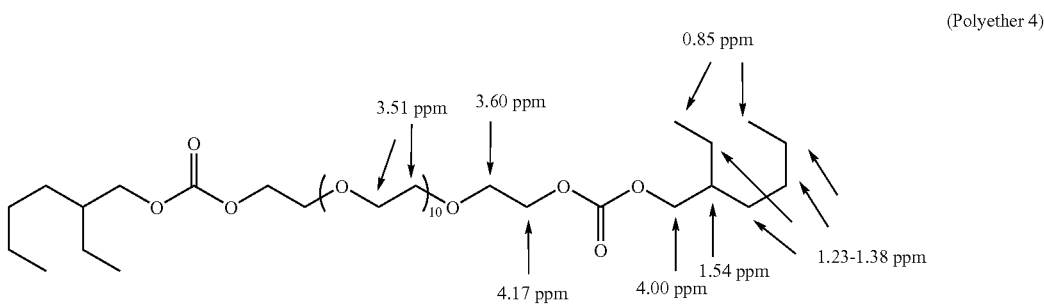

(Polyether 4)

Synthesis Example 4

One weight part of polyethylene glycol (polyethylene glycol 600 made by Wako Pure Chemical Industries, Ltd.) and 0.3 weight part of pyridine (made by Tokyo Chemical Industry Co., Ltd.) were dissolved at room temperature in 10 weight parts of hexane. To the solution obtained was added dropwise 0.7 weight part of 2-ethylhexyl chloroformate (made by Tokyo Chemical Industry Co., Ltd.) over a period of 30 minutes. The reaction solution was refluxed with heating for 3 hours in an 80° C. oil bath. To the reaction solution obtained were added 3 weight parts of 5 weight percent sodium bicarbonate aqueous solution and the mixture was stirred for 20 minutes. The reaction solution was separated Synthesis Example 5

A 1.0 weight part quantity of polyethylene glycol (polyethylene glycol 200 made by Wako Pure Chemical Industries, Ltd.) and 0.87 weight part of pyridine (made by Tokyo Chemical Industry Co., Ltd.) were dissolved at room temperature in 20 weight parts of ethyl acetate. To the solution obtained were added dropwise 1.3 weight parts of isopropyl chloroformate (made by Tokyo Chemical Industry Co., Ltd.) over a period of 30 minutes. The reaction solution was refluxed with heating for 3 hours in an 80° C. oil bath. To the reaction solution obtained were added 3 weight parts of 5 weight percent sodium bicarbonate aqueous solution and the mixture was stirred for 20 minutes. The reaction solution was separated and the upper (ethyl acetate) layer was collected. To the ethyl acetate layer were added 3 weight parts of pure water and the mixture was stirred for 20 minutes. The reaction solution was separated and the upper (ethyl acetate) layer was collected. The ethyl acetate layer obtained was concentrated using an evaporator, yielding polyether 5 in the form of a colorless to pale yellow, transparent oily substance.

The $^1$H NMR data of the polyether 5 are given below along with their identifications.

(Polyether 5): $^1$H NMR (DMSO=3.32 ppm) δ(ppm)=1.29 (12H, m), 3.65 (8H, m), 3.72 (4H, t), 4.28 (4H, t), 4.82-4.91 (2H,m).

Synthesis Example 7

A 1.0 weight part quantity of polyethylene glycol (polyethylene glycol 300 made by Wako Pure Chemical Industries, Ltd.) and 0.58 weight part of pyridine (made by Tokyo Chemical Industry Co., Ltd.) were dissolved at room temperature in 20 weight parts of ethyl acetate. To the solution obtained was added dropwise 0.86 weight part of isopropyl chloroformate (made by Tokyo Chemical Industry Co., Ltd.) over a period of 30 minutes. The reaction solution was refluxed with heating for 3 hours in an 80° C. oil bath. To the reaction solution obtained were added 3 weight parts of 5 weight percent sodium bicarbonate aqueous solution and the mixture was stirred for 20 minutes. The reaction solution was separated and the upper (ethyl acetate) layer was collected. To the ethyl acetate layer were added 3 weight parts of pure water and the mixture was stirred for 20 minutes. The reaction solution was separated and the upper (ethyl acetate) layer was collected. The ethyl acetate layer obtained was concentrated using an evaporator, yielding polyether 7 in the form of a colorless to pale yellow, transparent oily substance.

The $^1$H NMR data of the polyether 7 are given below along with their identifications.

(Polyether 7): $^1$H NMR (DMSO=3.32 ppm) δ(ppm)=1.29 (12H, m), 3.65 (16H, m), 3.72 (4H,t), 4.26 (4H, t), 4.82-4.92 (2H,m).

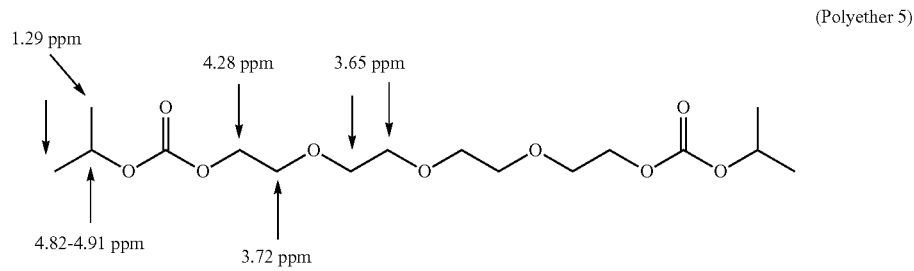 [SMILES: CC(C)OC(=O)OCCOCCOCCOCCOC(=O)OC(C)C]

(Polyether 5)

Synthesis Example 6

With the exception that the 1.3 weight parts of isopropyl chloroformate (made by Tokyo Chemical Industry Co., Ltd.) were replaced with 1.4 weight parts of isobutyl chloroformate (made by Tokyo Chemical Industry Co., Ltd.), an ethyl acetate layer was obtained according to Synthesis Example 5. The ethyl acetate layer obtained was concentrated using an evaporator, yielding polyether 6 in the form of a colorless to pale yellow, transparent oily substance.

The $^1$H NMR data of the polyether 6 are given below along with their identifications.

(Polyether 6): $^1$H NMR (DMSO=3.32 ppm) δ(ppm)=0.95 (12H, m), 1.91-2.04 (2H, m), 3.66 (8H, t), 3.91 (4H, d), 3.73(4H, t), 4.21-4.29 (4H, m).

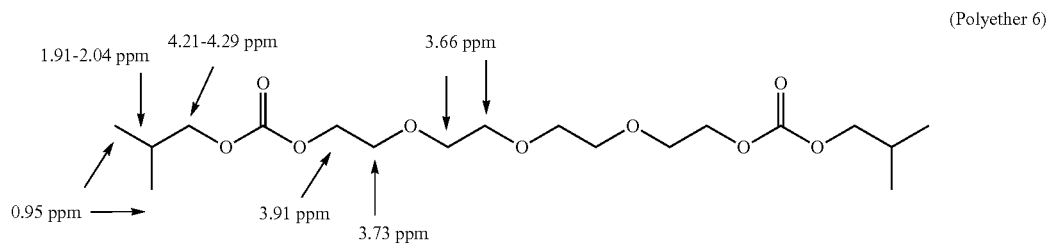 [SMILES: CC(C)COC(=O)OCCOCCOCCOCCOC(=O)OCC(C)C]

(Polyether 6)

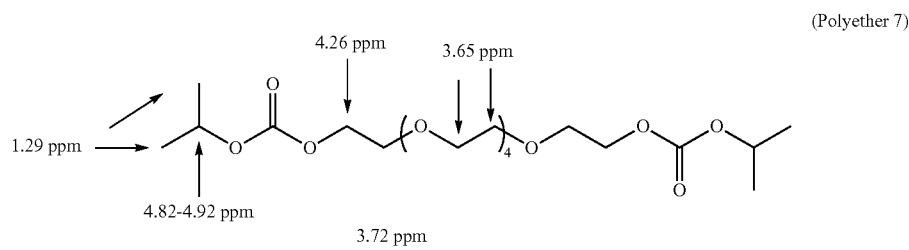

(Polyether 7)

Synthesis Example 8

With the exception that the 0.86 weight part of isopropyl chloroformate (made by Tokyo Chemical Industry Co., Ltd.) was replaced with 0.96 weight part of isobutyl chloroformate (made by Tokyo Chemical Industry Co., Ltd.), an ethyl acetate layer was obtained according to Synthesis Example 7. The ethyl acetate layer obtained was concentrated using an evaporator, yielding polyether 8 in the form of a colorless to pale yellow, transparent oily substance.

The $^1$H NMR data of the polyether 8 are given below along with their identifications.

(Polyether 8): $^1$H NMR (DMSO=3.32 ppm) δ(ppm)=0.94 (12H, m), 1.96-2.08 (2H, m), 3.64-3.66 (16H, m), 3.73 (4H, t), 3.92 (4H, t), 4.27-4.29(4H,m).

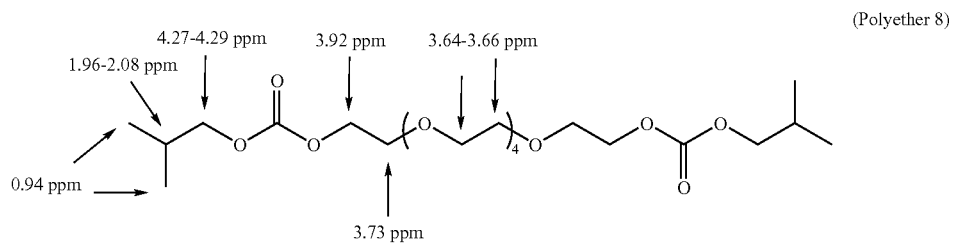

(Polyether 8)

Synthesis Example 9

A 1.0 weight part quantity of polyethylene glycol (polyethylene glycol 400 made by Wako Pure Chemical Industries, Ltd.) and 0.44 weight part of pyridine (made by Tokyo Chemical Industry Co., Ltd.) were dissolved at room temperature in 20 weight parts of ethyl acetate. To the solution obtained was added dropwise 0.64 weight part of isopropyl chloroformate (made by Tokyo Chemical Industry Co., Ltd.) over a period of 30 minutes. The reaction solution was refluxed with heating for 3 hours in an 80° C. oil bath. To the reaction solution obtained were added 3 weight parts of 5 weight percent sodium bicarbonate aqueous solution and the mixture was stirred for 20 minutes. The reaction solution was separated and the upper (ethyl acetate) layer was collected. To the ethyl acetate layer were added 3 weight parts of pure water and the mixture was stirred for 20 minutes. The reaction solution was separated and the upper (ethyl acetate) layer was collected. The ethyl acetate layer obtained was concentrated using an evaporator, yielding polyether 9 in the form of a colorless to pale yellow, transparent oily substance.

The $^1$H NMR data of the polyether 9 are given below along with their identifications.

(Polyether 9): $^1$H NMR (DMSO=3.32 ppm) δ(ppm)=1.29 (12H, m), 3.65 (24H, m), 3.72 (4H,t), 4.26 (4H, t), 4.82-4.92 (2H,m).

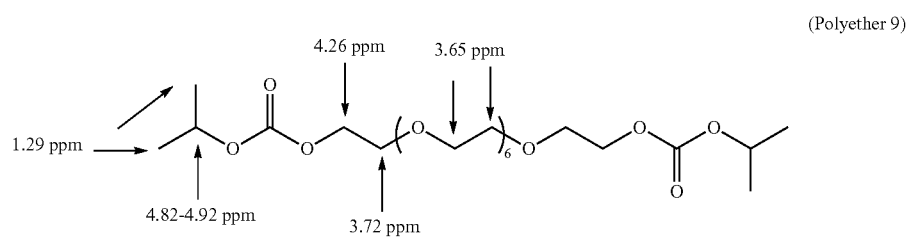

(Polyether 9)

Synthesis Example 10

With the exception that the 0.64 weight part of isopropyl chloroformate (made by Tokyo Chemical Industry Co., Ltd.) was replaced with 0.72 weight part of isobutyl chloroformate (made by Tokyo Chemical Industry Co., Ltd.), an ethyl acetate layer was obtained according to Synthesis Example 9. The ethyl acetate layer obtained was concentrated using an evaporator, yielding polyether 10 in the form of a colorless to pale yellow, transparent oily substance.

The $^1$H NMR data of the polyether 10 are given below along with their identifications.

(Polyether 10): $^1$H NMR (DMSO=3.32 ppm) δ(ppm)=0.95 (12H, m), 1.92-2.02 (2H, m), 3.65 (24H, t), 3.73 (4H, t), 3.92 (4H, m), 4.27 (4H, t).

(Polyether 10)

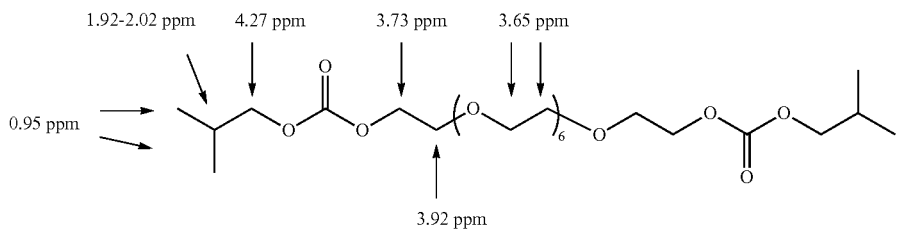

Synthesis Example 11

A 1.0 weight part quantity of polyethylene glycol (polyethylene glycol 600 made by Wako Pure Chemical Industries, Ltd.) and 0.29 weight part of pyridine (made by Tokyo Chemical Industry Co., Ltd.) were dissolved at room temperature in 20 weight parts of ethyl acetate. To the solution obtained was added dropwise 0.43 weight part of isopropyl chloroformate (made by Tokyo Chemical Industry Co., Ltd.) over a period of 30 minutes. The reaction solution was refluxed with heating for 3 hours in an 80° C. oil bath. To the reaction solution obtained were added 3 weight parts of 5 weight percent sodium bicarbonate aqueous solution and the mixture was stirred for 20 minutes. The reaction solution was separated and the upper (ethyl acetate) layer was collected. To the ethyl acetate layer were added 3 weight parts of pure water and the mixture was stirred for 20 minutes. The reaction solution was separated and the upper (ethyl acetate) layer was collected. The ethyl acetate layer obtained was concentrated using an evaporator, yielding polyether 11 in the form of a colorless to pale yellow, transparent oily substance.

The $^1$H NMR data of the polyether 11 are given below along with their identifications.

(Polyether 11): $^1$H NMR (DMSO=3.32 ppm) δ(ppm)=1.29 (12H, m), 3.65 (40H, m), 3.72 (4H,t), 4.26 (4H, t), 4.82-4.92 (2H,m).

(Polyether 11)

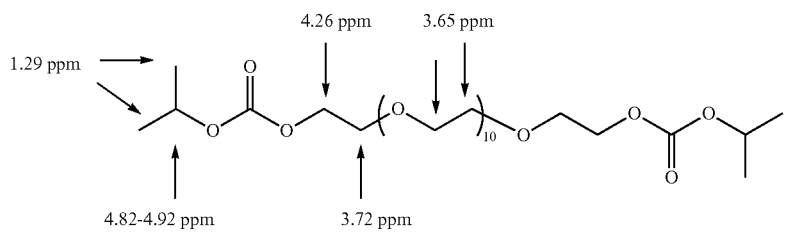

Synthesis Example 12

With the exception that the 0.43 weight part of isopropyl chloroformate (made by Tokyo Chemical Industry Co., Ltd.) was replaced with 0.48 weight part of isobutyl chloroformate (made by Tokyo Chemical Industry Co., Ltd.), an ethyl acetate layer was obtained according to Synthesis Example 11. The ethyl acetate layer obtained was concentrated using an evaporator, yielding polyether 12 in the form of a colorless to pale yellow, transparent oily substance.

The $^1$H NMR data of the polyether 12 are given below along with their identifications (Polyether 12): $^1$H NMR (DMSO=3.32 ppm) δ(ppm)=0.95 (12H, m), 1.92-2.02 (2H, m), 3.65 (40H, m), 3.73 (4H, t), 3.92(4H, m), 4.27 (4H, t). .

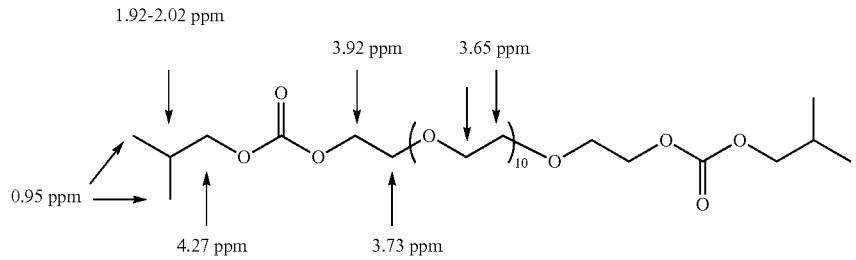

(Polyether 12)

Synthesis Example 13

With the exception that the 0.43 weight part of isopropyl chloroformate (made by Tokyo Chemical Industry Co., Ltd.) was replaced with 0.87 weight part of dodecyl chloroformate (made by Tokyo Chemical Industry Co., Ltd.), an ethyl acetate layer was obtained according to Synthesis Example 11. The ethyl acetate layer obtained was concentrated using an evaporator, yielding polyether 13 in the form of a colorless to pale yellow, transparent oily substance.

The $^1$H NMR data of the polyether 13 are given below along with their identifications.

(Polyether 13): $^1$H NMR (DMSO=3.32 ppm) δ(ppm)= 1.25-1.37 (46H, m), 3.65 (40H, m), 3.72 (4H, t), 4.06-4.18 (4H,t), 4.26-4.28 (4H,t).

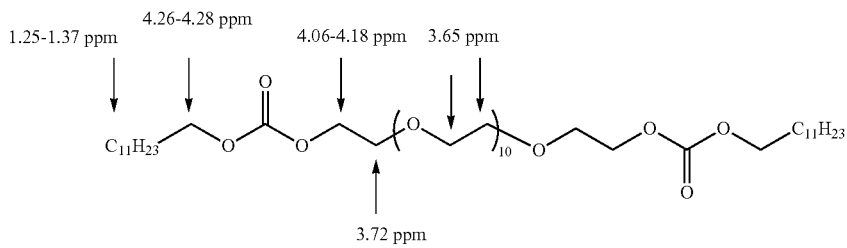

(Polyether 13)

Synthesis Example 14

A 1.0 weight part quantity of polyethylene glycol (polyethylene glycol 1000 made by Wako Pure Chemical Industries, Ltd.) and 0.17 weight part of pyridine (made by Tokyo Chemical Industry Co., Ltd.) were dissolved at room temperature in 30 weight parts of ethyl acetate. To the solution obtained was added dropwise 0.26 weight part of isopropyl chloroformate (made by Tokyo Chemical Industry Co., Ltd.) over a period of 30 minutes. The reaction solution was refluxed with heating for 3 hours in an 80° C. oil bath. To the reaction solution obtained were added 3 weight parts of 5 weight percent sodium bicarbonate aqueous solution and the mixture was stirred for 20 minutes. The reaction solution was separated and the upper (ethyl acetate) layer was collected. To the ethyl acetate layer were added 3 weight parts of pure water and the mixture was stirred for 20 minutes. The reaction solution was separated and the upper (ethyl acetate) layer was collected. The ethyl acetate layer obtained was concentrated using an evaporator, yielding polyether 14 in the form of a colorless to pale yellow, transparent oily substance.

The $^1$H NMR data of the polyether 14 are given below along with their identifications.

(Polyether 14): $^1$H NMR (DMSO=3.32 ppm) δ(ppm)=1.29 (12H, m), 3.65 (76H, m), 3.72 (4H,t), 4.26 (4H, t), 4.82-4.92 (2H,m).

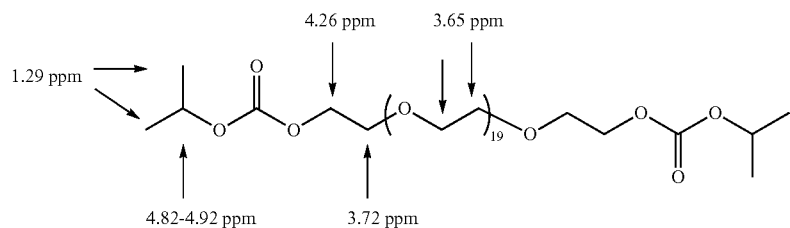

(Polyether 14)

Synthesis Example 15

With the exception that the 0.43 weight part of isopropyl chloroformate (made by Tokyo Chemical Industry Co., Ltd.) was replaced with 0.48 weight part of isobutyl chloroformate (made by Tokyo Chemical Industry Co., Ltd.), an ethyl acetate layer was obtained according to Synthesis Example 14. The ethyl acetate layer obtained was concentrated using an evaporator, yielding polyether 15 in the form of a colorless to pale yellow, transparent oily substance.

The $^1$H NMR data of the polyether 15 are given below along with their identifications.

(Polyether 15): $^1$H NMR (DMSO=3.32 ppm) δ(ppm)=0.95 (12H, m), 1.92-2.02 (2H, m), 3.65 (76H, m), 3.73 (4H, t), 3.92(4H, m), 4.27 (4H, t).

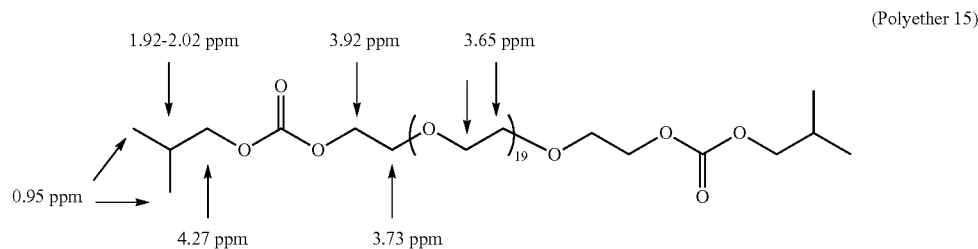

(Polyether 15)

Synthesis Example 16

With the exception that the 0.43 weight part of isopropyl chloroformate (made by Tokyo Chemical Industry Co., Ltd.) was replaced with 0.48 weight part of 2-ethylhexyl chloroformate (made by Tokyo Chemical Industry Co., Ltd.), an ethyl acetate layer was obtained according to Synthesis Example 14. The ethyl acetate layer obtained was concentrated using an evaporator, yielding polyether 16 in the form of a colorless to pale yellow, transparent oily substance.

The $^1$H NMR data of the polyether 16 are given below along with their identifications.

(Polyether 16): $^1$H NMR (DMSO=3.32 ppm) δ(ppm)=0.85 (12H, m), 1.23 (16H, m), 1.64 (2H, m), 3.51 (76H, m), 3.60 (4H, m), 4.00 (4H, dd), 4.17(4H,m).

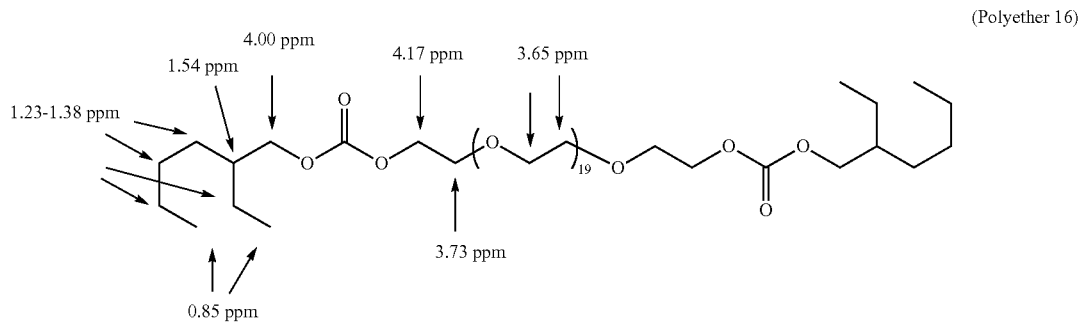

(Polyether 16)

Synthesis Example 17

A 1.0 weight part quantity of polypropylene glycol diol (polypropylene glycol diol 400 made by Wako Pure Chemical Industries, Ltd.) and 0.44 weight part of pyridine (made by Tokyo Chemical Industry Co., Ltd.) were dissolved at room temperature in 20 weight parts of ethyl acetate. To the solution obtained was added dropwise 0.64 weight part of isopropyl chloroformate (made by Tokyo Chemical Industry Co., Ltd.) over a period of 30 minutes. The reaction solution was refluxed with heating for 3 hours in an 80° C. oil bath. To the reaction solution obtained were added 3 weight parts of 5 weight percent sodium bicarbonate aqueous solution and the mixture was stirred for 20 minutes. The reaction solution was separated and the upper (ethyl acetate) layer was collected. To the ethyl acetate layer were added 3 weight parts of pure water and the mixture was stirred for 20 minutes. The reaction solution was separated and the upper (ethyl acetate) layer was collected. The ethyl acetate layer obtained was concentrated using an evaporator, yielding polyether 17 in the form of a colorless to pale yellow, transparent oily substance.

The $^1$H NMR data of the polyether 17 are given below along with their identifications.

(Polyether 17): $^1$H NMR (DMSO=3.32 ppm) δ (ppm)= 1.09-1.18 (12H, m), 1.25-1.30 (15H, m), 3.13-3.74 (15H, m), 4.82-4.91 (2H, m).

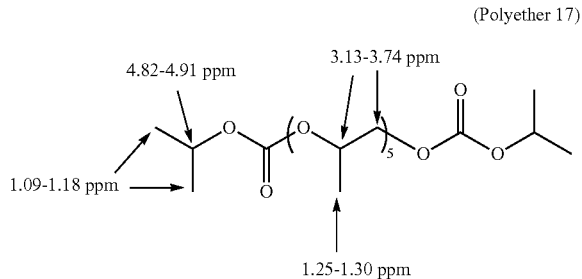

(Polyether 17)

Synthesis Example 18

With the exception that the 0.64 weight part of isopropyl chloroformate (made by Tokyo Chemical Industry Co., Ltd.) was replaced with 0.72 weight part of isobutyl chloroformate (made by Tokyo Chemical Industry Co., Ltd.), an ethyl acetate layer was obtained according to Synthesis Example 17. The ethyl acetate layer obtained was concentrated using an evaporator, yielding polyether 18 in the form of a colorless to pale yellow, transparent oily substance.

The $^1$H NMR data of the polyether 18 are given below along with their identifications.

(Polyether 18): $^1$H NMR (DMSO=3.32 ppm) δ (ppm)= 0.89 (12H, m), 1.27-1.44 (15H, m), 1.59-1.62 (2H, m), 3.39-3.59 (15H, m), 4.00 (4H, m).

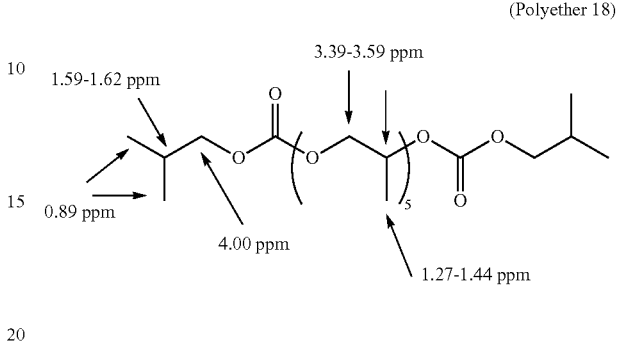

(Polyether 18)

Synthesis Example 19

With the exception that the 0.64 weight part of isopropyl chloroformate (made by Tokyo Chemical Industry Co., Ltd.) was replaced with 1.0 weight part of 2-ethylhexyl chloroformate (made by Tokyo Chemical Industry Co., Ltd.), an ethyl acetate layer was obtained according to Synthesis Example 17. The ethyl acetate layer obtained was concentrated using an evaporator, yielding polyether 19 in the form of a colorless to pale yellow, transparent oily substance.

The $^1$H NMR data of the polyether 19 are given below along with their identifications.

(Polyether 19): $^1$H NMR (DMSO=3.32 ppm) δ(ppm)=0.85 (12H, m), 1.22-1.44 (31H, m), 1.54 (2H, m), 3.39-3.62 (19H, m).

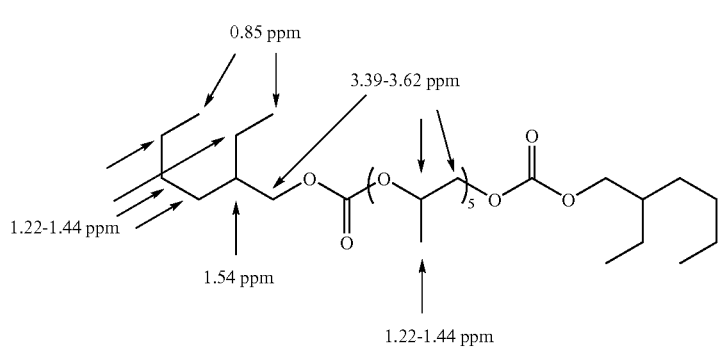

(Polyether 19)

Synthesis Example 20

A 1.0 weight part quantity of diol-type polypropylene glycol (polypropylene glycol diol 1000 made by Wako Pure Chemical Industries, Ltd.) and 0.17 weight part of pyridine (made by Tokyo Chemical Industry Co., Ltd.) were dissolved at room temperature in 20 weight parts of ethyl acetate. To the solution obtained was added dropwise 0.26 weight part of isopropyl chloroformate (made by Tokyo Chemical Industry Co., Ltd.) over a period of 30 minutes. The reaction solution was refluxed with heating for 3 hours in an 80° C. oil bath. To the reaction solution obtained were added 3 weight parts of 5 weight percent sodium bicarbonate aqueous solution and the mixture was stirred for 20 minutes. The reaction solution was separated and the upper (ethyl acetate) layer was collected. To the ethyl acetate layer were added 3 weight parts of pure water and the mixture was stirred for 20 minutes. The reaction solution was separated and the upper (ethyl acetate) layer was collected. The ethyl acetate layer obtained was concentrated using an evaporator, yielding polyether 20 in the form of a pale yellow, transparent oily substance.

The $^1$H NMR data of the polyether 20 are given below along with their identifications.

(Polyether 20): $^1$H NMR (DMSO=3.32 ppm) δ (ppm)= 1.08-1.18 (54H, m), 3.32-3.71 (42H,m), 4.82-4.91 (2H,m).

(Polyether 20)

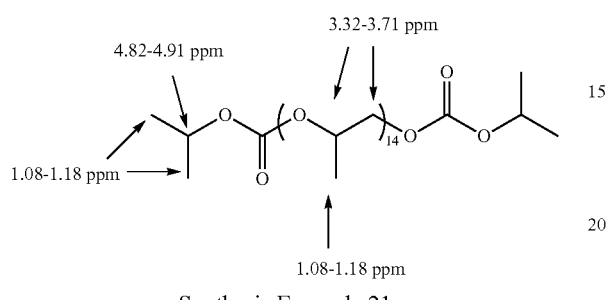

Synthesis Example 21

With the exception that the 0.26 weight part of isopropyl chloroformate (made by Tokyo Chemical Industry Co., Ltd.) was replaced with 0.29 weight part of isobutyl chloroformate (made by Tokyo Chemical Industry Co., Ltd.), an ethyl acetate layer was obtained according to Synthesis Example 20. The ethyl acetate layer obtained was concentrated using an evaporator, yielding polyether 21 in the faun of a pale yellow, transparent oily substance.

The $^1$H NMR data of the polyether 21 are given below along with their identifications.

(Polyether 21): $^1$H NMR (DMSO=3.32 ppm) δ(ppm)= 1.08-1.14 (12H, m), 1.27-1.30 (42H,m), 1.43-1.46(2H m), 3.32-3.71 (42H,m), 4.83-4.91 (4H,m).

(Polyether 21)

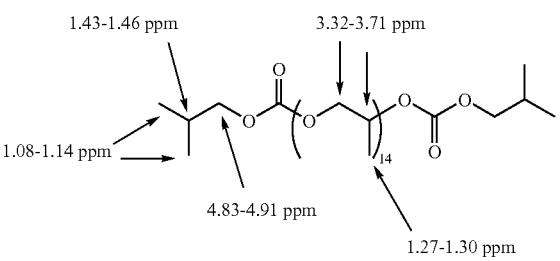

Synthesis Example 22

With the exception that the 0.26 weight part of isopropyl chloroformate (made by Tokyo Chemical Industry Co., Ltd.) was replaced with 0.40 weight part of 2-ethylhexyl chloroformate (made by Tokyo Chemical Industry Co., Ltd.), an ethyl acetate layer was obtained according to Synthesis Example 20. The ethyl acetate layer obtained was concentrated using an evaporator, yielding polyether 22 in the form of a pale yellow, transparent oily substance.

The $^1$H NMR data of the polyether 22 are given below along with their identifications.

(Polyether 22): $^1$H NMR (DMSO=3.32 ppm) δ (ppm)= 0.87-0.91 (12H, m), 1.10-1.46 (58H, m), 1.56-1.63(2H,m), 3.28-3.67(42H,m), 3.97-4.08(4H,m).

(Polyether 22)

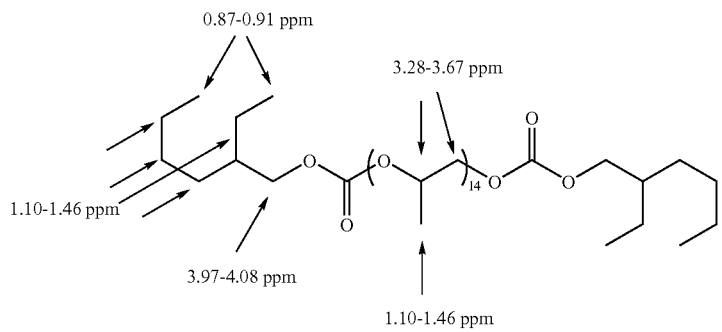

Synthesis Example 23

A 1.0 weight part quantity of diol-type polypropylene glycol (polypropylene glycol diol 3000 made by Wako Pure Chemical Industries, Ltd.) and 0.058 weight part of pyridine (made by Tokyo Chemical Industry Co., Ltd.) were dissolved at room temperature in 20 weight parts of ethyl acetate. To the solution obtained was added dropwise 0.09 weight part of isopropyl chloroformate (made by Tokyo Chemical Industry Co., Ltd.) over a period of 30 minutes. The reaction solution was refluxed with heating for 3 hours in an 80° C. oil bath. To the reaction solution obtained were added 3 weight parts of 5 weight percent sodium bicarbonate aqueous solution and the mixture was stirred for 20 minutes. The reaction solution was separated and the upper (ethyl acetate) layer was collected. To the ethyl acetate layer were added 3 weight parts of pure water and the mixture was stirred for 20 minutes. The reaction solution was separated and the upper (ethyl acetate) layer was collected. The ethyl acetate layer obtained was concentrated using an evaporator, yielding polyether 23 in the form of a pale yellow, transparent oily substance.

The $^1$H NMR data of the polyether 23 are given below along with their identifications.

(Polyether 23): $^1$H NMR (DMSO=3.32 ppm) δ(ppm)= 1.12-1.15(162H, m), 3.39-3.74 (150H, m), 4.82-4.90 (2H, m).

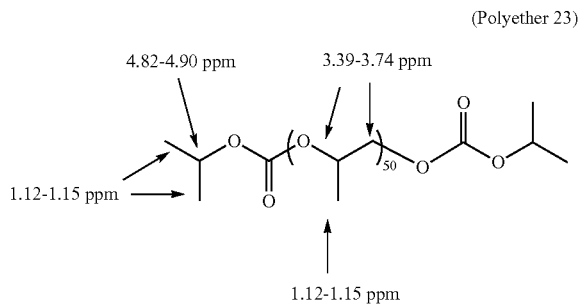

(Polyether 23)

Synthesis Example 24

With the exception that the 0.09 weight part of isopropyl chloroformate (made by Tokyo Chemical Industry Co., Ltd.) was replaced with 0.10 weight part of isobutyl chloroformate (made by Tokyo Chemical Industry Co., Ltd.), an ethyl acetate layer was obtained according to Synthesis Example 23. The ethyl acetate layer obtained was concentrated using an evaporator, yielding polyether 24 in the form of a pale yellow, transparent oily substance.

The $^1$H NMR data of the polyether 24 are given below along with their identifications.

(Polyether 24): $^1$H NMR (DMSO=3.32 ppm) δ (ppm)= 1.14-1.30 (208H, m), 1.59-1.62 (2H,m), 3.39-3.66 (150, m), 4.00-4.08 (4H, m).

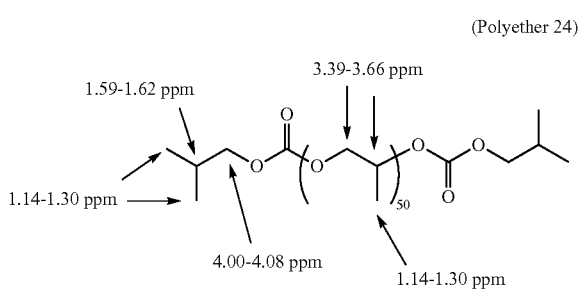

(Polyether 24)

Synthesis Example 25

With the exception that the 0.09 weight part of isopropyl chloroformate (made by Tokyo Chemical Industry Co., Ltd.) was replaced with 0.13 weight part of 2-ethylhexyl chloroformate (made by Tokyo Chemical Industry Co., Ltd.), an ethyl acetate layer was obtained according to Synthesis Example 23. The ethyl acetate layer obtained was concentrated using an evaporator, yielding polyether 25 in the form of a pale yellow, transparent oily substance.

The $^1$H NMR data of the polyether 25 are given below along with their identifications.

(Polyether 25): $^1$H NMR (DMSO=3.32 ppm) δ(ppm)=0.85 (12H,m), 1.14-1.55 (168H, m), 3.39-3.66 (150, m), 4.00-4.09 (4H, m).

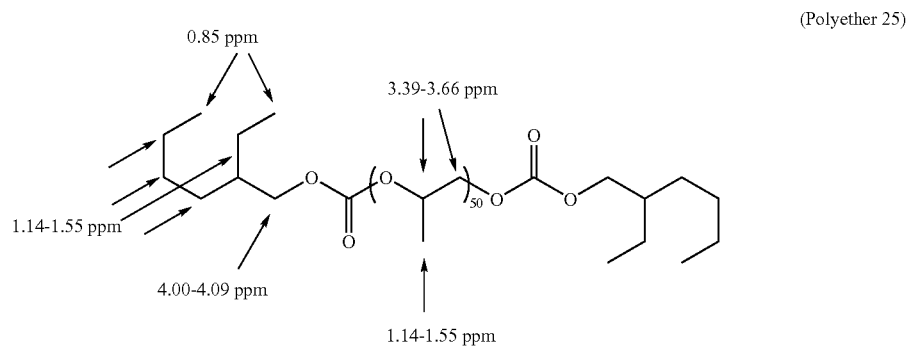

(Polyether 25)

Synthesis Example 26

A 1.0 weight part quantity of triol-type polypropylene glycol (polypropylene glycol triol 300 made by Wako Pure Chemical Industries, Ltd.) and 0.87 weight part of pyridine (made by Tokyo Chemical Industry Co., Ltd.) were dissolved at room temperature in 20 weight parts of ethyl acetate. To the solution obtained were added dropwise 1.3 weight parts of isopropyl chloroformate (made by Tokyo Chemical Industry Co., Ltd.) over a period of 30 minutes. The reaction solution was refluxed with heating for 3 hours in an 80° C. oil bath. To the reaction solution obtained were added 3 weight parts of 5 weight percent sodium bicarbonate aqueous solution and the mixture was stirred for 20 minutes. The reaction solution was separated and the upper (ethyl acetate) layer was collected. To the ethyl acetate layer were added 3 weight parts of pure water and the mixture was stirred for 20 minutes. The reaction solution was separated and the upper (ethyl acetate) layer was collected. The ethyl acetate layer obtained was concentrated using an evaporator, yielding polyether 26 in the form of a colorless to pale yellow, transparent oily substance.

The $^1$H NMR data of the polyether 26 are given below along with their identifications.

(Polyether 26): $^1$H NMR (DMSO=3.32 ppm) δ(ppm)= 1.11-1.44 (27H, m), 3.33-3.70 (14H, m), 4.82-4.91(3H, m).

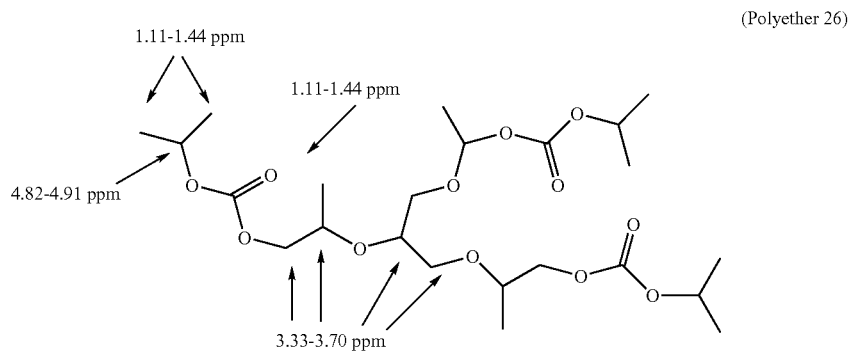 [SMILES: CC(C)OC(=O)OCC(C)OCC(COC(C)OC(=O)OC(C)C)OC(C)COC(=O)OC(C)C]

(Polyether 26)

Synthesis Example 27

With the exception that the 1.3 weight parts of isopropyl chloroformate (made by Tokyo Chemical Industry Co., Ltd.) were replaced with 1.4 weight parts of isobutyl chloroformate (made by Tokyo Chemical Industry Co., Ltd.), an ethyl acetate layer was obtained according to Synthesis Example 26. The ethyl acetate layer obtained was concentrated using an evaporator, yielding polyether 27 in the four of a colorless to pale yellow, transparent oily substance.

The $^1$H NMR data of the polyether 27 are given below along with their identifications.

(Polyether 27): $^1$H NMR (DMSO=3.32 ppm) δ(ppm)= 1.11-1.44 (30H, m), 3.33-3.70 (14H, m), 4.27-4.29(6H, m).

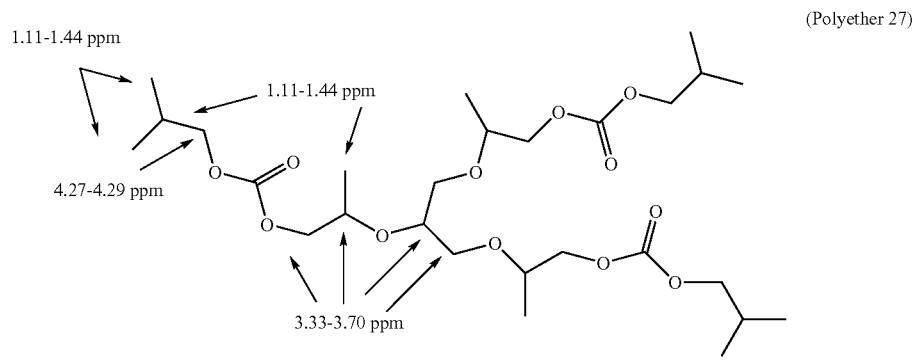 [SMILES: CC(C)COC(=O)OCC(C)OCC(COC(C)COC(=O)OCC(C)C)OC(C)COC(=O)OCC(C)C]

(Polyether 27)

Synthesis Example 28

With the exception that the 1.3 weight parts of isopropyl chloroformate (made by Tokyo Chemical Industry Co., Ltd.) were replaced with 2.0 weight parts of 2-ethylhexyl chloroformate (made by Tokyo Chemical Industry Co., Ltd.), an ethyl acetate layer was obtained according to Synthesis Example 26. The ethyl acetate layer obtained was concentrated using an evaporator, yielding polyether 28 in the form of a colorless to pale yellow, transparent oily substance.

The $^1$H NMR data of the polyether 28 are given below along with their identifications.

(Polyether 28): $^1$H NMR (DMSO=3.32 ppm) δ(ppm)=0.89 (18H, t), 1.11-1.44 (33H, m), 1.59 (3H, m), 3.33-3.70 (14H, m), 3.98-4.09(6H,m).

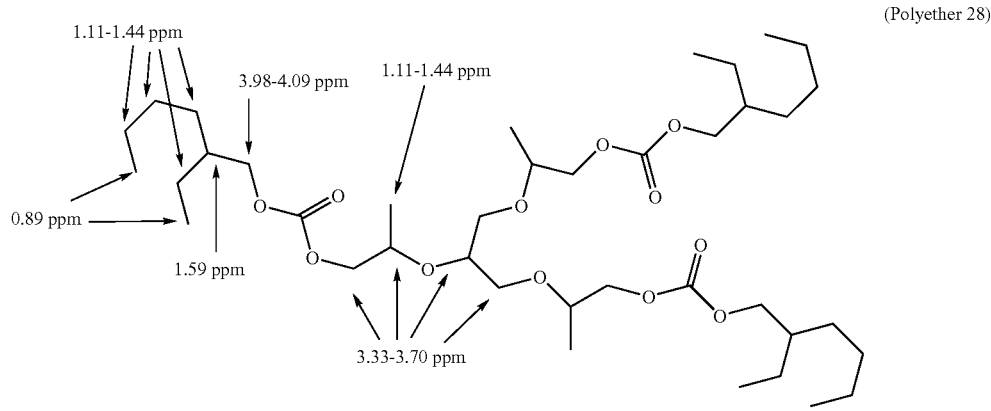 [SMILES: CCCCC(CC)COC(=O)OCC(C)OCC(COC(C)COC(=O)OCC(CC)CCCC)OC(C)COC(=O)OCC(CC)CCCC]

(Polyether 28)

Synthesis Example 29

A 1.0 weight part quantity of triol-type polypropylene glycol (polypropylene glycol triol 700 made by Wako Pure Chemical Industries, Ltd.) and 0.37 weight part of pyridine (made by Tokyo Chemical Industry Co., Ltd.) were dissolved at room temperature in 20 weight parts of ethyl acetate. To the solution obtained was added dropwise 0.55 weight part of isopropyl chloroformate (made by Tokyo Chemical Industry Co., Ltd.) over a period of 30 minutes. The reaction solution was refluxed with heating for 3 hours in an 80° C. oil bath. To the reaction solution obtained were added 3 weight parts of 5 weight percent sodium bicarbonate aqueous solution and the mixture was stirred for 20 minutes. The reaction solution was separated and the upper (ethyl acetate) layer was collected. To the ethyl acetate layer were added 3 weight parts of pure water and the mixture was stirred for 20 minutes. The reaction solution was separated and the upper (ethyl acetate) layer was collected. The ethyl acetate layer obtained was concentrated using an evaporator, yielding polyether 29 in the form of a colorless to pale yellow, transparent oily substance.

The $^1$H NMR data of the polyether 29 are given below along with their identifications.

(Polyether 29): $^1$H NMR (DMSO=3.32 ppm) δ(ppm)= 1.09-1.14 (27H, m), 1.24-1.30 (18H, m), 3.30-3.59 (32H, m), 4.82-4.91 (3H, m).

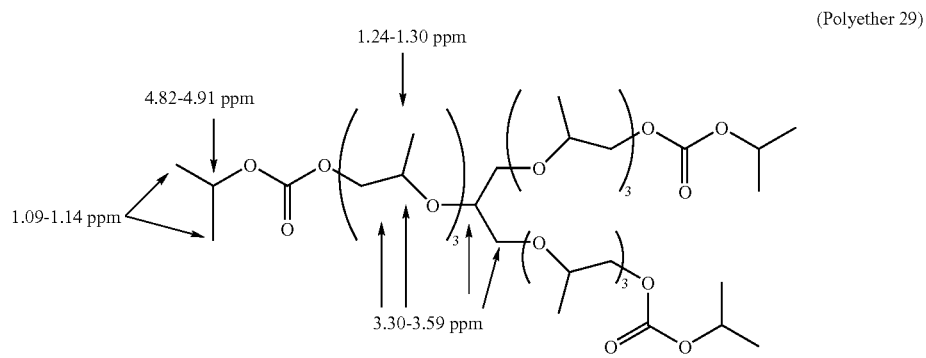

(Polyether 29)

Synthesis Example 30

With the exception that the 0.55 weight part of isopropyl chloroformate (made by Tokyo Chemical Industry Co., Ltd.) was replaced with 0.61 weight part of isobutyl chloroformate (made by Tokyo Chemical Industry Co., Ltd.), an ethyl acetate layer was obtained according to Synthesis Example 29. The ethyl acetate layer obtained was concentrated using an evaporator, yielding polyether 30 in the form of a colorless to pale yellow, transparent oily substance.

The $^1$H NMR data of the polyether 30 are given below along with their identifications.

(Polyether 30): $^1$H NMR (DMSO=3.32 ppm) δ(ppm)= 1.11-1.43 (48H, m), 3.30-3.69 (32H, m), 4.27-4.30 (6H, m).

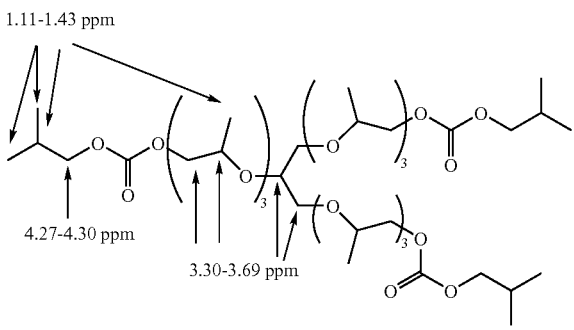

(Polyether 30)

Synthesis Example 31

With the exception that the 0.55 weight part of isopropyl chloroformate (made by Tokyo Chemical Industry Co., Ltd.) was replaced with 0.87 weight part of 2-ethylhexyl chloroformate (made by Tokyo Chemical Industry Co., Ltd.), an ethyl acetate layer was obtained according to Synthesis Example 29. The ethyl acetate layer obtained was concentrated using an evaporator, yielding polyether 31 in the form of a colorless to pale yellow, transparent oily substance.

The $^1$H NMR data of the polyether 31 are given below along with their identifications.

(Polyether 31): $^1$H NMR (DMSO=3.32 ppm) δ(ppm)=0.89 (18H, t), 1.13-1.46 (51H, m), 1.56-1.63 (3H, m), 3.33-3.66 (32H,m), 4.00-4.12 (6H, m).

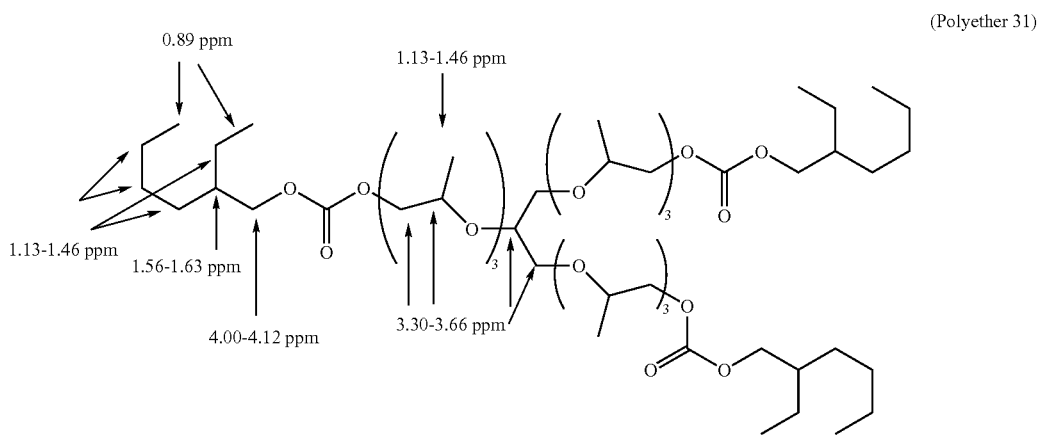

(Polyether 31)

Synthesis Example 32

A 1.0 weight part quantity of triol-type polypropylene glycol (polypropylene glycol triol 1500 made by Wako Pure Chemical Industries, Ltd.) and 0.17 weight part of pyridine (made by Tokyo Chemical Industry Co., Ltd.) were dissolved at room temperature in 20 weight parts of ethyl acetate. To the solution obtained was added dropwise 0.26 weight part of isopropyl chloroformate (made by Tokyo Chemical Industry Co., Ltd.) over a period of 30 minutes. The reaction solution was refluxed with heating for 3 hours in an 80° C. oil bath. To the reaction solution obtained were added 3 weight parts of 5 weight percent sodium bicarbonate aqueous solution and the mixture was stirred for 20 minutes. The reaction solution was separated and the upper (ethyl acetate) layer was collected. To the ethyl acetate layer were added 3 weight parts of pure water and the mixture was stirred for 20 minutes. The reaction solution was separated and the upper (ethyl acetate) layer was collected. The ethyl acetate layer obtained was concentrated using an evaporator, yielding polyether 32 in the form of a pale yellow, transparent oily substance.

The $^1$H NMR data of the polyether 32 are given below along with their identifications.

(Polyether 32): $^1$H NMR (DMSO=3.32 ppm) δ(ppm)= 1.09-1.14 (18H, m), 1.23-1.30 (72H, m), 3.30-3.59 (77H, m), 4.82-4.91 (3H, m).

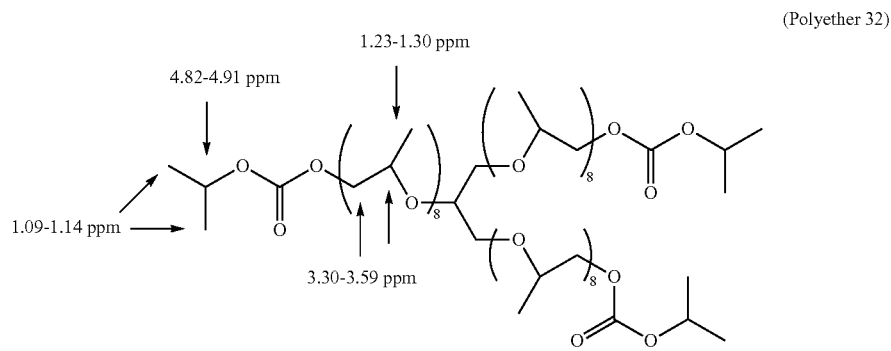

(Polyether 32)

Synthesis Example 33

With the exception that the 0.26 weight part of isopropyl chloroformate (made by Tokyo Chemical Industry Co., Ltd.) was replaced with 0.29 weight part of isobutyl chloroformate (made by Tokyo Chemical Industry Co., Ltd.), an ethyl acetate layer was obtained according to Synthesis Example 32. The ethyl acetate layer obtained was concentrated using an evaporator, yielding polyether 33 in the form of a pale yellow, transparent oily substance.

The $^1$H NMR data of the polyether 33 are given below along with their identifications.

(Polyether 33): $^1$H NMR (DMSO=3.32 ppm) δ(ppm)= 1.11-1.43 (93H, m), 3.30-3.59 (77H, m), 4.27-4.30 (6H, m).

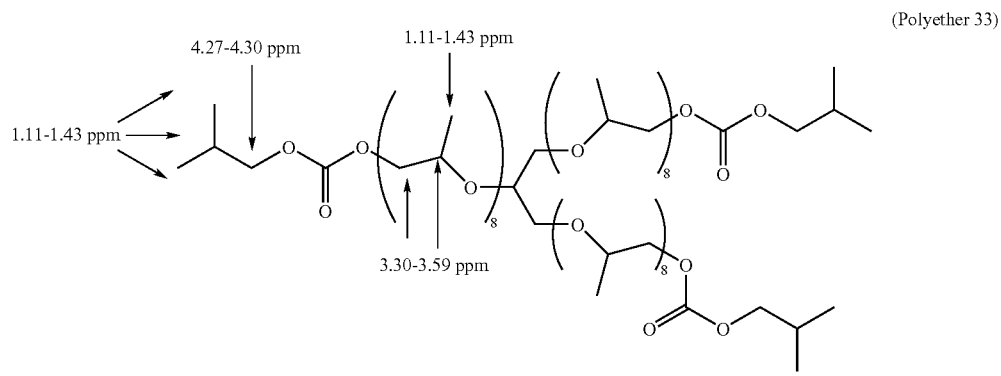

(Polyether 33)

Synthesis Example 34

With the exception that the 0.26 weight part of isopropyl chloroformate (made by Tokyo Chemical Industry Co., Ltd.) was replaced with 0.40 weight part of 2-ethylhexyl chloroformate (made by Tokyo Chemical Industry Co., Ltd.), an ethyl acetate layer was obtained according to Synthesis Example 32. The ethyl acetate layer obtained was concentrated using an evaporator, yielding polyether 34 in the form of a pale yellow, transparent oily substance.

The $^1$H NMR data of the polyether 34 are given below along with their identifications.

(Polyether 34): $^1$H NMR (DMSO=3.32 ppm) δ(ppm)=0.89 (18H, t), 1.13-1.46 (96H, m), 1.56-1.63 (3H, m), 3.33-3.66 (77H, m), 4.00-4.12 (6H, m).

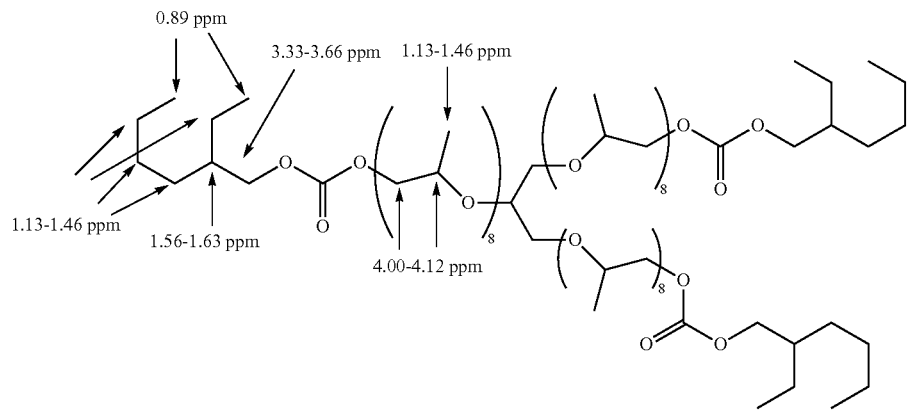

(Polyether 34)

Synthesis Example 35

A 1.0 weight part quantity of triol-type polypropylene glycol (polypropylene glycol triol 3000 made by Wako Pure Chemical Industries, Ltd.) and 0.087 weight part of pyridine (made by Tokyo Chemical Industry Co., Ltd.) were dissolved at room temperature in 20 weight parts of ethyl acetate. To the solution obtained was added dropwise 0.13 weight part of isopropyl chloroformate (made by Tokyo Chemical Industry Co., Ltd.) over a period of 30 minutes. The reaction solution was refluxed with heating for 3 hours in an 80° C. oil bath. To the reaction solution obtained were added 3 weight parts of 5 weight percent sodium bicarbonate aqueous solution and the mixture was stirred for 20 minutes. The reaction solution was separated and the upper (ethyl acetate) layer was collected. To the ethyl acetate layer were added 3 weight parts of pure water and the mixture was stirred for 20 minutes. The reaction solution was separated and the upper (ethyl acetate) layer was collected. The ethyl acetate layer obtained was concentrated using an evaporator, yielding polyether 35 in the form of a pale yellow, transparent oily substance.

The $^1$H NMR data of the polyether 35 are given below along with their identifications.

(Polyether 35): $^1$H NMR (DMSO=3.32 ppm) δ(ppm)= 1.09-1.30 (171H, m), 3.30-3.59 (158H, m), 4.82-4.91 (3H, m).

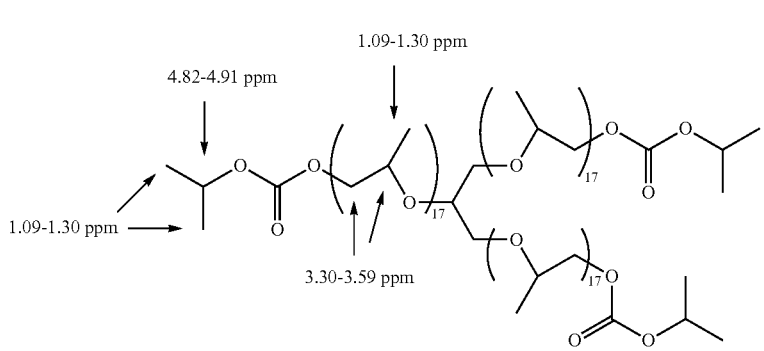

(Polyether 35)

Synthesis Example 36

With the exception that the 0.13 weight part of isopropyl chloroformate (made by Tokyo Chemical Industry Co., Ltd.) was replaced with 0.14 weight part of isobutyl chloroformate (made by Tokyo Chemical Industry Co., Ltd.), an ethyl acetate layer was obtained according to Synthesis Example 35. The ethyl acetate layer obtained was concentrated using an evaporator, yielding Example Compound (36) of n≈17 (referred to as polyether 36 hereinafter) in the form of a pale yellow, transparent oily substance.

The $^1$H NMR data of the polyether 36 obtained in Synthesis Example 36 are given below along with their identifications.

(Polyether 36): $^1$H NMR (DMSO=3.32 ppm) δ(ppm)= 1.11-1.43 (174H, m), 3.30-3.59 (158H, m), 4.27-4.30 (6H, m).

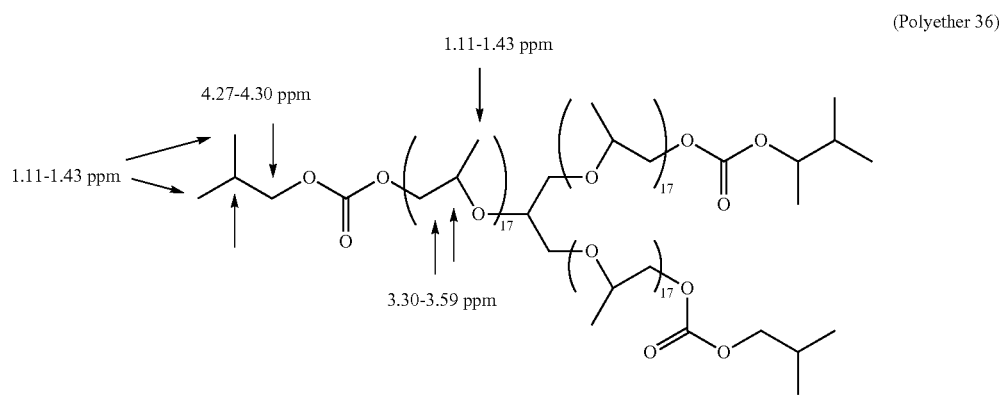

(Polyether 36)

Synthesis Example 37

With the exception that the 0.13 weight part of isopropyl chloroformate (made by Tokyo Chemical Industry Co., Ltd.) was replaced with 0.20 weight part of 2-ethylhexyl chloroformate (made by Tokyo Chemical Industry Co., Ltd.), an ethyl acetate layer was obtained according to Synthesis Example 35. The ethyl acetate layer obtained was concentrated using an evaporator, yielding polyether 37 in the form of a pale yellow, transparent oily substance.

The $^1$H NMR data of the polyether 37 are given below along with their identifications.

(Polyether 37): $^1$H NMR (DMSO=3.32 ppm) δ(ppm)=0.89 (18H, t), 1.13-1.46 (177H, m), 1.56-1.63 (3H, m), 3.33-3.66 (158H, m), 4.00-4.12 (6H, m).

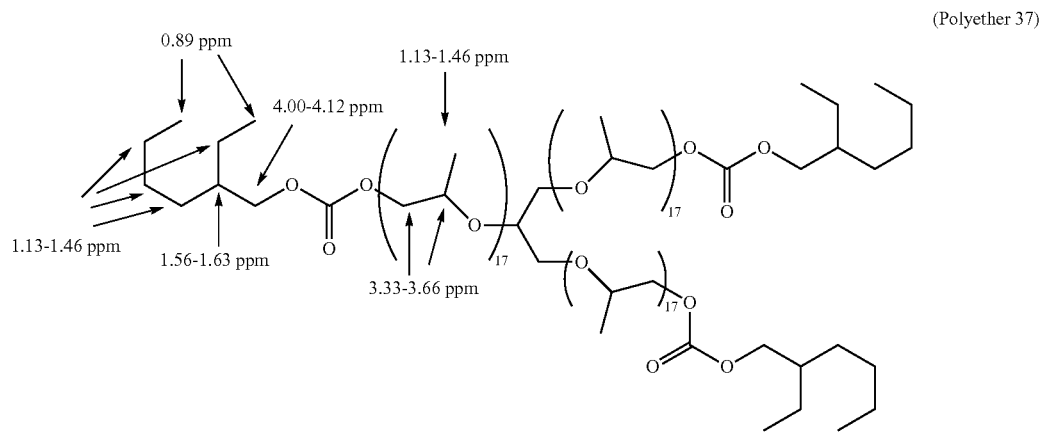

(Polyether 37)

Synthesis Example 38

A 1.0 weight part quantity of triol-type polypropylene glycol (polypropylene glycol triol 4000 made by Wako Pure Chemical Industries, Ltd.) and 0.065 weight part of pyridine (made by Tokyo Chemical Industry Co., Ltd.) were dissolved at room temperature in 20 weight parts of ethyl acetate. To the solution obtained was added dropwise 0.10 weight part of isopropyl chloroformate (made by Tokyo Chemical Industry Co., Ltd.) over a period of 30 minutes. The reaction solution was refluxed with heating for 3 hours in an 80° C. oil bath. To the reaction solution obtained were added 3 weight parts of 5 weight percent sodium bicarbonate aqueous solution and the mixture was stirred for 20 minutes. The reaction solution was separated and the upper (ethyl acetate) layer was collected. To the ethyl acetate layer were added 3 weight parts of pure water and the mixture was stirred for 20 minutes. The reaction solution was separated and the upper (ethyl acetate) layer was collected. The ethyl acetate layer obtained was concentrated using an evaporator, yielding polyether 38 in the form of a pale yellow, transparent oily substance.

The $^1$H NMR data of the polyether 38 are given below along with their identifications.

(Polyether 38): $^1$H NMR (DMSO=3.32 ppm) δ(ppm)= 1.10-1.20 (198H, m), 1.26-1.33 (18H, m), 3.28-3.61 (203H, m), 4.81-4.91 (3H, m).

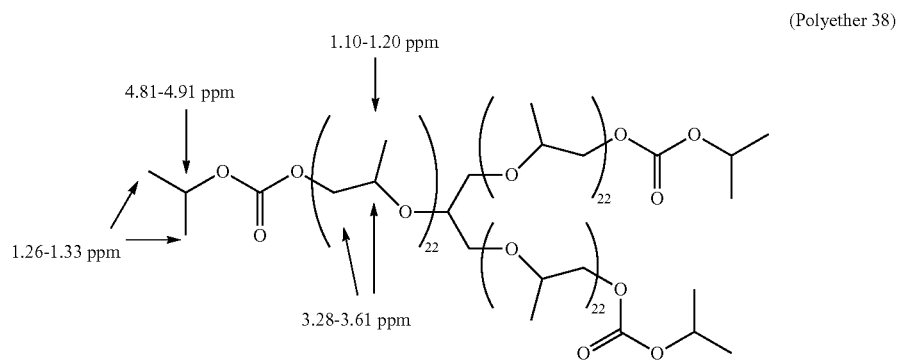

(Polyether 38)

Synthesis Example 39

With the exception that the 0.10 weight part of isopropyl chloroformate (made by Tokyo Chemical Industry Co., Ltd.) was replaced with 0.11 weight part of isobutyl chloroformate (made by Tokyo Chemical Industry Co., Ltd.), an ethyl acetate layer was obtained according to Synthesis Example 38. The ethyl acetate layer obtained was concentrated using an evaporator, yielding polyether 39 in the form of a pale yellow, transparent oily substance.

The $^1$H NMR data of the polyether 39 are given below along with their identifications.

(Polyether 39): $^1$H NMR (DMSO=3.32 ppm) δ(ppm)= 1.11-1.43 (219H, m), 3.30-3.59 (203H, m), 4.27-4.30 (6H, m).

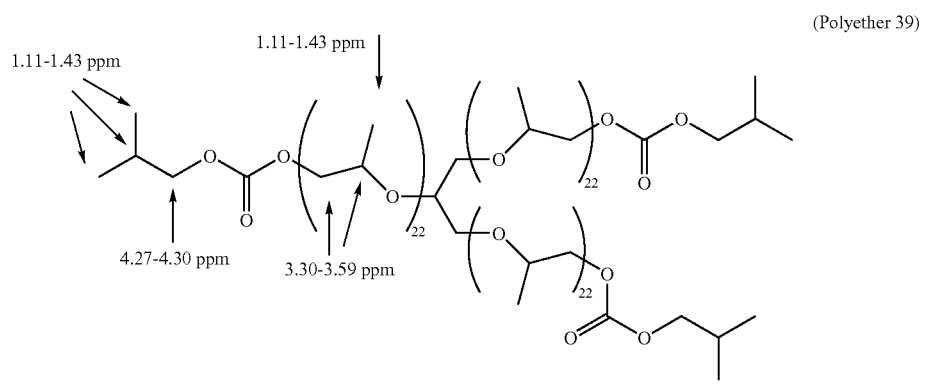

(Polyether 39)

Synthesis Example 40

With the exception that the 0.10 weight part of isopropyl chloroformate (made by Tokyo Chemical Industry Co., Ltd.) was replaced with 0.15 weight part of 2-ethylhexyl chloroformate (made by Tokyo Chemical Industry Co., Ltd.), an ethyl acetate layer was obtained according to Synthesis Example 38. The ethyl acetate layer obtained was concentrated using an evaporator, yielding polyether 40 in the form of a pale yellow, transparent oily substance.

The $^1$H NMR data of the polyether 40 are given below along with their identifications.

(Polyether 40): $^1$H NMR (DMSO=3.32 ppm) δ(ppm)=0.89 (18H, t), 1.13-1.46 (222H, m), 1.56-1.63 (3H, m), 3.33-3.66 (203H, m), 4.00-4.12 (6H, m).

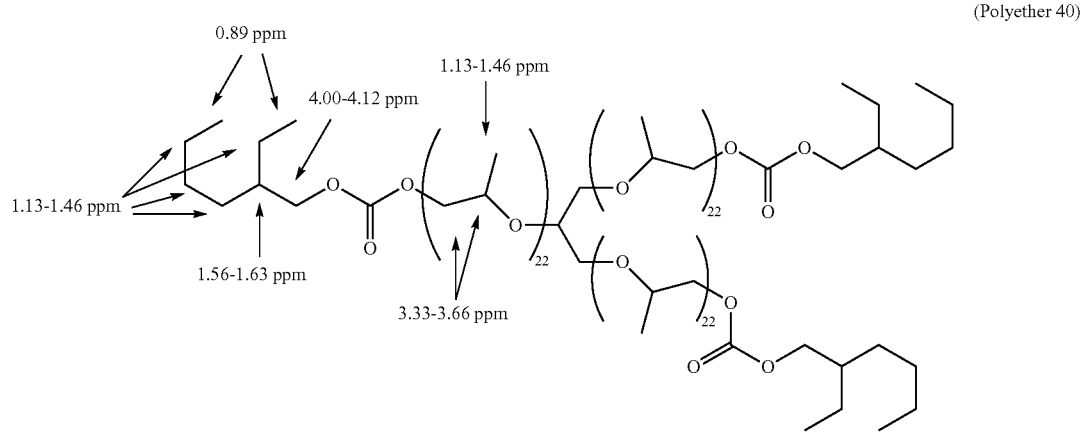
(Polyether 40)

Synthesis Example 41

A 1.0 weight part quantity of diol-type polypropylene glycol (polypropylene glycol diol 400 made by Wako Pure Chemical Industries, Ltd.) and 0.44 weight part of pyridine (made by Tokyo Chemical Industry Co., Ltd.) were dissolved at room temperature in 20 weight parts of ethyl acetate. To the solution obtained were added dropwise 1.31 weight parts of dodecyl chloroformate (made by Tokyo Chemical Industry Co., Ltd.) over a period of 30 minutes. The reaction solution was refluxed with heating for 3 hours in an 80° C. oil bath. To the reaction solution obtained were added 3 weight parts of 5 weight percent sodium bicarbonate aqueous solution and the mixture was stirred for 20 minutes. The reaction solution was separated and the upper (ethyl acetate) layer was collected. To the ethyl acetate layer were added 3 weight parts of pure water and the mixture was stirred for 20 minutes. The reaction solution was separated and the upper (ethyl acetate) layer was collected. The ethyl acetate layer obtained was concentrated using an evaporator, yielding polyether 41 in the form of a colorless to pale yellow, transparent oily substance.

The $^1$H NMR data of the polyether 41 are given below along with their identifications.

(Polyether 41): $^1$H NMR (DMSO=3.32 ppm) δ(ppm)=1.14 (15H, m), 1.26-1.29 (46H, m), 3.32-3.61 (15H, m), 4.11 (4H,t).

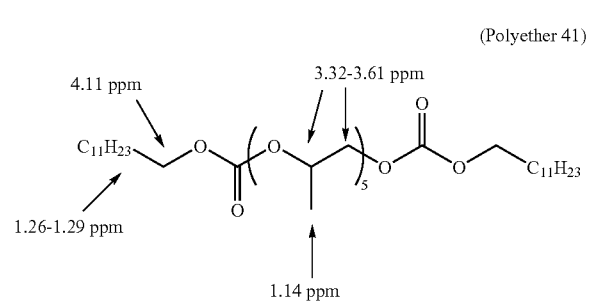
(Polyether 41)

Synthesis Example 42

A 1.0 weight part quantity of triol-type polypropylene glycol (polypropylene glycol triol 300 made by Wako Pure Chemical Industries, Ltd.) and 0.87 weight part of pyridine (made by Tokyo Chemical Industry Co., Ltd.) were dissolved at room temperature in 30 weight parts of ethyl acetate. To the solution obtained were added dropwise 2.61 weight parts of dodecyl chloroformate (made by Tokyo Chemical Industry Co., Ltd.) over a period of 30 minutes. The reaction solution was refluxed with heating for 3 hours in an 80° C. oil bath. To the reaction solution obtained were added 3 weight parts of 5 weight percent sodium bicarbonate aqueous solution and the mixture was stirred for 20 minutes. The reaction solution was separated and the upper (ethyl acetate) layer was collected. To the ethyl acetate layer were added 3 weight parts of pure water and the mixture was stirred for 20 minutes. The reaction solution was separated and the upper (ethyl acetate) layer was collected. The ethyl acetate layer obtained was concentrated using an evaporator, yielding polyether 42 in the form of a colorless to pale yellow, transparent oily substance.

The $^1$H NMR data of the polyether 42 are given below along with their identifications.

(Polyether 42): $^1$H NMR (DMSO=3.32 ppm) δ(ppm)= 1.11-1.44 (78H, m), 3.33-3.70 (14H, m), 4.82-4.91(6H, m).

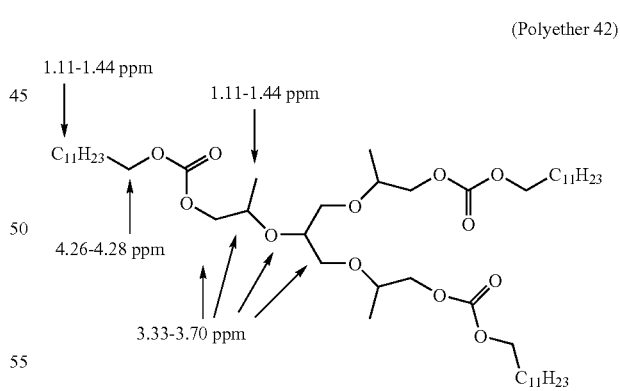
(Polyether 42)

Synthesis Example 43

A 1.0 weight part quantity of triol-type polypropylene glycol (polypropylene glycol triol 700 made by Wako Pure Chemical Industries, Ltd.) and 0.37 weight part of pyridine (made by Tokyo Chemical Industry Co., Ltd.) were dissolved at room temperature in 20 weight parts of ethyl acetate. To the solution obtained were added dropwise 1.12 weight parts of isopropyl chloroformate (made by Tokyo Chemical Industry Co., Ltd.) over a period of 30 minutes. The reaction solution was refluxed with heating for 3 hours in an 80° C. oil bath. To the reaction solution obtained were added 3 weight parts of 5 weight percent sodium bicarbonate aqueous solution and the mixture was stirred for 20 minutes. The reaction solution was separated and the upper (ethyl acetate) layer was collected. To the ethyl acetate layer were added 3 weight parts of pure water and the mixture was stirred for 20 minutes. The reaction solution was separated and the upper (ethyl acetate) layer was collected. The ethyl acetate layer obtained was concentrated using an evaporator, yielding polyether 43 in the form of a colorless to pale yellow, transparent oily substance.

The $^1$H NMR data of the polyether 43 are given below along with their identifications.

(Polyether 43): $^1$H NMR (DMSO=3.32 ppm) δ(ppm)= 1.13-1.36 (96H, m), 3.30-3.62 (32H, m), 4.06-4.17 (6H, m).

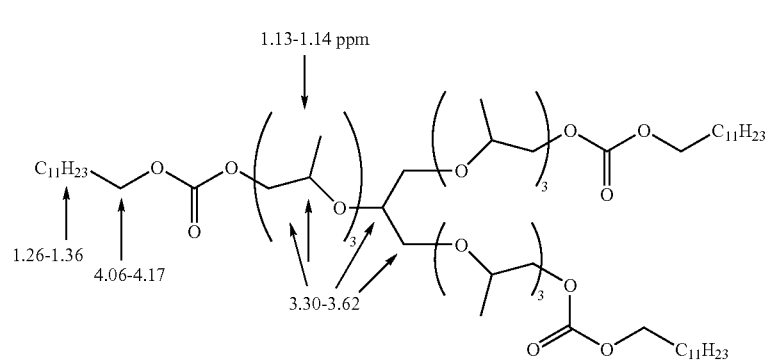

(Polyether 43)

Table 1 shows the correspondence between the polyether compounds obtained above and the general formulas.

TABLE 1

|  | General formula ||||| 
| --- | --- | --- | --- | --- | --- |
|  | (I) | (1) | (2) | (II) | (3) |
| Polyether 1 | ○ | ○ | — | — | — |
| Polyether 2 | ○ | ○ | — | — | — |
| Polyether 3 | ○ | ○ | — | — | — |
| Polyether 4 | ○ | ○ | — | — | — |
| Polyether 5 | ○ | ○ | — | — | — |
| Polyether 6 | ○ | ○ | — | — | — |
| Polyether 7 | ○ | ○ | — | — | — |
| Polyether 8 | ○ | ○ | — | — | — |
| Polyether 9 | ○ | ○ | — | — | — |
| Polyether 10 | ○ | ○ | — | — | — |
| polyether 11 | ○ | ○ | — | — | — |
| Polyether 12 | ○ | ○ | — | — | — |
| Polyether 13 | ○ | ○ | — | — | — |
| Polyether 14 | ○ | ○ | — | — | — |
| Polyether 15 | ○ | ○ | — | — | — |
| Polyether 16 | ○ | ○ | — | — | — |
| Polyether 17 | ○ | — | ○ | — | — |
| Polyether 18 | ○ | — | ○ | — | — |
| Polyether 19 | ○ | — | ○ | — | — |
| Polyether 20 | ○ | — | ○ | — | — |
| Polyether 21 | ○ | — | ○ | — | — |
| Polyether 22 | ○ | — | ○ | — | — |
| Polyether 23 | ○ | — | ○ | — | — |
| Polyether 24 | ○ | — | ○ | — | — |
| Polyether 25 | ○ | — | ○ | — | — |
| Polyether 26 | — | — | — | ○ | ○ |
| Polyether 27 | — | — | — | ○ | ○ |
| Polyether 28 | — | — | — | ○ | ○ |
| Polyether 29 | — | — | — | ○ | ○ |

TABLE 1-continued

|  | General formula ||||| 
| --- | --- | --- | --- | --- | --- |
|  | (I) | (1) | (2) | (II) | (3) |
| Polyether 30 | — | — | — | ○ | ○ |
| Polyether 31 | — | — | — | ○ | ○ |
| Polyether 32 | — | — | — | ○ | ○ |
| Polyether 33 | — | — | — | ○ | ○ |
| Polyether 34 | — | — | — | ○ | ○ |
| Polyether 35 | — | — | — | ○ | ○ |
| Polyether 36 | — | — | — | ○ | ○ |
| Polyether 37 | — | — | — | ○ | ○ |
| Polyether 38 | — | — | — | ○ | ○ |
| Polyether 39 | — | — | — | ○ | ○ |
| Polyether 40 | — | — | — | ○ | ○ |
| Polyether 41 | ○ | — | X | — | — |

TABLE 1-continued

|  | General formula ||||| 
| --- | --- | --- | --- | --- | --- |
|  | (I) | (1) | (2) | (II) | (3) |
| Polyether 42 | — | — | — | ○ | X |
| Polyether 43 | — | — | — | ○ | X |

Comparative Synthesis Example 1

One weight part of 1-octadecanol (made by Wako Pure Chemical Industries, Ltd.) and 0.3 weight part of pyridine (made by Tokyo Chemical Industry Co., Ltd.) were dissolved at room temperature in 10 weight parts of hexane. To the solution obtained was added dropwise 0.7 weight part of 2-ethylhexyl chloroformate (made by Tokyo Chemical Industry Co., Ltd.) over a period of 30 minutes. The reaction solution was refluxed with heating for 3 hours in an 80° C. oil bath. To the reaction solution obtained were added 3 weight parts of 5 weight percent sodium bicarbonate aqueous solution and the mixture was stirred for 20 minutes. The reaction solution was separated and the upper (hexane) layer was collected. To the hexane layer were added 3 weight parts of pure water and the mixture was stirred for 20 minutes. The reaction solution was separated and the upper (hexane) layer was collected. The hexane layer obtained was concentrated using an evaporator, yielding Comparative Compound 1 below in the form of a colorless, transparent oily substance.

Comparative Compound 1

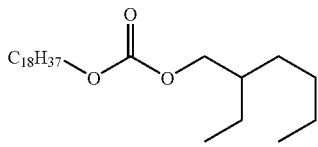

Comparative Synthesis Example 2

One weight part of 2-ethylhexanol (made by Wako Pure Chemical Industries, Ltd.) and 0.7 weight part of pyridine (made by Tokyo Chemical Industry Co., Ltd.) were dissolved at room temperature in 10 weight parts of hexane. To the solution obtained were added dropwise 1.6 weight parts of 2-ethylhexyl chloroformate (made by Tokyo Chemical Industry Co., Ltd.) over a period of 30 minutes. The reaction solution was refluxed with heating for 3 hours in an 80° C. oil bath. To the reaction solution obtained were added 3 weight parts of 5 weight percent sodium bicarbonate aqueous solution and the mixture was stirred for 20 minutes. The reaction solution was separated and the upper (hexane) layer was collected. To the hexane layer were added 3 weight parts of pure water and the mixture was stirred for 20 minutes. The reaction solution was separated and the upper (hexane) layer was collected. The hexane layer obtained was concentrated using an evaporator, yielding Comparative Compound 2 in the form of a colorless, transparent oily substance.

Comparative Compound 2

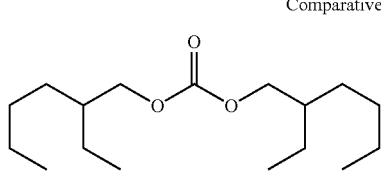

Compound Evaluation 1 (Evaluation of Lubricating Performance and Abrasion Resistance)

(1) Evaluation of Lubricating Performance

A 0.01 mL quantity of each of the compounds indicated in Table 2 was coated on a metal sheet (an SUJ base, made by Technos (Ltd.), with an Ra as measured by an atomic force microscope (AFM) of about 2 nm) to form a lubricating film. The average coefficient of friction of the lubricating film thus formed was measured while being rotated for 10 minutes under the following conditions by the ball-on-disk method with a tribometer made by CMC, Inc. (Switzerland).

Measurement Conditions

Radius: 5 mm; speed: 3 cm/s; load: 5.00 N; air temperature: 21.7° C.; humidity: 48.0 percent.

Metal ball: SUJ2 ball made by Technos (Ltd.)

(2) Evaluation of Abrasion Resistance

The surface of the SUJ2 disk was observed by AFM following rotation for 10 minutes in (1) above, and the depth of the scratches were measured.

The results of the above are given in Table 2. In Table 2, the results of evaluation conducted by rotating the ball and disk alone, without the application of a compound, are given for Comparative Examples 1-4.

TABLE 2

| | Lubricant | Average coefficient of friction | Depth of the scratches on the base |
|---|---|---|---|
| Example 1-1 | Polyether 1 | 0.080 | 40 nm |
| Example 1-2 | Polyether 2 | 0.076 | 38 nm |
| Example 1-3 | Polyether 3 | 0.074 | 35 nm |
| Example 1-4 | Polyether 4 | 0.074 | 34 nm |
| Example 1-5 | Polyether 9 | 0.091 | 81 nm |
| Example 1-6 | Polyether 10 | 0.093 | 86 nm |
| Example 1-7 | Polyether 11 | 0.078 | 90 nm |
| Example 1-8 | Polyether 19 | 0.099 | 49 nm |
| Example 1-9 | Polyether 25 | 0.095 | 151 nm |
| Example 1-10 | Polyether 26 | 0.092 | 57 nm |
| Example 1-11 | Polyether 40 | 0.075 | 80 nm |
| Example 1-12 | Polyether 41 | 0.088 | 93 nm |
| Example 1-13 | Polyether 42 | 0.078 | 90 nm |
| Comp. Ex. 1-1 | Comp. Compound 1 | 0.106 | 216 nm |
| Comp. Ex. 1-2 | Comp. Compound 2 | 0.157 | 358 nm |
| Comp. Ex. 1-3 | Sec-butyl stearate | 0.100 | 234 nm |
| Comp. Ex. 1-4 | None | 5.900 | — |

Evaluation Results

As shown in Table 2, Examples 1-1 to 1-13 exhibited a lower average coefficient of friction than Comparative Example 1-4, and equivalent or better lubricating performance than Comparative Examples 1-1 and 1-3, in which carbonic acid ester lubricants were employed. Thus, the polyether compounds employed in Examples 1-1 to 1-13 were found to provide good lubricating performance on metal surfaces. Since Examples 1-1 to 1-13 exhibited shallower scratches on the base following coefficient of friction measurement than Comparative Examples 1-1 to 1-3, the polyethers employed in Examples 1-1 to 1-13 were determined to improve resistance to abrasion. Based on these results, the polyether compounds of the present invention were found to have good affinity for metals, to have a good abrasion-reducing effect, and as a result, to reduce friction.

Compound Evaluation 2 (Evaluation of Compatibility with Binder)

One hundred weight parts of each of binders A to C below, 1,000 weight parts of cyclohexanone, and 1 weight part of the lubricant indicated in Table 3 were mixed and stirred for 1 hour in magnetic stirrers. Subsequently, 0.1 mL quantities of the mixed solutions obtained were applied dropwise to an OHP sheet and dried under conditions of 70° C. for 48 hours at ordinary pressure. The surface of the dried OHP sheet was visually examined to determine compatibility. Those solutions that were transparent were determined a compatibility rating of "O" and those that were turbid were determined a compatibility rating of "X." For those solutions with a compatibility rating of "O," the quantity of lubricant added was increased to determine the point at which a compatibility of "X" was exhibited. Table 3 shows the concentration of the lubricant when the compatibility became "X."

Binder A: Polyester polyurethane comprising $0.7 \times 10^{-4}$ mole/g of sulfonic acid groups. In the polyurethane, phthalic acid and propylene glycol were contained in the polyester portions, and 4,4'-diphenylmethane diisocyanate was employed as the urethane component. The weight average molecular weight (Mw) calculated by standard polystyrene conversion using DMF solvent containing 0.3 weight percent of lithium bromide was about 70,000.

Binder B: Vinyl chloride copolymer (MR-104, made by Zeon Corporation). The weight average molecular weight (Mw) calculated by standard polystyrene conversion using DMF solvent containing 0.3 weight percent of lithium bromide was about 70,000.

Binder C: Polyether polyurethane comprising $0.6 \times 10^{-4}$ mole/g of sulfonic acid groups. In the polyurethane, a propylene glycol adduct of bisphenol A was contained in the polyether portions, and 4,4'-diphenylmethane diisocyanate was employed as the urethane component. The weight average molecular weight (Mw) calculated by standard polystyrene conversion using DMF solvent containing 0.3 weight percent of lithium bromide was about 70,000.

TABLE 3

|  | Binder A | Binder B | Binder C |
| --- | --- | --- | --- |
| Polyether 1 | Equal to or greater than 30 weight percent | Equal to or greater than 30 weight percent | Equal to or greater than 30 weight percent |
| Polyether 2 | Equal to or greater than 30 weight percent | Equal to or greater than 30 weight percent | Equal to or greater than 30 weight percent |
| Polyether 3 | Equal to or greater than 30 weight percent | Equal to or greater than 30 weight percent | Equal to or greater than 30 weight percent |
| Polyether 4 | Equal to or greater than 30 weight percent | Equal to or greater than 30 weight percent | Equal to or greater than 30 weight percent |
| Polyether 5 | Equal to or greater than 30 weight percent | Equal to or greater than 30 weight percent | Equal to or greater than 30 weight percent |
| Polyether 6 | Equal to or greater than 30 weight percent | Equal to or greater than 30 weight percent | Equal to or greater than 30 weight percent |
| Polyether 7 | Equal to or greater than 30 weight percent | Equal to or greater than 30 weight percent | Equal to or greater than 30 weight percent |
| Polyether 8 | Equal to or greater than 30 weight percent | Equal to or greater than 30 weight percent | Equal to or greater than 30 weight percent |
| Polyether 9 | Equal to or greater than 30 weight percent | Equal to or greater than 30 weight percent | Equal to or greater than 30 weight percent |
| Polyether 10 | Equal to or greater than 30 weight percent | Equal to or greater than 30 weight percent | Equal to or greater than 30 weight percent |
| Polyether 11 | Equal to or greater than 30 weight percent | Equal to or greater than 30 weight percent | Equal to or greater than 30 weight percent |
| Polyether 12 | Equal to or greater than 30 weight percent | Equal to or greater than 30 weight percent | Equal to or greater than 30 weight percent |
| Polyether 13 | Equal to or greater than 30 weight percent | Equal to or greater than 30 weight percent | Equal to or greater than 30 weight percent |
| Polyether 14 | Equal to or greater than 30 weight percent | Equal to or greater than 30 weight percent | Equal to or greater than 30 weight percent |
| Polyether 15 | Equal to or greater than 30 weight percent | Equal to or greater than 30 weight percent | Equal to or greater than 30 weight percent |
| Polyether 16 | Equal to or greater than 30 weight percent | Equal to or greater than 30 weight percent | Equal to or greater than 30 weight percent |
| Polyether 17 | Equal to or greater than 30 weight percent | Equal to or greater than 30 weight percent | Equal to or greater than 30 weight percent |
| Polyether 18 | Equal to or greater than 30 weight percent | Equal to or greater than 30 weight percent | Equal to or greater than 30 weight percent |
| Polyether 19 | Equal to or greater than 30 weight percent | Equal to or greater than 30 weight percent | Equal to or greater than 30 weight percent |
| Polyether 20 | Equal to or greater than 30 weight percent | Equal to or greater than 30 weight percent | Equal to or greater than 30 weight percent |
| Polyether 21 | Equal to or greater than 30 weight percent | Equal to or greater than 30 weight percent | Equal to or greater than 30 weight percent |
| Polyether 22 | Equal to or greater than 30 weight percent | Equal to or greater than 30 weight percent | Equal to or greater than 30 weight percent |
| Polyether 23 | Equal to or greater than 30 weight percent | Equal to or greater than 30 weight percent | Equal to or greater than 30 weight percent |
| Polyether 24 | Equal to or greater than 30 weight percent | Equal to or greater than 30 weight percent | Equal to or greater than 30 weight percent |
| Polyether 25 | Equal to or greater than 30 weight percent | Equal to or greater than 30 weight percent | Equal to or greater than 30 weight percent |
| Polyether 26 | Equal to or greater than 30 weight percent | Equal to or greater than 30 weight percent | Equal to or greater than 30 weight percent |
| Polyether 27 | Equal to or greater than 30 weight percent | Equal to or greater than 30 weight percent | Equal to or greater than 30 weight percent |
| Polyether 28 | Equal to or greater than 30 weight percent | Equal to or greater than 30 weight percent | Equal to or greater than 30 weight percent |
| Polyether 29 | Equal to or greater than 30 weight percent | Equal to or greater than 30 weight percent | Equal to or greater than 30 weight percent |
| Polyether 30 | Equal to or greater than 30 weight percent | Equal to or greater than 30 weight percent | Equal to or greater than 30 weight percent |
| Polyether 31 | Equal to or greater than 30 weight percent | Equal to or greater than 30 weight percent | Equal to or greater than 30 weight percent |
| Polyether 32 | Equal to or greater than 30 weight percent | Equal to or greater than 30 weight percent | Equal to or greater than 30 weight percent |
| Polyether 33 | Equal to or greater than 30 weight percent | Equal to or greater than 30 weight percent | Equal to or greater than 30 weight percent |
| Polyether 34 | Equal to or greater than 30 weight percent | Equal to or greater than 30 weight percent | Equal to or greater than 30 weight percent |
| Polyether 35 | Equal to or greater than 30 weight percent | Equal to or greater than 30 weight percent | Equal to or greater than 30 weight percent |
| Polyether 36 | Equal to or greater than 30 weight percent | Equal to or greater than 30 weight percent | Equal to or greater than 30 weight percent |
| Polyether 37 | Equal to or greater than 30 weight percent | Equal to or greater than 30 weight percent | Equal to or greater than 30 weight percent |
| Polyether 38 | Equal to or greater than 30 weight percent | Equal to or greater than 30 weight percent | Equal to or greater than 30 weight percent |
| Polyether 39 | Equal to or greater than 30 weight percent | Equal to or greater than 30 weight percent | Equal to or greater than 30 weight percent |
| Polyether 40 | Equal to or greater than 30 weight percent | Equal to or greater than 30 weight percent | Equal to or greater than 30 weight percent |
| Polyether 41 | Less than 5 weight percent | Less than 5 weight percent | Less than 5 weight percent |
| Polyether 42 | Less than 5 weight percent | Less than 5 weight percent | Less than 5 weight percent |
| Polyether 43 | Less than 5 weight percent | Less than 5 weight percent | Less than 5 weight percent |
| Comp. Compound 1 | 1 weight percent | 10 weight percent | 10 weight percent |
| Sec-butyl stearate | 1 weight percent | 10 weight percent | 10 weight percent |

Evaluation Results

The followings can be determined from the results given in Table 3.

(i) Of the polyether compounds denoted by general formula (1), polyethers 1 to 25 corresponding to general formulas (1) and (2) all had good compatibility with the various binder resins employed in particulate magnetic recording media.

(ii) Of the polyether compounds denoted by general formula (II), polyethers 26 to 40 corresponding to general formula (3) also had good compatibility with the various binder resins employed in particulate magnetic recording media.

(iii) Of the polyether compounds denoted by general formula (I), polyether 41, which corresponded to neither general formula (1) nor (2), and of the polyether compounds denoted by general formula (II), polyethers 42 and 43, which did not correspond to general formula (3), had low compatibility with the above binders in the same manner as Comparative Compound 1, which was a carbonic acid ester compound, and sec-butyl stearate.

Examples 2-1 to 2-4, Comparative Examples 2-1, 2-2

(1) Preparation of Magnetic Layer Coating Liquid

| | |
|---|---|
| Acicular ferromagnetic metal powder: (Composition: Fe/Co/Al/Y = 67/20/8/5 (atom percent); surface treatment layer: $Al_2O_3$, $Y_2O_3$; coercivity (Hc): 183 kA/m; crystallite size: 12.5 nm; average major axis length: 45 nm; average acicular ratio: 6; BET specific surface area ($S_{BET}$): 60 m$^2$/g; saturation magnetization ($\sigma s$): 140 A · m$^2$/kg (140 emu/g)) | 100 parts |
| Vinyl chloride copolymer: | 12 parts |
| Polyurethane resin (based on branched chain-containing polyester polyol/diphenylmethane diisocyanate; hydrophilic polar group contained: —$SO_3Na$ = 70 eq/ton): | 8 parts |
| Phenyl phosphonic acid: | 3 parts |
| α-$Al_2O_3$ (average particle size: 0.06 μm): | 2 parts |
| Carbon black (average particle size: 20 nm): | 2 parts |
| Cyclohexanone: | 110 parts |
| Methyl ethyl ketone: | 100 parts |
| Toluene: | 100 parts |
| Stearic acid: | 1 part |
| Stearic acid amide: | 0.3 parts |
| Lubricant indicated in Table 4: | 1 part |

The above components were kneaded in a continuous kneader and then dispersed in a sand mill. To the various dispersions obtained were added 3 parts of polyisocyanate and 40 parts of a mixed solvent of methyl ethyl ketone and cyclohexanone. The mixtures were then filtered using a filter having a mean pore diameter of 1 μm to prepare a magnetic layer coating liquid.

(2) Preparation of Nonmagnetic Layer Coating Liquid

| | |
|---|---|
| Nonmagnetic powder (α-$Fe_2O_3$): (average major axis length: 0.15 μm; BET specific surface area: 52 m$^2$/g; pH: 7.6) | 80 parts |
| Carbon black: (average primary particle diameter: 16 nm; DBP oil absorption capacity: 80 mL/100 g; pH: 8.0; BET specific surface area: 250 m$^2$/g; volatile content: 1.5 percent) | 20 parts |
| Vinyl chloride copolymer: (—$SO_3Na$ content: 5 × 10$^{-6}$ mole/g; degree of polymerization: 280) | 12 parts |
| Polyester polyurethane resin: (neopentyl glycol/caprolactone polyol/diphenylmethane diisocyanate = 0.9/2.6/1; —$SO_3Na$ content: 1 × 10$^{-4}$ mole/g) | 5 parts |
| Stearic acid: | 1 part |
| Stearic acid amide: | 0.3 part |
| Methyl ethyl ketone: | 100 parts |
| Cyclohexanone: | 50 parts |
| Lubricant indicated in Table 4: | 1 part |

The above components were kneaded in a continuous kneader and then dispersed in a sand mill. To the dispersion obtained was added 1 part of polyisocyanate and 40 parts of a mixed solvent of methyl ethyl ketone and cyclohexanone. The mixture was then filtered using a filter having a mean pore diameter of 1 μm to prepare a nonmagnetic layer coating liquid.

(3) Preparation of Backcoat Layer Coating Liquid

1) Mixture A

| | |
|---|---|
| Carbon black (BP-800 made by Cabot Corporation): | 100 parts |
| Nitrocellulose (RS1/2 made by Daicel): | 100 parts |
| Polyurethane resin (N2301 made by Nippon Polyurethane Industry Co., Ltd.): | 30 parts |
| Copper oleate: | 5 parts |
| Copper phthalocyanine: | 5 parts |
| Precipitated barium sulfate: | 5 parts |
| Methyl ethyl ketone: | 500 parts |
| Toluene: | 500 parts |

2) Mixture B

| | |
|---|---|
| Carbon black: | 100 parts |
| Stearic acid adsorption level (SSA): | 8.5 m$^2$/g |
| Average particle diameter: | 270 nm |
| DBF oil absorption capacity: | 36 mL/100 g |
| pH: | 10 |
| Nitrocellulose (RS1/2 made by Daicel): | 100 parts |
| Polyurethane resin (N2301 made by Nippon Polyurethane Industry Co., Ltd.): | 30 parts |
| Methyl ethyl ketone: | 300 parts |
| Toluene: | 300 parts |

Mixture A was prekneaded in a roll mill, mixtures A and B were dispersed in a sand grinder, and the following components were added per 100 parts of dispersion obtained:

| | |
|---|---|
| Polyester resin (Vylon 300 made by Toyobo Co., Ltd.): | 5 parts |
| Polyisocyanate: | 5 parts |
| Polyisocyanate (Coronate L made by Nippon Polyurethane Industry Co., Ltd.): | 5 parts |

(4) Manufacture of Magnetic Recording Medium

Next, the coating quantities of the magnetic layer and nonmagnetic layer coating liquids were adjusted to yield a nonmagnetic layer with a thickness of 1.0 μm upon drying and a magnetic layer positioned thereover with a thickness in a final product of 0.1 μm, and simultaneous multilayer coating was conducted on a base film. Polyethylene terephthalate that was 5.0 μm in thickness and had a centerline average roughness Ra (cut-off value: 0.25 mm) of 0.005 μm was employed as the base film. While the magnetic layer and nonmagnetic layer were still wet, they were oriented with a 0.3 T rare earth magnet and a 0.15 T solenoid and dried. A backcoat layer coating liquid was then applied and dried to a dry thickness of 0.5 μm on the opposite side of the base film from the side on which the magnetic layer was positioned. The product was then processed with a seven-stage calender comprised solely of metal rolls at a temperature of 90° C. and slit to ½ inch width to obtain a magnetic tape. The Ra of a 40 μm square portion of the magnetic layer surface of the magnetic tape obtained was 3.5 nm when measured with a Veeco Japan (Ltd.) Nanoscope IV.

Friction Evaluation Method

A tape was run for five hours (100,000 passes) at a humidity of 80 percent, a temperature of 40° C., and a speed of 0.3 m/s with a load of 100 g using a friction evaluating apparatus made by FUJIFILM CORPORATION. Once the running had been stopped, the head member was positioned on the tape in a static state for 10 hours. The startup friction was measured when running was resumed. The results are given in Table 4. A startup friction of less than 250 g can be determined to indicate no drop in running durability due to sticking during the resumption of running. The results are given in Table 4.

TABLE 4

| | | Friction | |
|---|---|---|---|
| | Lubricant | Measured value | Evaluation |
| Example 2-1 | Polyether 1 | 140 g | ○ |
| Example 2-2 | Polyether 2 | 140 g | ○ |
| Example 2-3 | Polyether 3 | 140 g | ○ |
| Example 2-4 | Polyether 4 | 140 g | ○ |
| Comp. Ex.2-1 | Comp. Compound 1 | Equal to or greater than 250 g | X |
| Comp. Ex.2-2 | Sec-butyl stearate | Equal to or greater than 250 g | X |

Evaluation Results

As indicated in Table 4, the magnetic tapes of Examples 2-1 to 2-4, in which the polyether compounds obtained in Synthesis Examples 1 to 4 were employed as lubricants, exhibited lower startup friction when running was resumed than Comparative Examples 2-1 and 2-2, and were thus determined to have exhibited good running durability.

The polyether compounds of the present invention are useful as lubricants for magnetic recording media and can be suitably employed to lower the coefficient of friction of sliding metal members.

Although the present invention has been described in considerable detail with regard to certain versions thereof, other versions are possible, and alterations, permutations and equivalents of the version shown will become apparent to those skilled in the art upon a reading of the specification and study of the drawings. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

Having now fully described this invention, it will be understood to those of ordinary skill in the art that the methods of the present invention can be carried out with a wide and equivalent range of conditions, formulations, and other parameters without departing from the scope of the invention or any embodiments thereof.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

What is claimed is:

1. A polyether compound denoted by general formula (II);

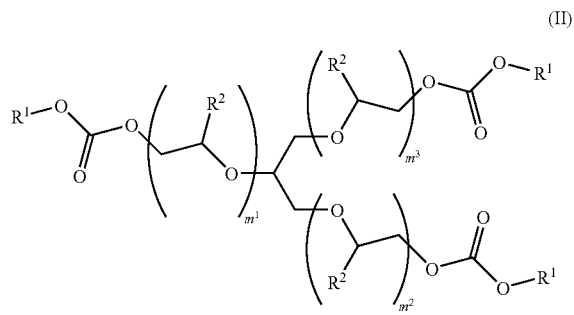

(II)

wherein, in general formula (II), $R^1$ denotes a linear or branched alkyl group, $R^2$ denotes a hydrogen atom or a methyl group, and each of $m^1$, $m^2$, and $m^3$ independently denotes an integer of equal to or greater than 1 but equal to or lower than 100.

2. The polyether compound according to claim 1, which is a polyether compound denoted by general formula (3);

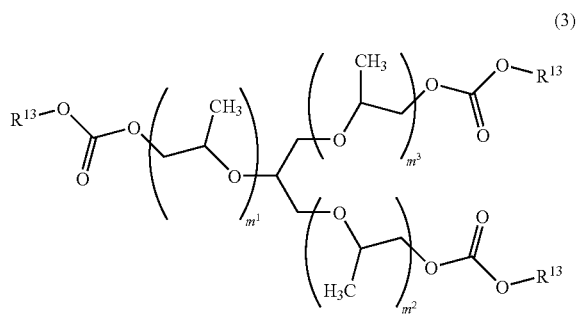

(3)

wherein, in general formula (3), $R^{13}$ denotes a linear or branched alkyl group with 1 to 8 carbon atoms, and each of $m^1$, $m^2$, and $m^3$ independently denotes an integer of equal to or greater than 1 but equal to or lower than 100.

3. The polyether compound according to claim 1, wherein in general formula (II), each $R^1$ independently denotes a branched alkyl group.

4. A polyether compound denoted by general formula (2);

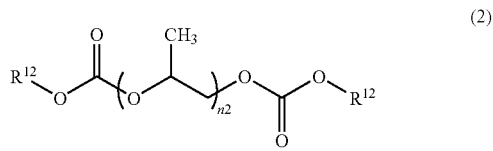

(2)

wherein, in general formula (2), each $R^{12}$ independently denotes a branched alkyl group with 1 to 8 carbon atoms, and n2 denotes an integer of equal to or greater than 2 but equal to or lower than 100.

5. A lubricant composition comprising a polyether compound comprising an alkylene oxide residue and a carbonic acid ester residue, wherein the polyether compound comprises a polyether compound denoted by general formula (II):

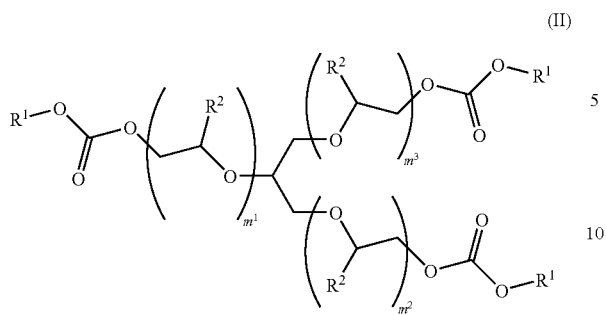

(II)

wherein, in general formula (II), $R^1$ denotes a linear or branched alkyl group, $R^2$ denotes a hydrogen atom or a methyl group, and each of $m^1$, $m^2$, and $m^3$ independently denotes an integer of equal to or greater than 1 but equal to or lower than 100.

6. The lubricant composition according to claim 5, wherein the polyether compound denoted by general formula (II) is a polyether compound denoted by general formula (3);

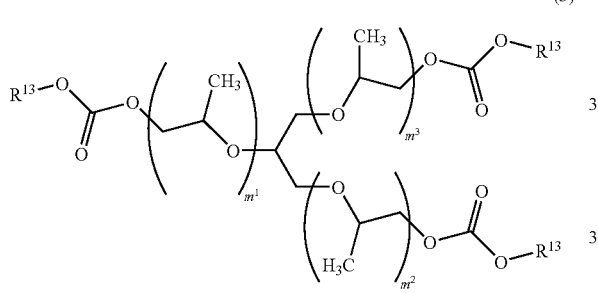

(3)

wherein, in general formula (3), $R^{13}$ denotes a linear or branched alkyl group with 1 to 8 carbon atoms, and each of $m^1$, $m^2$, and $m^3$ independently denotes an integer of equal to or greater than 1 but equal to or lower than 100.

7. A magnetic recording medium comprising a layer comprising the lubricant composition according to claim 5.

8. The magnetic recording medium according to claim 7, wherein
the magnetic recording medium comprises a magnetic layer comprising a ferromagnetic powder and a binder on a nonmagnetic support,
the layer comprising the lubricant composition is the magnetic layer, and
the polyether compound denoted by general formula (II) in the lubricant composition is at least one polyether compound denoted by general formula (3):

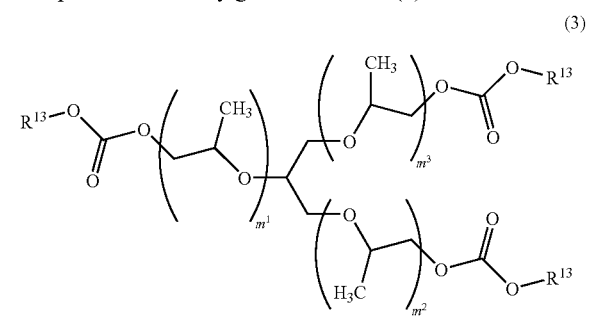

(3)

wherein, in general formula (3), $R^{13}$ denotes a linear or branched alkyl group with 1 to 8 carbon atoms, and each of $m^1$, $m^2$, and $m^3$ independently denotes an integer of equal to or greater than 1 but equal to or lower than 100.

9. The magnetic recording medium according to claim 7, wherein
the magnetic recording medium comprises a nonmagnetic layer comprising a nonmagnetic powder and a binder and a magnetic layer comprising a ferromagnetic powder and a binder in this order on a nonmagnetic support,
the layer comprising the lubricant composition is the nonmagnetic layer, and
the polyether compound denoted by general formula (II) in the lubricant composition is at least one polyether compound denoted by general formula (3):

(3)

wherein, in general formula (3), $R^{13}$ denotes a linear or branched alkyl group with 1 to 8 carbon atoms, and each of $m^1$, $m^2$, and $m^3$ independently denotes an integer of equal to or greater than 1 but equal to or lower than 100.

10. The magnetic recording medium according to claim 8, wherein the magnetic layer further comprises a fatty acid and/or a fatty acid amide.

11. The magnetic recording medium according to claim 9, wherein the magnetic layer comprises at least one polyether compound denoted by general formula (3).

12. The magnetic recording medium according to claim 9, wherein the nonmagnetic layer further comprises a fatty acid and/or a fatty acid amide.

13. The magnetic recording medium according to claim 11, wherein the magnetic layer further comprises a fatty acid and/or a fatty acid amide.

\* \* \* \* \*